US011359018B2

(12) United States Patent
Lantto et al.

(10) Patent No.: US 11,359,018 B2
(45) Date of Patent: Jun. 14, 2022

(54) ANTI-PD-1 ANTIBODIES AND COMPOSITIONS

(71) Applicant: SYMPHOGEN A/S, Ballerup (DK)

(72) Inventors: Johan Lantto, Lund (SE); Thomas Bouquin, Allerød (DK); Klaus Koefoed, København S (DK); Torben Gjetting, Jyllinge (DK); Vikram Kjoller Bhatia, Charlottenlund (DK); Monika Gad, Allerød (DK); Gunther Roland Galler, Jyllinge (DK); Camilla Frohlich, København Ø (DK)

(73) Assignee: Symphogen A/S, Ballerup (DK)

( * ) Notice: Subject to any disclaimer, the term of this patent is extended or adjusted under 35 U.S.C. 154(b) by 145 days.

(21) Appl. No.: 16/461,957

(22) PCT Filed: Nov. 17, 2017

(86) PCT No.: PCT/EP2017/079615
§ 371 (c)(1),
(2) Date: May 17, 2019

(87) PCT Pub. No.: WO2018/091661
PCT Pub. Date: May 24, 2018

(65) Prior Publication Data
US 2019/0367616 A1    Dec. 5, 2019

Related U.S. Application Data

(60) Provisional application No. 62/424,163, filed on Nov. 18, 2016.

(51) Int. Cl.
*C07K 16/28* (2006.01)
*A61K 39/395* (2006.01)
*A61P 35/00* (2006.01)
*C07K 16/46* (2006.01)
*C07K 14/705* (2006.01)
*A61K 45/06* (2006.01)
*A61K 39/00* (2006.01)

(52) U.S. Cl.
CPC ...... *C07K 16/2818* (2013.01); *A61K 39/3955* (2013.01); *C07K 16/468* (2013.01); *A61K 45/06* (2013.01); *A61K 2039/505* (2013.01); *C07K 14/70521* (2013.01); *C07K 2317/33* (2013.01); *C07K 2317/51* (2013.01); *C07K 2317/52* (2013.01); *C07K 2317/565* (2013.01); *C07K 2317/567* (2013.01); *C07K 2317/76* (2013.01); *C07K 2317/92* (2013.01)

(58) Field of Classification Search
CPC .......... C07K 16/2818; C07K 14/70521; A61K 39/3955
See application file for complete search history.

(56) References Cited

U.S. PATENT DOCUMENTS

| 8,927,697 | B2 | 1/2015 | Davis et al. |
| 9,492,540 | B2* | 11/2016 | Korman ............ C07K 16/28 |
| 11,034,765 | B2 | 6/2021 | Galler et al. |
| 2011/0229461 | A1 | 9/2011 | Tyson et al. |
| 2014/0328833 | A1 | 11/2014 | Korman et al. |
| 2015/0203579 | A1 | 7/2015 | Papadopoulos et al. |
| 2015/0210769 | A1 | 7/2015 | Freeman et al. |

FOREIGN PATENT DOCUMENTS

| WO | 2006/029879 A1 | 3/2006 |
| WO | 2006/121168 A1 | 11/2006 |
| WO | 2008/019817 A1 | 2/2008 |
| WO | 2008/156712 A1 | 12/2008 |
| WO | 2010/029434 A1 | 3/2010 |
| WO | 2010/029435 A1 | 3/2010 |
| WO | 2011/110621 A1 | 9/2011 |
| WO | 2011/159877 A1 | 12/2011 |
| WO | 2012/135408 A1 | 10/2012 |
| WO | 2015/035606 A1 | 3/2015 |
| WO | 2015/042246 A1 | 3/2015 |
| WO | 2015/048312 A1 | 4/2015 |
| WO | 2015/112800 A1 | 7/2015 |
| WO | 2015/112900 A1 | 7/2015 |
| WO | 2016/014688 A1 | 1/2016 |
| WO | 2016/092419 A1 | 6/2016 |
| WO | 2017/055547 A1 | 4/2017 |
| WO | 2017/198741 A1 | 11/2017 |

OTHER PUBLICATIONS

Ferrara et al (2015. mAbs. 7(1): 32-41).*
Benjamini et al, 1991. Immunology: A Short Course, 2nd edition, p. 40 only.*
Storz et al (2016. mAbs. 8:1).*
Vincent et al, 2012. Biotechnol. J. 7:1444-1450.*
Anonymous: "Naturally optimized human antibodies," 1-16 (2016). Retrieved from the Internet: URL:http://content.stockpr.com/omniab/db/2 52/746/file/OmniAb.pdf [retrieved on Jan. 9, 2018].
Fenwick et al., "Identification of novel antagonistic anti-PD-1 antibodies that are non-blocking of the PD-1 / PD-L1 Interaction," Journal of Clinical Oncology 34:15 Suppl (2016).
Lee et al., "Structural basis of checkpoint blockade by monoclonal antibodies in cancer immunotherapy," Nature Communications 7:13354 (2016).
Scapin et al., "Structure of full-length human anti-PD1 therapeutic IgG4 antibody pembrolizumab," Nat Struct Mol Biol 22(12):953-8 (2015).
Cheng et al., "Structure and interactions of the human programmed cell death 1 receptor," J Biol Chem 288(17):11771-85 (2013).
Colman, "Effects of amino acid sequence changes on antibody-antigen interactions," Res Immunol. 145(1):33-6 (1994).
Hu et al., "Preparation and characterization of a novel monoclonal antibody against human PD-1," Current Immunology, 30(1):24-9 (2010) (with English abstract).

(Continued)

*Primary Examiner* — Zachary C Howard
(74) *Attorney, Agent, or Firm* — Steptoe & Johnson LLP; Z. Ying Li; Wyan-Ching M. Lee

(57) ABSTRACT

This invention relates to anti-PD-1 antibodies and methods of using them in treating diseases and conditions related to PD-1activity, e.g., cancer.

20 Claims, 25 Drawing Sheets

Specification includes a Sequence Listing.

(56) References Cited

OTHER PUBLICATIONS

Lin et al., "Improved affinity of a chicken single-chain antibody to avian infectious bronchitis virus by site-directed mutagenesis of complementarity-determining region H3," African Journal of Biotechnology 10(79):18294-302 (2011).
Mariuzza et al., "Structural basis of antigen-antibody recognition," Ann Rev Biophys Biophys Chem. 16:139-59 (1987).
McCarthy et al., "Altering the fine specificity of an anti-Legionella single chain antibody by a single amino acid insertion," J. Immunol. Methods, 251(1-2):137-49 (2001).
Na et al., "Structural basis for blocking PD-1-mediated immune suppression by therapeutic antibody pembrolizumab," Cell Res. 27(1):147-50 (2017).
Pan et al., "Blocking neuropilin-1 function has an additive effect with anti-VEGF to inhibit tumor growth," Cancer Cell 11(1):53-67 (2007).
Rayner et al., "The solution structures of two human IgG 1 antibodies show conformational stability and accommodate their C1q and FcγR ligands," J Biol Chem 290(13):8420-38 (2015).
Rudikoff et al., "Single amino acid substitution altering antigen-binding specificity," Proc Natl Acad Sci USA. 79(6):1979-83 (1982).
Wang et al., "In vitro characterization of the anti-PD-1 antibody nivolumab, BMS-936558, and in vivo toxicology in non-human primates," Cancer Immunol Res 2(9):846-56 (2014).
Zak et al., "Structure of the complex of human programmed death 1, PD-1, and its ligand PD-L1," Structure 23(12):2341-8 (2015).
Anonymous, "Anti-LAG-3 or Urelumab Alone and in Combination with Nivolumab in Treating Patients with Recurrent Glioblastoma," ClinicalTrials.gov (2016).
Anonymous, "NCT02608268: Phase I-Ib/II Open-label Multicenter Study of the Safety and Efficacy of MBG453 as Single Agent and in Combination with PDR001 in Adult Patients with Advanced Malignancies," ClinicalTrials.gov (2017).
Jing et al., "Combined immune checkpoint protein blockade and low dose whole body irradiation as immunotherapy for myeloma," J Immunother Cancer 3(1):2 (2015).
Kehry, "Targeting PD-1, TIM-3 and LAG-3 in combination for improved immunotherapy combinations," Journal for Immunotherapy of Cancer, 1 page (2015). [Retrieved from Internet—URL: https://www.tesarobio.com/application/files/3014/7552/4272/AACRApr2015.pdf].
Liu et al., "Targeting PD-1 and Tim-3 pathways to reverse CD8 T-cell exhaustion and enhance ex vivo T-cell responses to autologous dendritic/tumor vaccines," J Immunother 39(4):171-80 (2016).
Moon, "Abstract 1641: Dual antibody blockade of TIM3 and PD1 on NYES01 redirected human T cells leads to augmented control of lung cancer tumors," Cancer Research 77: 1641(2017).

* cited by examiner

18040

18049

18098

18113

18201

18247

18250

18325

18366

18400

18413

18483 no PD-L1-PE
no mAb control mAb non-blocking mAb

SEQUENCE LISTING

<160> NUMBER OF SEQ ID NOS: 115

<210> SEQ ID NO 1
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (35)..(35)
<223> OTHER INFORMATION: /replace="Ser"
<220> FEATURE:
<221> NAME/KEY: VARIANT
<222> LOCATION: (84)..(84)
<223> OTHER INFORMATION: /replace="Asn"
<220> FEATURE:
<221> NAME/KEY: MISC_FEATURE
<222> LOCATION: (1)..(117)
<223> OTHER INFORMATION: /note="Variant residues given in the sequence
      have no preference with respect to those in the annotations
      for variant positions"

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Thr Gly Ser Thr Ile Tyr Tyr Ala Asp Ser Val
    50                  55                  60

```
Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Ala Thr Asn Trp Gly Ser Asp Tyr Trp Gly Gln Gly Thr Leu
            100                 105                 110

Val Thr Val Ser Ser
            115

<210> SEQ ID NO 2
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: VARIANT
<222> LOCATION: (40)..(40)
<223> OTHER INFORMATION: /replace="Ala"
<220> FEATURE:
<221> NAME/KEY: VARIANT
<222> LOCATION: (55)..(55)
<223> OTHER INFORMATION: /replace="Tyr"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 2

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Phe Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys

<210> SEQ ID NO 3
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 3

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Gly Asn Tyr Tyr Gly Asp Phe Trp Gly Gln Gly Thr Leu
            100                 105                 110

Val Thr Val Ser Ser
            115
```

```
<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (53)..(53)
<223> OTHER INFORMATION: /replace="Ser"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"
```

<400> SEQUENCE: 4

```
Glu Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105
```

```
<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (13)..(13)
<223> OTHER INFORMATION: /replace="Gln"
<220> FEATURE:
<221> NAME/KEY: VARIANT
<222> LOCATION: (35)..(35)
<223> OTHER INFORMATION: /replace="Ser"
<220> FEATURE:
<221> NAME/KEY: VARIANT
<222> LOCATION: (46)..(46)
<223> OTHER INFORMATION: /replace="Glu"
<220> FEATURE:
<221> NAME/KEY: VARIANT
<222> LOCATION: (50)..(50)
<223> OTHER INFORMATION: /replace="Ala"
<220> FEATURE:
<221> NAME/KEY: VARIANT
<222> LOCATION: (77)..(77)
<223> OTHER INFORMATION: /replace="Asn"
<220> FEATURE:
<221> NAME/KEY: VARIANT
<222> LOCATION: (80)..(80)
<223> OTHER INFORMATION: /replace="Tyr"
<220> FEATURE:
<221> NAME/KEY: VARIANT
<222> LOCATION: (115)..(115)
<223> OTHER INFORMATION: /replace="Met"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
      for variant positions"
```

<400> SEQUENCE: 5

Gln Val Gln Leu Gln Glu Ser Gly Gly Gly Leu Val Arg Pro Gly Gly
1               5                   10                  15

Ser Leu Arg Leu Ser Cys Ala Ala Ser Gly Phe Thr Phe Ser Ser Phe
            20                  25                  30

Ala Met Asn Trp Val Arg Gln Ala Pro Gly Lys Gly Leu Val Trp Val
        35                  40                  45

Ser Thr Ile Thr Gly Gly Thr Thr Ser Tyr Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Ala Lys Trp Gly Ser Trp Ser Ala Gly Ala Phe Asp Ile Trp Gly Gln
            100                 105                 110

Gly Thr Thr Val Thr Val Ser Ser
            115                 120

```
<210> SEQ ID NO 6
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(4)
<223> OTHER INFORMATION: /replace="Met"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 6

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 7
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (64)..(64)
<223> OTHER INFORMATION: /replace="Val"
<220> FEATURE:
<221> NAME/KEY: MISC_FEATURE
<222> LOCATION: (1)..(117)
<223> OTHER INFORMATION: /note="Variant residues given in the sequence
      have no preference with respect to those in the annotations
      for variant positions"

<400> SEQUENCE: 7

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Ala
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Asp Thr Asn Trp Ala Phe Asp Tyr Trp Gly Gln Gly Thr Leu
            100                 105                 110

Val Thr Val Ser Ser
        115

<210> SEQ ID NO 8
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (3)..(3)
<223> OTHER INFORMATION: /replace="Val"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (69)..(69)
<223> OTHER INFORMATION: /replace="Ser"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 8

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ala Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Arg Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Thr Pro Arg Thr Phe Gly Gln Gly Thr Lys Val Glu Ile
            100                 105                 110

Lys

<210> SEQ ID NO 9
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(5)
<223> OTHER INFORMATION: /replace="Gln"
<220> FEATURE:
<221> NAME/KEY: VARIANT
<222> LOCATION: (59)..(59)
<223> OTHER INFORMATION: /replace="Asn"

```
<220> FEATURE:
<221> NAME/KEY: VARIANT
<222> LOCATION: (76)..(76)
<223> OTHER INFORMATION: /replace="Lys"
<220> FEATURE:
<221> NAME/KEY: VARIANT
<222> LOCATION: (83)..(83)
<223> OTHER INFORMATION: /replace="Leu"
<220> FEATURE:
<221> NAME/KEY: MISC_FEATURE
<222> LOCATION: (1)..(119)
<223> OTHER INFORMATION: /note="Variant residues given in the sequence
      have no preference with respect to those in the annotations
      for variant positions"

<400> SEQUENCE: 9

Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Asp Gly Thr Thr Tyr Asn Pro Ser Leu
    50                  55                  60

Lys Ser Arg Val Thr Ile Ser Val Asp Lys Ser Arg Asn Gln Phe Ser
65                  70                  75                  80

Leu Lys Met Ser Ser Val Thr Ala Ala Asp Thr Ala Val Tyr Tyr Cys
                85                  90                  95

Ala Arg Gly Asp Trp Gly Ser Gly Ala Phe Asp Ile Trp Gly Gln Gly
            100                 105                 110

Thr Met Val Thr Val Ser Ser
        115

<210> SEQ ID NO 10
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Ala"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 11
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (10)..(10)
<223> OTHER INFORMATION: /replace="Gly"
<220> FEATURE:
<221> NAME/KEY: VARIANT
<222> LOCATION: (16)..(16)
<223> OTHER INFORMATION: /replace="Gly"
<220> FEATURE:
<221> NAME/KEY: MISC_FEATURE
<222> LOCATION: (1)..(117)
<223> OTHER INFORMATION: /note="Variant residues given in the sequence
      have no preference with respect to those in the annotations
      for variant positions"

<400> SEQUENCE: 11

Gln Val Gln Leu Val Glu Ser Gly Gly Asp Leu Val Lys Pro Gly Arg
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Trp Ala Phe Asp Tyr Trp Gly Gln Gly Thr Leu
            100                 105                 110

Val Thr Val Ser Ser
        115

<210> SEQ ID NO 12
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (55)..(55)
<223> OTHER INFORMATION: /replace="Tyr"
```

```
<220> FEATURE:
<221> NAME/KEY: VARIANT
<222> LOCATION: (93)..(93)
<223> OTHER INFORMATION: /replace="Tyr"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 12

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Phe Tyr Ser Thr Pro Arg Thr Phe Gly Gln Gly Thr Lys Val Glu Ile
            100                 105                 110

Lys

<210> SEQ ID NO 13
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (50)..(50)
<223> OTHER INFORMATION: /replace="Tyr"
<220> FEATURE:
<221> NAME/KEY: VARIANT
<222> LOCATION: (59)..(59)
<223> OTHER INFORMATION: /replace="Tyr"
<220> FEATURE:
<221> NAME/KEY: VARIANT
<222> LOCATION: (61)..(61)
<223> OTHER INFORMATION: /replace="Ala"
<220> FEATURE:
<221> NAME/KEY: MISC_FEATURE
<222> LOCATION: (1)..(117)
<223> OTHER INFORMATION: /note="Variant residues given in the sequence
      have no preference with respect to those in the annotations
      for variant positions"

<400> SEQUENCE: 13

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Arg Asp Tyr
            20                  25                  30

Tyr Met Ser Trp Ile Arg Gln Ala Pro Gly Lys Gly Leu Glu Trp Val
        35                  40                  45
```

```
Ser His Ile Ser Ser Gly Ser Ile Ile Asp Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Trp Ala Leu Asp Tyr Trp Gly Gln Gly Thr Leu
            100                 105                 110

Val Thr Val Ser Ser
        115

<210> SEQ ID NO 14
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (3)..(3)
<223> OTHER INFORMATION: /replace="Val"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (55)..(55)
<223> OTHER INFORMATION: /replace="Tyr"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 14

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: VARIANT
<222> LOCATION: (35)..(35)
<223> OTHER INFORMATION: /replace="Ser"
<220> FEATURE:
<221> NAME/KEY: VARIANT
<222> LOCATION: (49)..(49)
<223> OTHER INFORMATION: /replace="Ser"
<220> FEATURE:
<221> NAME/KEY: VARIANT
<222> LOCATION: (50)..(50)
<223> OTHER INFORMATION: /replace="Ala"
<220> FEATURE:
<221> NAME/KEY: VARIANT
<222> LOCATION: (73)..(73)
<223> OTHER INFORMATION: /replace="Asp"
<220> FEATURE:
<221> NAME/KEY: VARIANT
<222> LOCATION: (78)..(78)
<223> OTHER INFORMATION: /replace="Thr"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
      for variant positions"

<400> SEQUENCE: 15

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Val Met Asn Trp Val Arg Gln Ala Pro Gly Lys Gly Leu Glu Trp Val
        35                  40                  45

Ala Thr Ile Ser Gly Ser Gly Val Asp Thr Tyr Tyr Ala Asp Ser Val
    50                  55                  60

Lys Gly Arg Phe Thr Ile Ser Arg Gly Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Ser Trp Ser Ala Gly Ala Phe Asp Ile Trp Gly Gln
            100                 105                 110

Gly Thr Met Val Thr Val Ser Ser
        115                 120

<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Asp"
```

```
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (4)..(4)
<223> OTHER INFORMATION: /replace="Met"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 16

Glu Ile Val Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 17
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: MISC_FEATURE
<222> LOCATION: (1)..(117)
<223> OTHER INFORMATION: /note="Variant residues given in the sequence
      have no preference with respect to those in the annotations
      for variant positions"

<400> SEQUENCE: 17

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Thr Asn Trp Gly Phe Asp Asn Trp Gly Gln Gly Thr Leu
            100                 105                 110

Val Thr Val Ser Ser
        115

<210> SEQ ID NO 18
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: VARIANT
<222> LOCATION: (40)..(40)
<223> OTHER INFORMATION: /replace="Ala"
<220> FEATURE:
<221> NAME/KEY: VARIANT
<222> LOCATION: (55)..(55)
<223> OTHER INFORMATION: /replace="Tyr"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 18

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Leu Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 19
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (43)..(43)
<223> OTHER INFORMATION: /replace="Gly"
```

```
<220> FEATURE:
<221> NAME/KEY: VARIANT
<222> LOCATION: (49)..(49)
<223> OTHER INFORMATION: /replace="Ile"
<220> FEATURE:
<221> NAME/KEY: VARIANT
<222> LOCATION: (59)..(59)
<223> OTHER INFORMATION: /replace="Asn"
<220> FEATURE:
<221> NAME/KEY: VARIANT
<222> LOCATION: (70)..(70)
<223> OTHER INFORMATION: /replace="Ile"
<220> FEATURE:
<221> NAME/KEY: VARIANT
<222> LOCATION: (111)..(111)
<223> OTHER INFORMATION: /replace="Gln"
<220> FEATURE:
<221> NAME/KEY: MISC_FEATURE
<222> LOCATION: (1)..(119)
<223> OTHER INFORMATION: /note="Variant residues given in the sequence
      have no preference with respect to those in the annotations
      for variant positions"

<400> SEQUENCE: 19

Gln Leu Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Lys Lys Gly Leu Glu Trp
        35                  40                  45

Val Gly Glu Ile Phe His Asp Gly Thr Thr Ser Tyr Asn Pro Ser Leu
    50                  55                  60

Lys Ser Arg Val Thr Met Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Trp Gly Ser Gly Ala Leu Asp Ile Trp Gly Pro Gly
            100                 105                 110

Thr Met Val Thr Val Ser Ser
        115

<210> SEQ ID NO 20
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Ala"
<220> FEATURE:
<221> NAME/KEY: VARIANT
<222> LOCATION: (3)..(3)
<223> OTHER INFORMATION: /replace="Gln"
<220> FEATURE:
<221> NAME/KEY: VARIANT
<222> LOCATION: (10)..(10)
<223> OTHER INFORMATION: /replace="Ser"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"
```

<400> SEQUENCE: 20

Glu Ile Val Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 21
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (48)..(48)
<223> OTHER INFORMATION: /replace="Val"
<220> FEATURE:
<221> NAME/KEY: VARIANT
<222> LOCATION: (50)..(50)
<223> OTHER INFORMATION: /replace="Ala"
<220> FEATURE:
<221> NAME/KEY: MISC_FEATURE
<222> LOCATION: (1)..(118)
<223> OTHER INFORMATION: /note="Variant residues given in the sequence
      have no preference with respect to those in the annotations
      for variant positions"

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Val Met Ser Trp Val Arg Gln Ala Pro Gly Lys Gly Leu Glu Trp Leu
        35                  40                  45

Ser Thr Ile Ser Gly Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Asp Leu Tyr Tyr Phe Asp Tyr Trp Gly Gln Gly Thr
            100                 105                 110

Leu Val Thr Val Ser Ser
        115

<210> SEQ ID NO 22
<211> LENGTH: 107
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (12)..(12)
<223> OTHER INFORMATION: /replace="Ser"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 22

Asp Ile Gln Leu Thr Gln Ser Pro Ser Ser Val Pro Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 23
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Glu"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: VARIANT
<222> LOCATION: (35)..(35)
<223> OTHER INFORMATION: /replace="Ser"
<220> FEATURE:
<221> NAME/KEY: MISC_FEATURE
<222> LOCATION: (1)..(117)
<223> OTHER INFORMATION: /note="Variant residues given in the sequence
      have no preference with respect to those in the annotations
      for variant positions"
```

<400> SEQUENCE: 23

Gln Val Gln Leu Gln Gln Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Trp Gly Ser Asp Tyr Trp Gly Gln Gly Thr Leu
            100                 105                 110

Val Thr Val Ser Ser
        115

<210> SEQ ID NO 24
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (3)..(3)
<223> OTHER INFORMATION: /replace="Val"
<220> FEATURE:
<221> NAME/KEY: VARIANT
<222> LOCATION: (40)..(40)
<223> OTHER INFORMATION: /replace="Ala"
<220> FEATURE:
<221> NAME/KEY: VARIANT
<222> LOCATION: (55)..(55)
<223> OTHER INFORMATION: /replace="Tyr"
<220> FEATURE:
<221> NAME/KEY: MISC_FEATURE
<222> LOCATION: (1)..(113)
<223> OTHER INFORMATION: /note="Variant residues given in the sequence
      have no preference with respect to those in the annotations
      for variant positions"

<400> SEQUENCE: 24

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Leu Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 25
<211> LENGTH: 990
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaagc cgccggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                     990
```

<210> SEQ ID NO 26
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Ala Ala Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 27
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 28
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Phe Thr Phe Ser Asp Tyr Tyr
1               5

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ser Ser Thr Gly Ser Thr Ile
1               5

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Cys Ala Arg Ala Thr Asn Trp Gly Ser Asp Tyr
1               5                   10

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 32

Gln Ser Val Leu Tyr Ser Ser Asn Asn Lys Asn Tyr
1               5                   10

<210> SEQ ID NO 33
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Trp Ala Ser
1

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Cys Gln Gln Tyr Tyr Ser Thr Pro Tyr Thr
1               5                   10

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Phe Thr Phe Ser Asn Tyr Gly
1               5

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ile Trp Tyr Asp Gly Ser Asp Lys
1               5

<210> SEQ ID NO 37
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Cys Ala Gly Gly Gly Asn Tyr Tyr Gly Asp Phe
1               5                   10
```

```
<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Gly Ile Arg Asn Asp
1               5

<210> SEQ ID NO 39
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Val Ala Ser
1

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Cys Leu Gln Tyr Asn Ser Tyr Pro Trp Thr
1               5                   10

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Phe Thr Phe Ser Ser Phe Ala
1               5

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ile Thr Gly Gly Gly Thr Thr Ser
1               5

<210> SEQ ID NO 43
<211> LENGTH: 14
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 43

Cys Ala Lys Trp Gly Ser Trp Ser Ala Gly Ala Phe Asp Ile
1               5                   10

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Gly Ile Ser Ser Trp
1               5

<210> SEQ ID NO 45
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Ala Ser
1

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Cys Gln Gln Ala Asn Ser Phe Pro Trp Thr
1               5                   10

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ile Ser Ser Ser Gly Ser Thr Ile
1               5

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 48

Cys Ala Arg Asp Thr Asn Trp Ala Phe Asp Tyr
1               5                   10

<210> SEQ ID NO 49
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gln Ser Val Phe Tyr Ser Ala Asn Asn Lys Asn Tyr
1               5                   10

<210> SEQ ID NO 50
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Trp Thr Ser
1

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Cys Gln Gln Phe Tyr Ser Thr Pro Arg Thr
1               5                   10

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gly Gly Ser Ile Ser Ser Asn Asn Trp
1               5

<210> SEQ ID NO 53
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ile Tyr His Asp Gly Thr Thr
1               5
```

```
<210> SEQ ID NO 54
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Cys Ala Arg Gly Asp Trp Gly Ser Gly Ala Phe Asp Ile
1               5                   10

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Cys Leu Gln Asp Tyr Asn Tyr Pro Arg Thr
1               5                   10

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ile Ser Ser Ser Ser Ser Thr Ile
1               5

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln Ser Val Phe Tyr Ser Ser Asn Asn Lys Asn Tyr
1               5                   10

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Phe Thr Phe Arg Asp Tyr Tyr
1               5

<210> SEQ ID NO 59
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 59

Ile Ser Ser Ser Gly Ser Ile Ile
1               5

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Cys Ala Arg Asp Thr Asn Trp Ala Leu Asp Tyr
1               5                   10

<210> SEQ ID NO 61
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Phe Thr Phe Ser Ser His Val
1               5

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ile Ser Gly Ser Gly Val Asp Thr
1               5

<210> SEQ ID NO 63
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Phe Thr Phe Ser Ser Tyr Trp
1               5

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 64

Ile Lys Gln Asp Gly Ser Glu Lys
1               5

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Cys Ala Arg Asp Thr Asn Trp Gly Phe Asp Asn
1               5                   10

<210> SEQ ID NO 66
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Gly Ser Ile Ser Ser Ser Asn Trp
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ile Phe His Asp Gly Thr Thr
1               5

<210> SEQ ID NO 68
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Cys Ala Arg Gly Asn Trp Gly Ser Gly Ala Leu Asp Ile
1               5                   10

<210> SEQ ID NO 69
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Phe Thr Phe Ser Ser Phe Val
1               5
```

-continued

```
<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ile Ser Gly Gly Gly Gly Ser Thr
1               5

<210> SEQ ID NO 71
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Cys Ala Lys Asp Trp Asp Leu Tyr Tyr Phe Asp Tyr
1               5                   10

<210> SEQ ID NO 72
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gln Gly Ile Ser Asn Trp
1               5

<210> SEQ ID NO 73
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Cys Gln Gln Ala Asn Ser Phe Pro Leu Thr
1               5                   10

<210> SEQ ID NO 74
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Phe Thr Phe Ser Asp Tyr Trp
1               5

<210> SEQ ID NO 75
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 75

Ile Lys Glu Asp Gly Asn Glu Lys
1               5

<210> SEQ ID NO 76
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Cys Ala Arg Asp Thr Asn Trp Gly Ser Asp Tyr
1               5                   10

<210> SEQ ID NO 77
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Val Trp Val
        35                  40                  45

Ser Thr Ile Thr Gly Gly Gly Thr Thr Ser Tyr Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Ala Lys Trp Gly Ser Trp Ser Ala Gly Ala Phe Asp Ile Trp Gly Gln
            100                 105                 110

Gly Thr Thr Val Thr Val Ser Ser
        115                 120

<210> SEQ ID NO 78
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30
```

```
Asn Trp Trp Ser Trp Val Arg Gln Pro Pro Gly Lys Gly Leu Glu Trp
            35                  40                  45
Ile Gly Glu Ile Tyr His Asp Gly Thr Thr Thr Tyr Asn Pro Ser Leu
 50                  55                  60
Lys Ser Arg Val Thr Ile Ser Val Asp Lys Ser Arg Asn Gln Phe Ser
 65                  70                  75                  80
Leu Lys Met Ser Ser Val Thr Ala Ala Asp Thr Ala Val Tyr Tyr Cys
                85                  90                  95
Ala Arg Gly Asp Trp Gly Ser Gly Ala Phe Asp Ile Trp Gly Gln Gly
            100                 105                 110
Thr Met Val Thr Val Ser Ser
        115

<210> SEQ ID NO 79
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Gln Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Arg Asp Tyr
            20                  25                  30
Tyr Met Ser Trp Ile Arg Gln Ala Pro Gly Lys Gly Leu Glu Trp Val
            35                  40                  45
Ser His Ile Ser Ser Gly Ser Ile Ile Asp Tyr Val Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Arg Asp Thr Asn Trp Ala Leu Asp Tyr Trp Gly Gln Gly Thr Leu
            100                 105                 110
Val Thr Val Ser Ser
        115

<210> SEQ ID NO 80
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser His
            20                  25                  30
Val Met Asn Trp Val Arg Gln Ala Pro Gly Lys Gly Leu Glu Trp Val
            35                  40                  45
Ala Thr Ile Ser Gly Ser Gly Val Asp Thr Tyr Tyr Ala Asp Ser Val
 50                  55                  60
```

```
Lys Gly Arg Phe Thr Ile Ser Arg Gly Asn Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Lys Trp Gly Ser Trp Ser Ala Gly Ala Phe Asp Ile Trp Gly Gln
            100                 105                 110

Gly Thr Met Val Thr Val Ser Ser
            115                 120
```

<210> SEQ ID NO 81
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Asn Trp Gly Phe Asp Asn Trp Gly Gln Gly Thr Leu
             100                 105                 110

Val Thr Val Ser Ser
         115
```

<210> SEQ ID NO 82
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Lys Lys Gly Leu Glu Trp
             35                  40                  45

Val Gly Glu Ile Phe His Asp Gly Thr Thr Ser Tyr Asn Pro Ser Leu
         50                  55                  60

Lys Ser Arg Val Thr Met Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95
```

Ala Arg Gly Asn Trp Gly Ser Gly Ala Leu Asp Ile Trp Gly Pro Gly
            100                 105                 110

Thr Met Val Thr Val Ser Ser
        115

<210> SEQ ID NO 83
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Trp Gly Ser Asp Tyr Trp Gly Gln Gly Thr Leu
            100                 105                 110

Val Thr Val Ser Ser
        115

<210> SEQ ID NO 84
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Phe Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys

```
<210> SEQ ID NO 85
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105

<210> SEQ ID NO 86
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 87
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ala Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Ser Gly Val
65              70                  75                  80

Ile Ser Ser Leu Gln Ala Glu Asp Val Ala Val Tyr Cys Gln Gln
                85                  90                  95

Phe Tyr Ser Thr Pro Arg Thr Phe Gly Gln Gly Thr Lys Val Glu Ile
                100                 105                 110

Lys

<210> SEQ ID NO 88
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 88

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
                100                 105

<210> SEQ ID NO 89
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Gly Gln
        35                  40                  45

```
Pro Pro Lys Leu Leu Ile Phe Trp Ala Ser Thr Arg Glu Ser Gly Val
        50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Phe Cys Gln Gln
                85                  90                  95
Phe Tyr Ser Thr Pro Arg Thr Phe Gly Gln Gly Thr Lys Val Glu Ile
               100                 105                 110
Lys
```

<210> SEQ ID NO 90
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Val Phe Tyr Ser
                20                  25                  30
Ser Asn Asn Lys Asn Tyr Leu Ala Trp Tyr Gln Gln Lys Pro Gly Gln
            35                  40                  45
Pro Pro Lys Leu Leu Ile Ser Trp Ala Ser Thr Arg Glu Ser Gly Val
        50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Gln
                85                  90                  95
Tyr Tyr Ser Thr Pro Tyr Thr Phe Gly Gln Gly Thr Lys Leu Glu Ile
               100                 105                 110
Lys
```

<210> SEQ ID NO 91
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
                20                  25                  30
Leu Ala Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
```

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 92
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Leu Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 93
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Ala Ile Gln Met Thr Gln Ser Pro Ser Pro Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 94
<211> LENGTH: 107
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 94

Asp Ile Gln Leu Thr Gln Ser Pro Ser Val Pro Ala Ser Val Gly
1               5                   10                  15

Asp Arg Val Thr Ile Thr Cys Arg Ala Ser Gln Gly Ile Ser Asn
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 95
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
                20                  25                  30

Ser Asn Asn Lys Asn Tyr Leu Leu Trp Tyr Gln Gln Lys Pro Gly Gln
            35                  40                  45

Pro Pro Lys Leu Leu Ile Phe Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 96
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 96

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Thr Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Asn Trp Gly Ser Asp Tyr Trp Gly Gln Gly Thr Leu
            100                 105                 110

Val Thr Val Ser Ser
        115
```

```
<210> SEQ ID NO 97
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Thr Gly Gly Gly Thr Thr Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Ser Trp Ser Ala Gly Ala Phe Asp Ile Trp Gly Gln
            100                 105                 110

Gly Thr Met Val Thr Val Ser Ser
        115                 120
```

```
<210> SEQ ID NO 98
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Asn Trp Ala Phe Asp Tyr Trp Gly Gln Gly Thr Leu
                100                 105                 110

Val Thr Val Ser Ser
        115

<210> SEQ ID NO 99
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Asn
                 20                  25                  30

Asn Trp Trp Ser Trp Val Arg Gln Pro Pro Gly Lys Gly Leu Glu Trp
            35                  40                  45

Ile Gly Glu Ile Tyr His Asp Gly Thr Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Asp Trp Gly Ser Gly Ala Phe Asp Ile Trp Gly Gln Gly
                100                 105                 110

Thr Met Val Thr Val Ser Ser
        115

<210> SEQ ID NO 100
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
 50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Asn Trp Ala Phe Asp Tyr Trp Gly Gln Gly Thr Leu
            100                 105                 110

Val Thr Val Ser Ser
            115

<210> SEQ ID NO 101
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Arg Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Ile Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Asn Trp Ala Leu Asp Tyr Trp Gly Gln Gly Thr Leu
            100                 105                 110

Val Thr Val Ser Ser
            115

<210> SEQ ID NO 102
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser His
                 20                  25                  30

Val Met Asn Trp Val Arg Gln Ala Pro Gly Lys Gly Leu Glu Trp Val
             35                  40                  45

Ser Ala Ile Ser Gly Ser Gly Val Asp Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Trp Gly Ser Trp Ser Ala Gly Ala Phe Asp Ile Trp Gly Gln
            100                 105                 110

Gly Thr Met Val Thr Val Ser Ser
        115                 120

<210> SEQ ID NO 103
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Phe His Asp Gly Thr Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Asn Trp Gly Ser Gly Ala Leu Asp Ile Trp Gly Gln Gly
            100                 105                 110

Thr Met Val Thr Val Ser Ser
        115

<210> SEQ ID NO 104
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Val Met Ser Trp Val Arg Gln Ala Pro Gly Lys Gly Leu Glu Trp Val
        35                  40                  45

Ser Ala Ile Ser Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Asp Leu Tyr Tyr Phe Asp Tyr Trp Gly Gln Gly Thr
            100                 105                 110

Leu Val Thr Val Ser Ser
        115

-continued

```
<210> SEQ ID NO 105
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Trp Gly Ser Asp Tyr Trp Gly Gln Gly Thr Leu
            100                 105                 110

Val Thr Val Ser Ser
        115

<210> SEQ ID NO 106
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys

<210> SEQ ID NO 107
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Tyr Pro Trp
                85                  90                  95

Thr Phe Gly Gln Gly Thr Lys Val Glu Ile Lys
            100                 105

<210> SEQ ID NO 108
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ala Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Thr Pro Arg Thr Phe Gly Gln Gly Thr Lys Val Glu Ile
            100                 105                 110

Lys

<210> SEQ ID NO 109
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Thr Pro Arg Thr Phe Gly Gln Gly Thr Lys Val Glu Ile
            100                 105                 110

Lys

<210> SEQ ID NO 110
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 111
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 112
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 113
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Asp Ile Gln Leu Thr Gln Ser Pro Ser Ser Val Pro Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 114
<211> LENGTH: 113
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 114

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 115
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Gly Gly Gly Gly Ser Gly Gly Gly Gly Ser Gly Gly Gly Gly Ser
1               5                   10                  15
```

US 11,359,018 B2

ANTI-PD-1 ANTIBODIES AND COMPOSITIONS

CROSS-REFERENCE TO RELATED APPLICATIONS

This application is a national stage application under 35 U.S.C. § 371 of International Patent Application No. PCT/EP2017/079615, filed Nov. 17, 2017, which claims priority from U.S. Provisional Patent Application 62/424,163, filed Nov. 18, 2016. The disclosures of those applications are incorporated by reference herein in their entirety.

SEQUENCE LISTING

The instant application contains a Sequence Listing which has been submitted electronically in ASCII format and is hereby incorporated by reference in its entirety. The electronic copy of the Sequence Listing, created on Nov. 13, 2017, is named 022675_W0056_SL.txt and is 99,158 bytes in size.

BACKGROUND OF THE INVENTION

PD-1, also known as Programmed Cell Death Protein 1 and CD279, is a 268 amino acid cell surface receptor that belongs to the immunoglobulin superfamily. PD-1 is a member of the CD28 family of T cell regulators and is expressed on T cells, B cells and macrophages. It binds ligands PD-L1 (also known as B7 homolog) and PD-L2 (also known as B7-DC).

PD-1 is a type I membrane protein whose structure includes an extracellular IgV domain, a transmembrane region and an intracellular tail containing two phosphorylation sites. Known as an immune checkpoint protein, PD-1 functions as an inducible immune modulatory receptor, playing a role in, e.g., negative regulation of T cell responses to antigen stimulation.

PD-L1 is the predominant ligand for PD-1. Binding of PD-L1 to PD-1 inhibits T cell activity, reducing cytokine production and suppressing T cell proliferation. Cancer cells that express PD-L1 are able to exploit this mechanism to inactivate the anti-tumor activity of T cells via binding of PD-L1 to the PD-1 receptor.

In view of its immune response regulatory properties, PD-1 has been investigated as a potential target for immunotherapy, including treatment of cancer and autoimmune diseases. Two anti-PD-1 antibodies, pembrolizumab and nivolumab, have been approved in the United States and Europe for treating certain cancers.

In view of the critical role of PD-1 as an immune modulator, there is a need for new and improved immune therapies that target PD-1 receptor to treat cancers and certain disorders of the immune system.

SUMMARY OF THE INVENTION

The present invention is directed to novel recombinant antibodies targeting PD-1, as well as pharmaceutical compositions comprising one or more of these antibodies, and use of the antibodies and pharmaceutical compositions for enhancing immunity in a patient, and for treatment of cancers originating from tissues such as skin, lung, intestine, colon, ovary, brain, prostate, kidney, soft tissues, the hematopoietic system, head and neck, liver, bladder, breast, stomach, uterus and pancreas. Compared to currently available treatments for such cancers, including antibody treatments, it is contemplated that the antibodies of the invention may provide a superior clinical response either alone or in combination with another cancer therapeutic, such as an antibody targeting another immune checkpoint protein.

In one embodiment, the present invention provides an anti-PD-1 antibody or an antigen-binding portion thereof, wherein the antibody competes for binding to human PD-1 with, or binds to the same epitope of human PD-1 as, any one of antibodies 18040, 18049, 18098, 18113, 18201, 18247, 18250, 18325, 18366, 18400, 18413 and 18483.

In one embodiment, the anti-PD-1 antibody competes for binding to human PD-1 with an antibody whose heavy chain (H) CDR1-3 and light chain (L) CDR1-3 are the same as or derived from the H-CDR1-3 and L-CDR1-3 of antibody 18040, 18049, 18098, 18113, 18201, 18247, 18250, 18325, 18366, 18400, 18413, or 18483.

In one embodiment, the anti-PD-1 antibody binds to the same epitope of human PD-1 as an antibody whose heavy chain (H) CDR1-3 and light chain (L) CDR1-3 are the same as or derived from the H-CDR1-3 and L-CDR1-3 of antibody 18040, 18049, 18098, 18113, 18201, 18247, 18250, 18325, 18366, 18400, 18413, or 18483.

In one embodiment, the anti-PD-1 antibody comprises H-CDR1-3 comprising the H-CDR1-3 amino acid sequences, respectively, of antibody 18040, 18049, 18098, 18113, 18201, 18247, 18250, 18325, 18366, 18400, 18413, or 18483.

In one embodiment, the anti-PD-1 antibody has a heavy chain variable domain (VH) that is at least 90% (e.g., at least 92%, at least 95%, at least 98%, or at least 99%) identical in amino acid sequence to the VH domain of antibody 18040, 18049, 18098, 18113, 18201, 18247, 18250, 18325, 18366, 18400, 18413, or 18483.

In one embodiment, the anti-PD-1 antibody has a VH that comprises the VH amino acid sequence of antibody 18040, 18049, 18098, 18113, 18201, 18247, 18250, 18325, 18366, 18400, 18413, or 18483.

In one embodiment, the anti-PD-1 antibody has a heavy chain (HC) that comprises the VH amino acid sequence of antibody 18040, 18049, 18098, 18113, 18201, 18247, 18250, 18325, 18366, 18400, 18413, or 18483, and the heavy chain constant region amino acid sequence of SEQ ID NO: 26.

In one embodiment, the anti-PD-1 antibody comprises L-CDR1-3 comprising the L-CDR1-3 amino acid sequences, respectively, of antibody 18040, 18049, 18098, 18113, 18201, 18247, 18250, 18325, 18366, 18400, 18413, or 18483.

In one embodiment, the anti-PD-1 antibody has a light chain variable domain (VL) that is at least 90% (e.g, at least 92%, at least 95%, at least 98%, or at least 99%) identical in amino acid sequence to the VL domain of antibody 18040, 18049, 18098, 18113, 18201, 18247, 18250, 18325, 18366, 18400, 18413, or 18483.

In one embodiment, the anti-PD-1 antibody has a VL that comprises the VL amino acid sequence of antibody 18040, 18049, 18098, 18113, 18201, 18247, 18250, 18325, 18366, 18400, 18413, or 18483.

In one embodiment, the anti-PD-1 antibody has a light chain (LC) that comprises the VL amino acid sequence of antibody 18040, 18049, 18098, 18113, 18201, 18247, 18250, 18325, 18366, 18400, 18413, or 18483, and the light chain constant region amino acid sequence of SEQ ID NO: 28.

In one embodiment, the anti-PD-1 antibody comprises the H-CDR3 and L-CDR3 amino acid sequences of antibody 18040, 18049, 18098, 18113, 18201, 18247, 18250, 18325, 18366, 18400, 18413, or 18483.

In one embodiment, the anti-PD-1 antibody comprises the H-CDR1-3 and L-CDR1-3 amino acid sequences of antibody 18040, 18049, 18098, 18113, 18201, 18247, 18250, 18325, 18366, 18400, 18413, or 18483.

In one embodiment, the anti-PD-1 antibody has a VH and a VL that are at least 90% (e.g., at least 92%, at least 95%, at least 98%, or at least 99%) identical in amino acid sequence to the VH and VL, respectively, of antibody 18040, 18049, 18098, 18113, 18201, 18247, 18250, 18325, 18366, 18400, 18413, or 18483.

In one embodiment, the anti-PD-1 antibody has a VH and a VL that comprise or consist of the VH and VL amino acid sequences, respectively, of antibody 18040, 18049, 18098, 18113, 18201, 18247, 18250, 18325, 18366, 18400, 18413, or 18483.

In one embodiment, the anti-PD-1 antibody has an HC and an LC that comprise or consist of the HC and LC amino acid sequences, respectively, of antibody 18040, 18049, 18098, 18113, 18201, 18247, 18250, 18325, 18366, 18400, 18413, or 18483.

In one embodiment, the anti-PD-1 antibody has (1) an HC that comprises the VH amino acid sequence of an antibody selected from the group consisting of antibody 18040, 18049, 18098, 18113, 18201, 18247, 18250, 18325, 18366, 18400, 18413, and 18483, and the heavy chain constant region amino acid sequence of SEQ ID NO: 26; and (2) an LC that comprises the VL amino acid sequence of that selected antibody and the light chain constant region amino acid sequence of SEQ ID NO: 28.

In certain embodiments, the anti-PD-1 antibody or antigen-binding portion of the invention has at least one of the following properties:
a) binds to cynomolgus PD-1 with a $K_D$ of, for example, $4 \times 10^{-8}$ M or less;
b) binds to mouse PD-1 with a $K_D$ of, for example, $2 \times 10^{-8}$ M or less;
c) binds to human PD-1 with a $K_D$ of $3 \times 10^{-9}$ M or less;
d) inhibits the interaction of PD-1 with PD-L1 at a concentration of 10 µg/ml;
e) stimulates IL-2 production in an SEB whole blood assay; and
f) stimulates IFN-γ production in a one-way mixed lymphocyte reaction assay.
Examples of such an antibody include, without limitation, antibodies 18040, 18049, 18098, 18113, 18247, 18250, 18325, 18366, 18413, and 18483 (having properties a) and c)-f)) and antibodies 18201 and 18400 (having properties a)-f)). In some embodiments, the anti-PD-1 antibody or antigen-binding portion of the invention has all of said properties.

In some embodiments, the anti-PD-1 antibody or antigen-binding portion of the invention competes for binding to human PD-1 with antibody 18366, 18250, 18040, 18247, 18113, and/or 18483. In some embodiments, the anti-PD-1 antibody or antigen-binding portion of the invention competes for binding to human PD-1 with antibody 12760 and/or 13112.

In certain embodiments, the anti-PD-1 antibody or antigen-binding portion of the invention does not compete for binding to PD-1 with pembrolizumab or nivolumab. In certain embodiments, the anti-PD-1 antibody or antigen-binding portion of the invention does not bind to the same epitope as pembrolizumab or nivolumab.

In another aspect, the present invention provides pharmaceutical compositions comprising at least one anti-PD-1 antibody or antigen-binding portion thereof as described herein and a pharmaceutically acceptable excipient, optionally with an additional therapeutic, such as an anti-cancer antibody therapeutic.

The present invention further provides isolated nucleic acid molecules comprising a nucleotide sequence that encodes the heavy chain or an antigen-binding portion thereof, a nucleotide sequence that encodes the light chain or an antigen-binding portion thereof, or both, of an anti-PD-1 antibody as described herein.

The present invention also provides vectors comprising such an isolated nucleic acid molecule, wherein said vector may further comprise an expression control sequence.

The present invention also provides host cells comprising a nucleotide sequence that encodes the heavy chain or an antigen-binding portion thereof, a nucleotide sequence that encodes the light chain or an antigen-binding portion thereof, or both, of an anti-PD-1 antibody as described herein.

The present invention also provides a method for producing an antibody or antigen-binding portion thereof as described herein, comprising providing a host cell that comprises a nucleotide sequence that encodes the heavy chain or an antigen-binding portion thereof and a nucleotide sequence that encodes the light chain or an antigen-binding portion thereof of an anti-PD-1 antibody as described herein, culturing said host cell under conditions suitable for expression of the antibody or portion, and isolating the resulting antibody or portion.

The present invention also provides a multi-specific (e.g., bi-specific) binding molecule having the binding specificity of an anti-PD-1 antibody described herein and the binding specificity of another, distinct antibody such as another anti-PD-1 antibody (e.g., as described herein) or an antibody that targets a different protein, such as another immune checkpoint protein, a cancer antigen, or another cell surface molecule whose activity mediates a disease condition such as cancer. In some embodiments, the multi-specific (e.g., bi-specific) binding molecule comprises the antigen-binding portions (e.g., the six CDRs) of the anti-PD-1 antibody and the other antibody.

The present invention also provides a method for enhancing immunity in a patient (e.g., a human patient), comprising administering to said patient an anti-PD-1 antibody or an antigen-binding portion thereof, a pharmaceutical composition, or a bi-specific binding molecule as described herein.

The present invention further provides a method for treating cancer in a patient (e.g., a human patient), comprising administering to said patient an anti-PD-1 antibody or an antigen-binding portion thereof, a pharmaceutical composition, or a bi-specific binding molecule as described herein. In some embodiments, the cancer originates in a tissue selected from skin, lung, intestine, colon, ovary, brain, prostate, kidney, soft tissues, hematopoietic system, head and neck, liver, bladder, breast, stomach, uterus and pancreas. The cancer may be, e.g., advanced or metastatic melanoma, non-small cell lung cancer, head and neck squamous cell cancer, bladder cancer, gastric cancer, renal cell carcinoma, hepatocellular carcinoma, colorectal cancer, or Hodgkin's lymphoma.

Any of the above methods may further comprise administration of, e.g., a chemotherapeutic agent, an anti-neoplastic agent, an anti-angiogenic agent, a tyrosine kinase inhibitor, a PD-1 pathway inhibitor, or radiation therapy.

The present invention further provides the use of an antibody composition comprising an anti-PD-1 antibody or antigen-binding portion as described herein for the manufacture of a medicament for treating cancer in a patient and/or enhancing immunity in a patient.

The present invention further provides an anti-PD-1 antibody or antigen-binding portion as described herein for use in treating cancer in a patient and/or enhancing immunity in a patient, e.g., in a treatment method described herein.

The present invention further provides an article of manufacture comprising an anti-PD-1 antibody or antigen-binding portion as described herein, wherein said article of manufacture is suitable for treating cancer in a patient and/or enhancing immunity in a patient, e.g., in a treatment method described herein.

DETAILED DESCRIPTION OF THE INVENTION

Figure 1A:
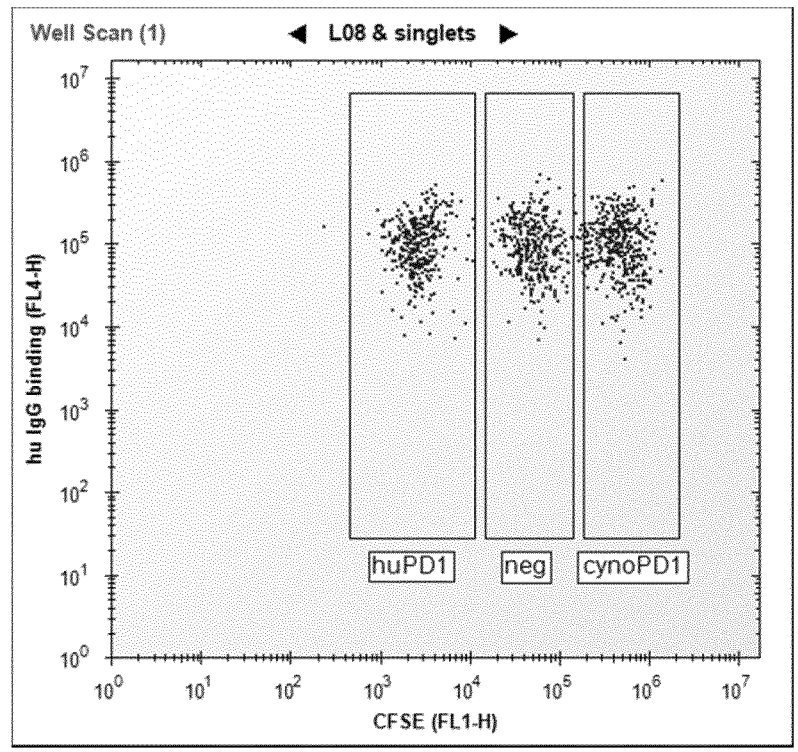
FIGS. 1A-1D show representative flow cytometry dot plots for four anti-PD-1 antibody clones exhibiting different reactivity towards PD-1 orthologs.
Figure 1A:
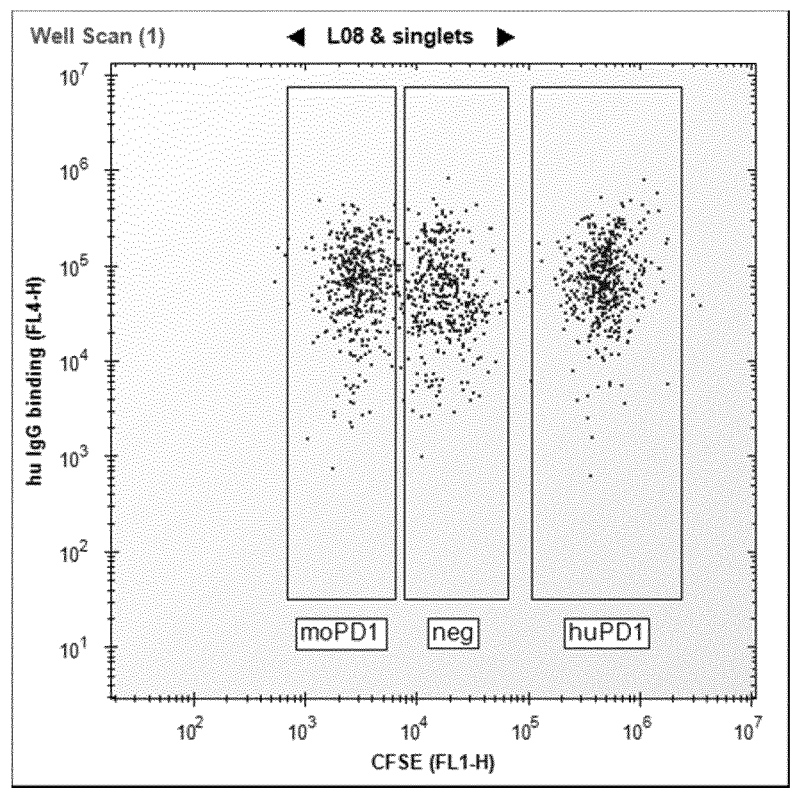
Figure 1B:
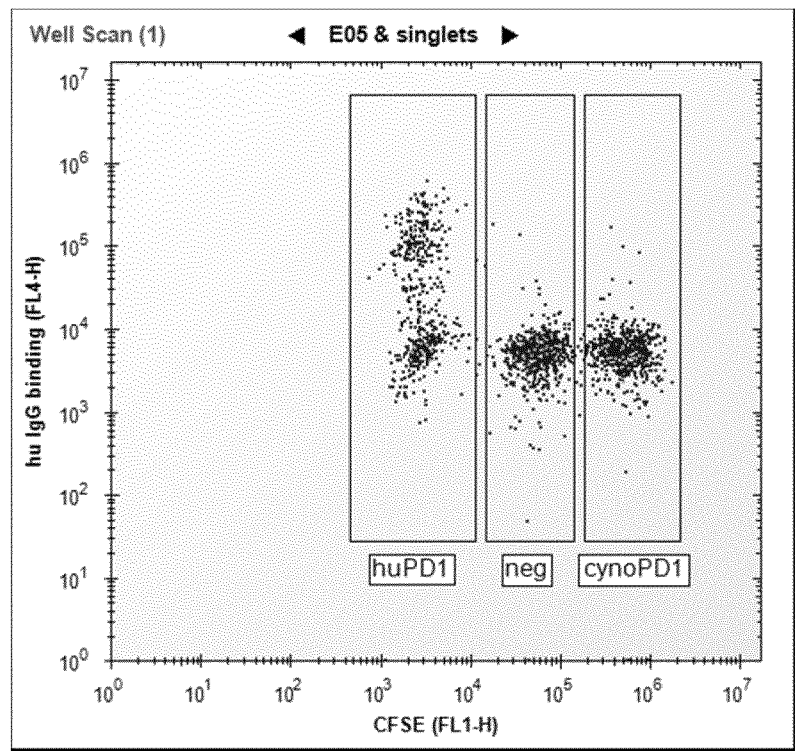
Figure 1B:
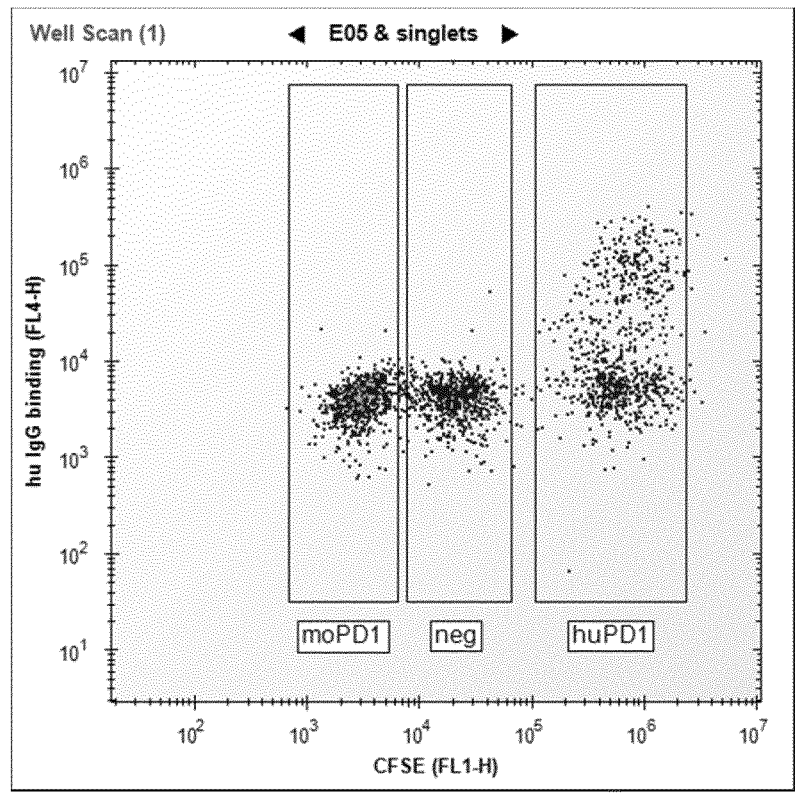
Figure 1C:
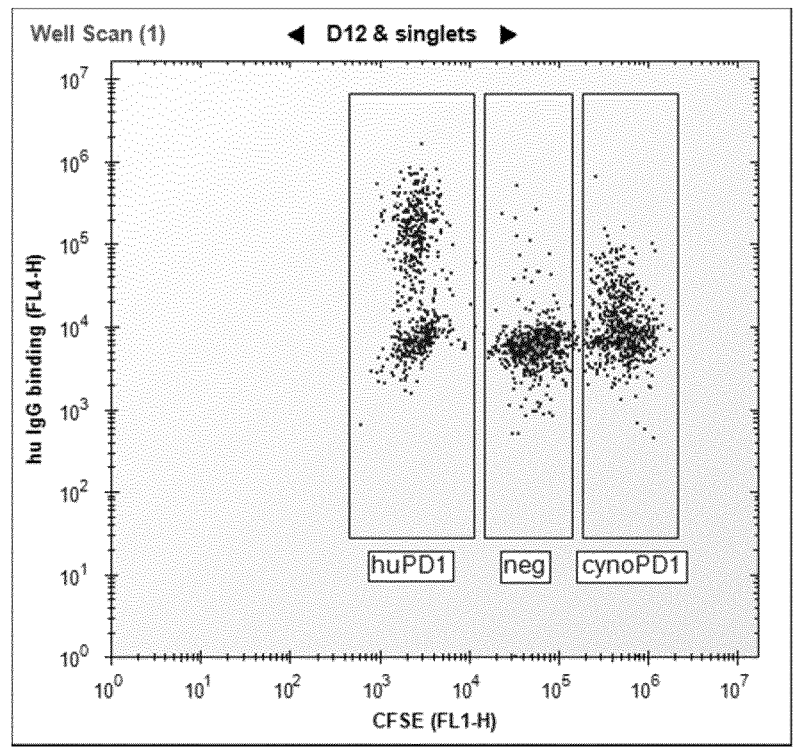
Figure 1C:
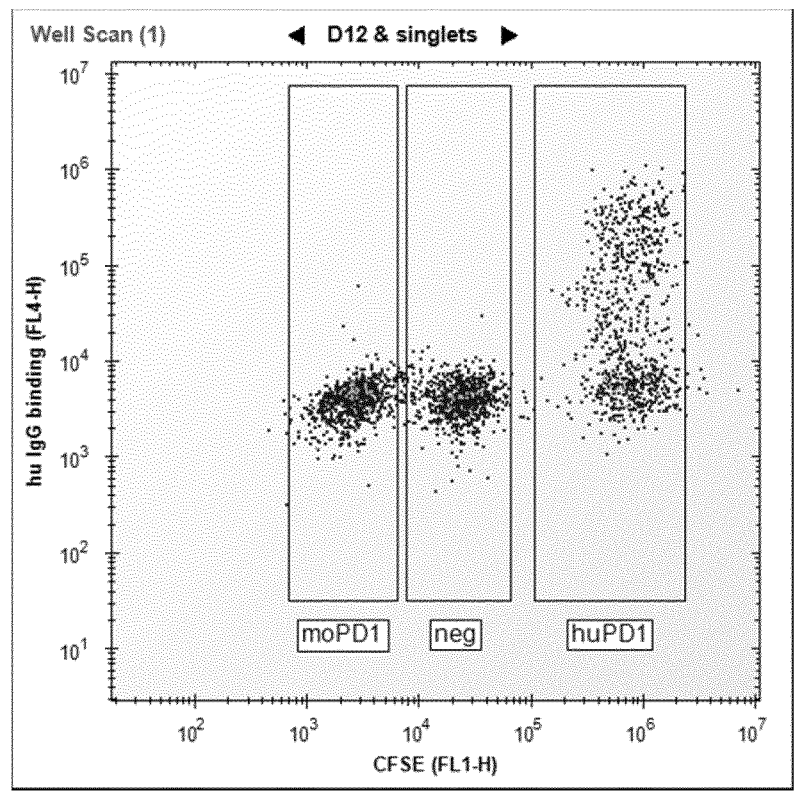
Figure 1D:
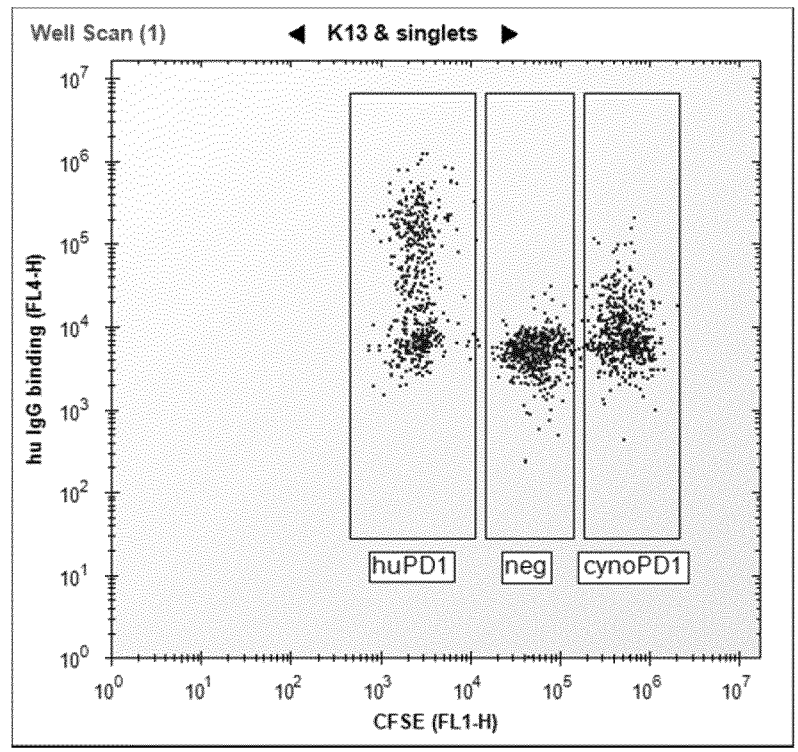
Figure 1D:
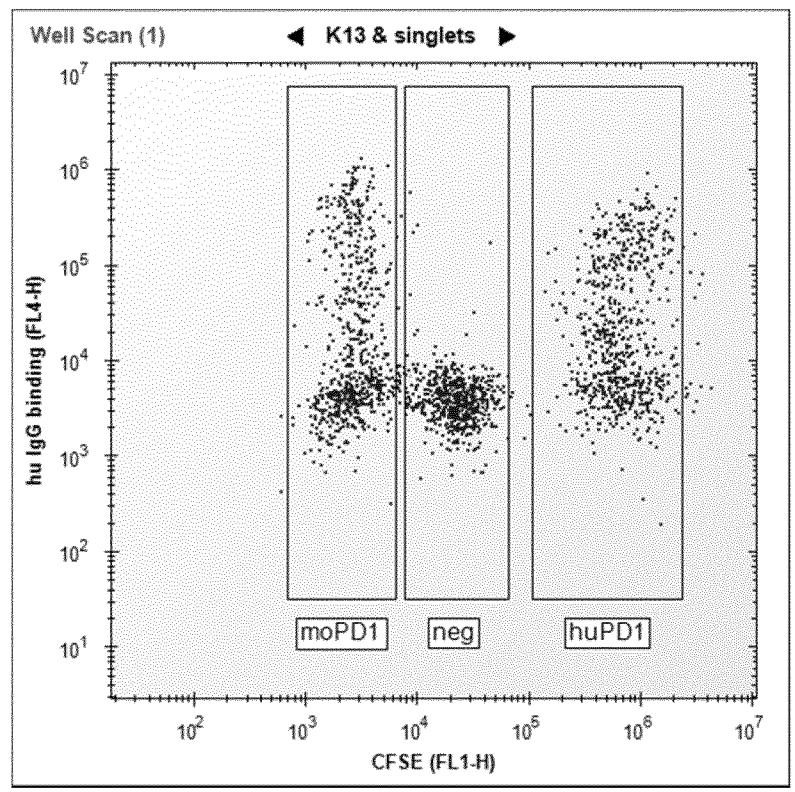
Figure 2A:
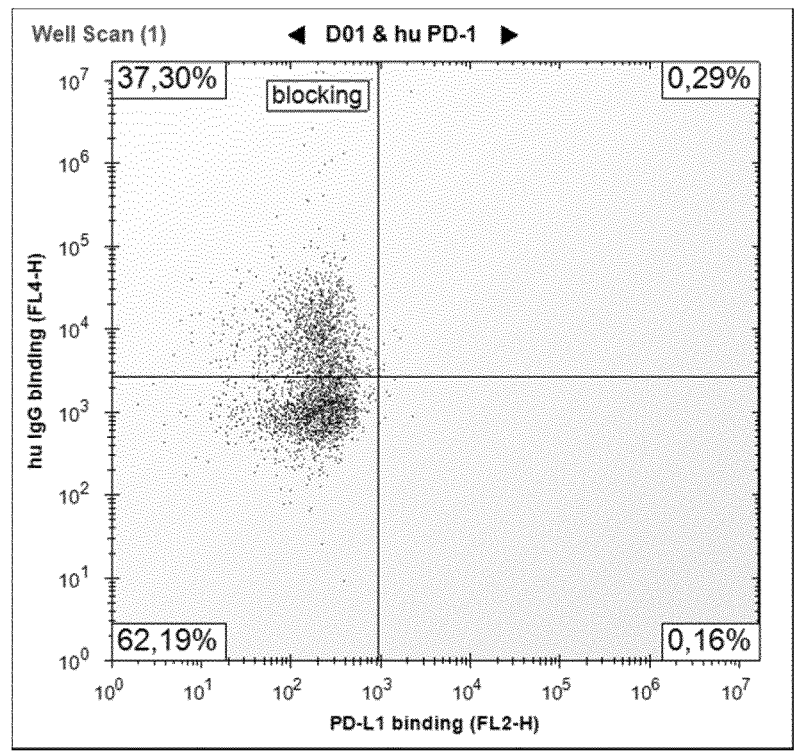
FIGS. 2A-2H show blocking of PD-L1-binding to cell-expressed PD-1 for anti-PD-1 antibodies of the invention.
Figure 2A:
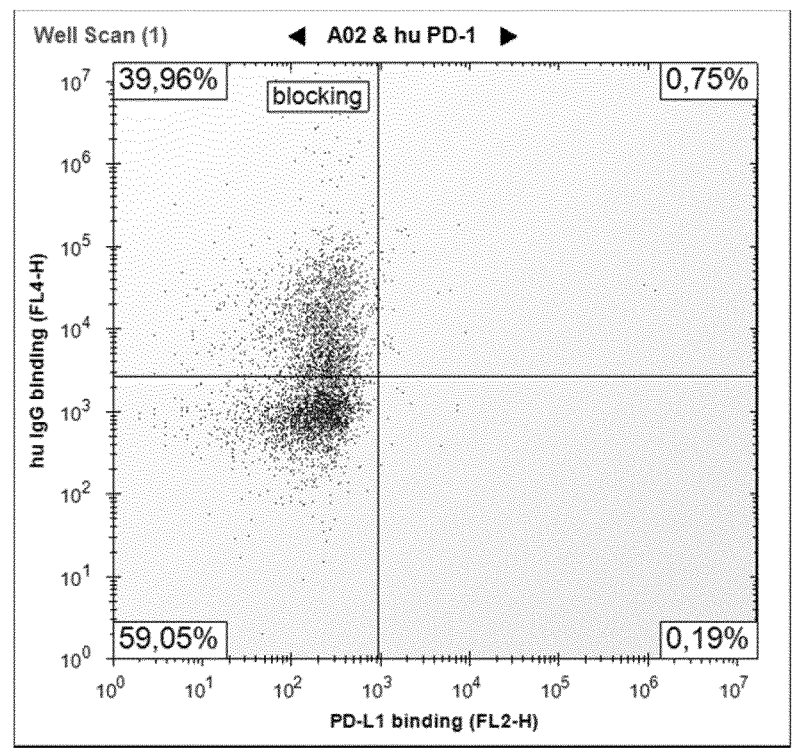
Figure 2B:
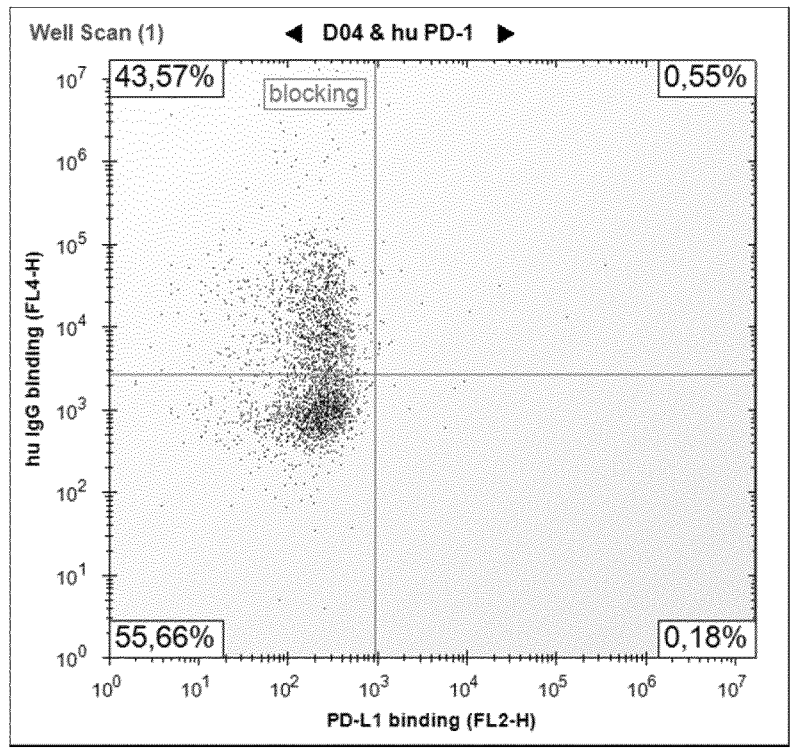
Figure 2B:
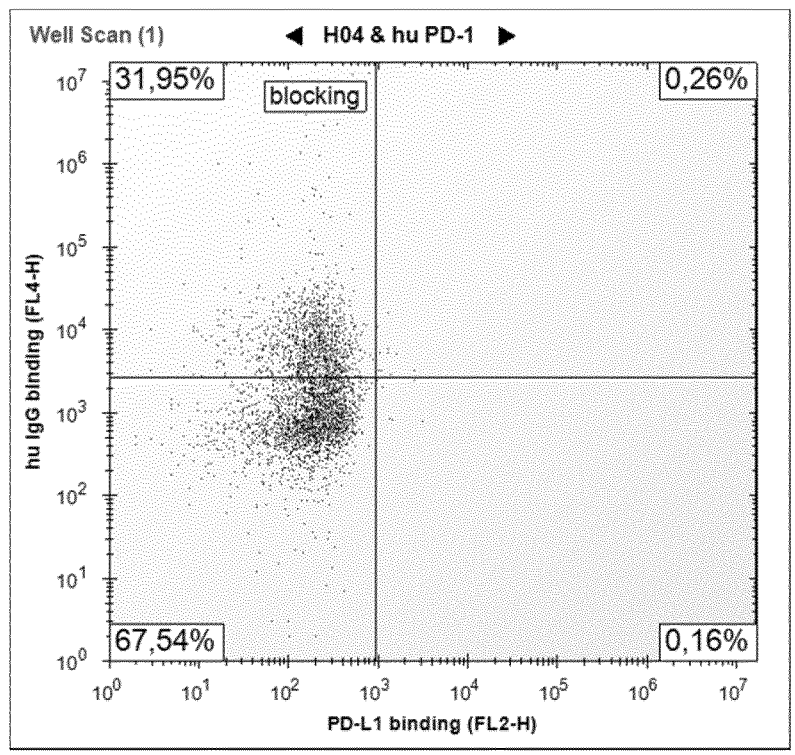
Figure 2C:
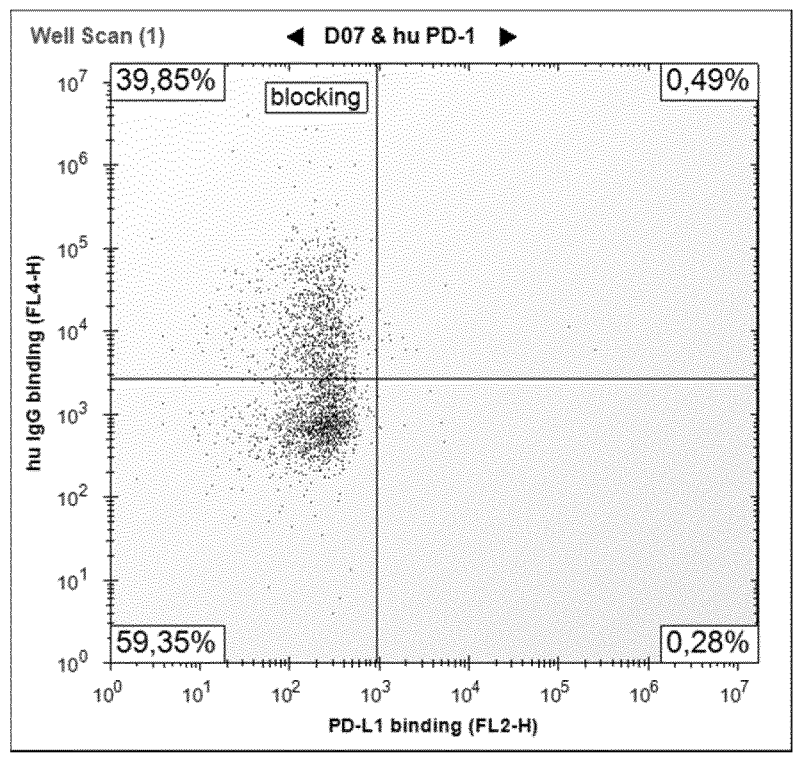
Figure 2C:
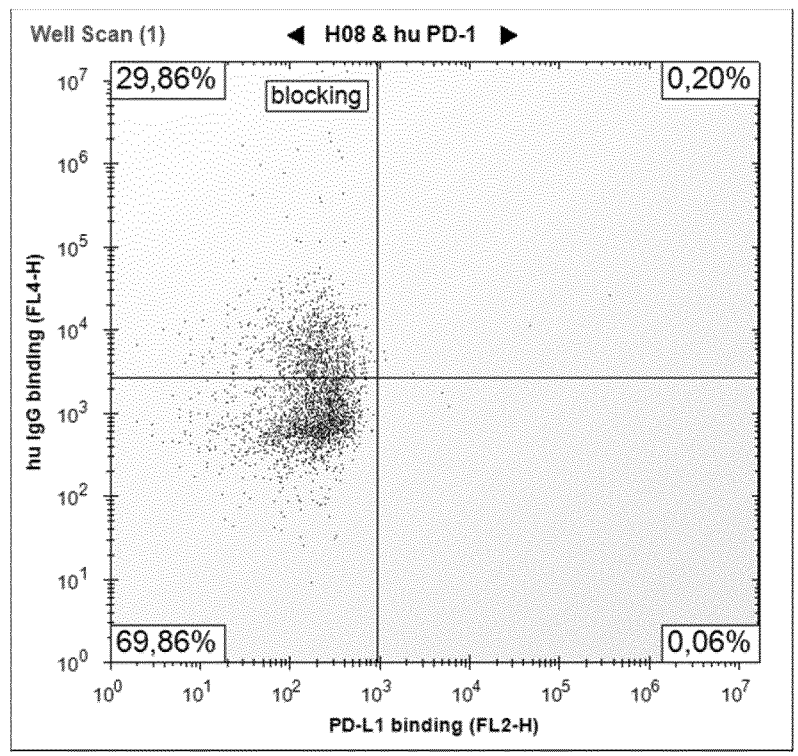
Figure 2D:
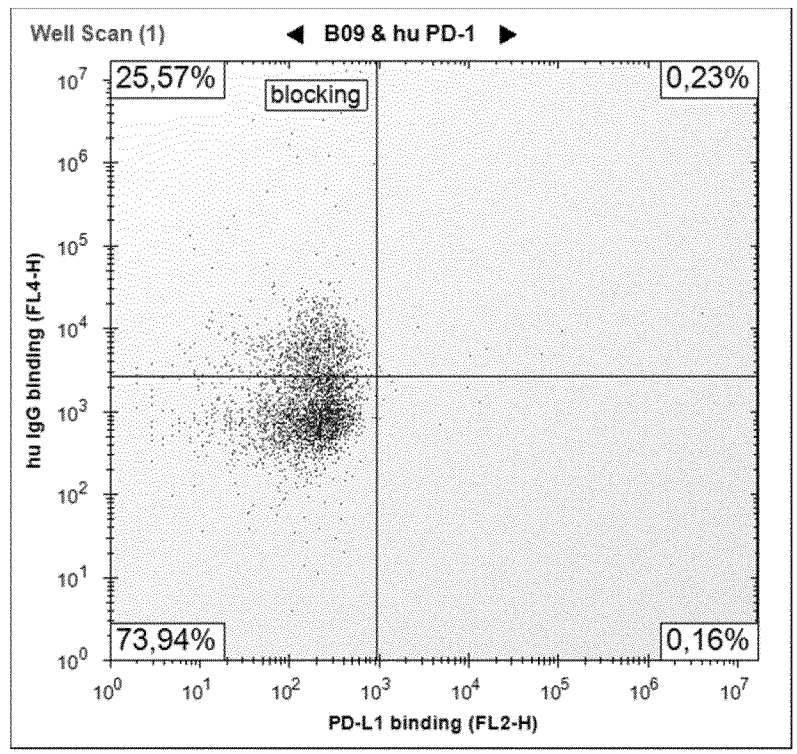
Figure 2D:
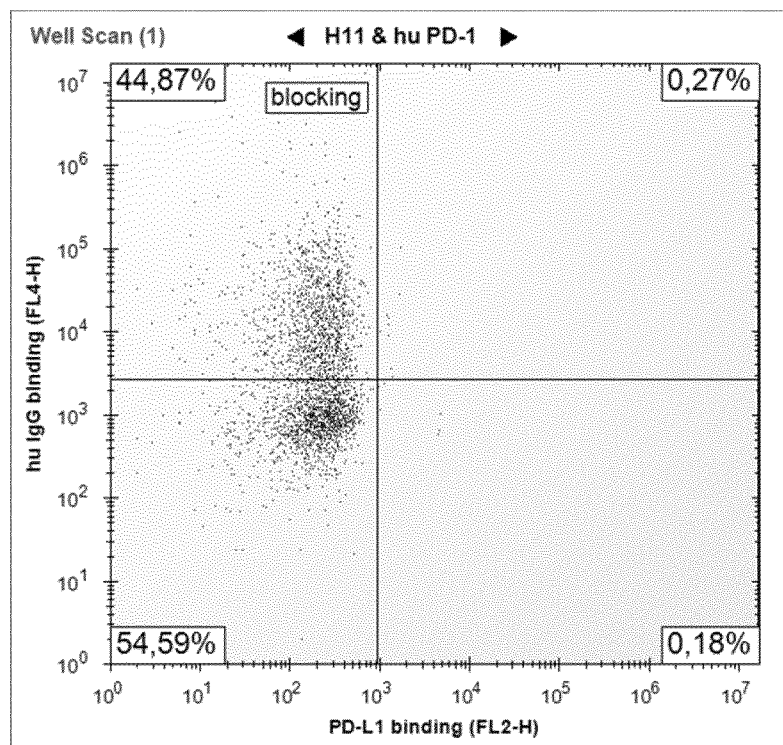
Figure 2E:
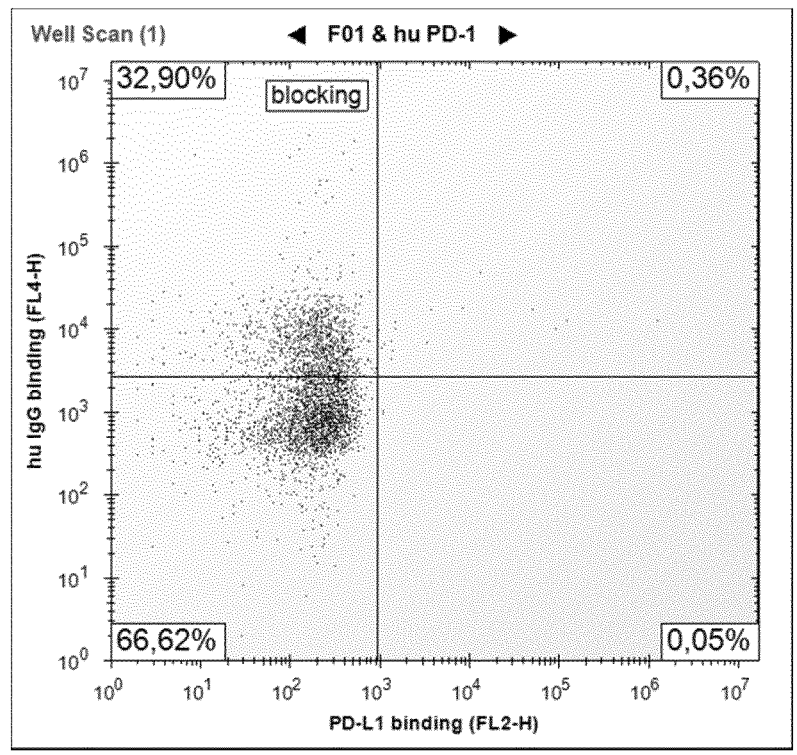
Figure 2E:
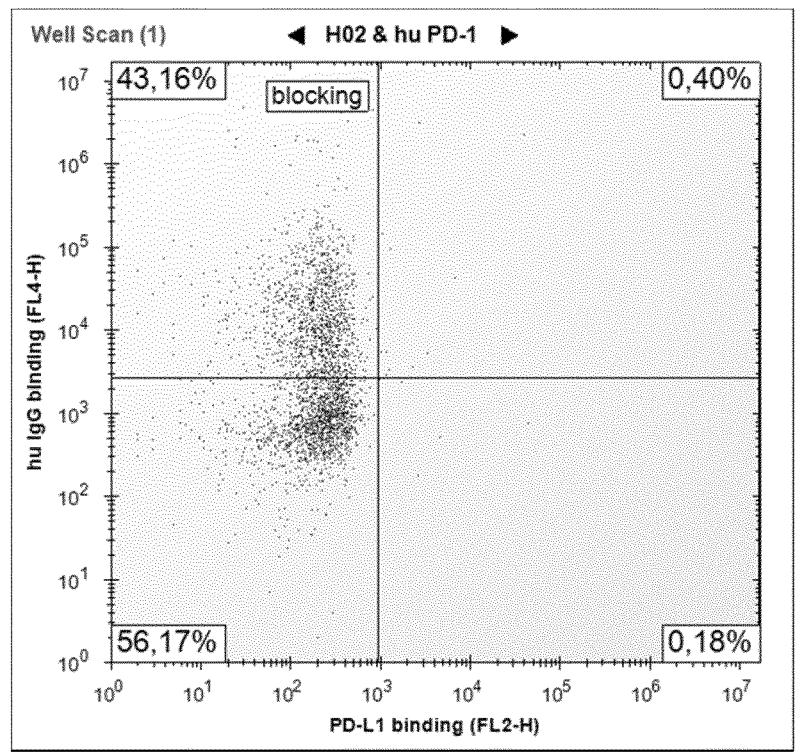
Figure 2F:
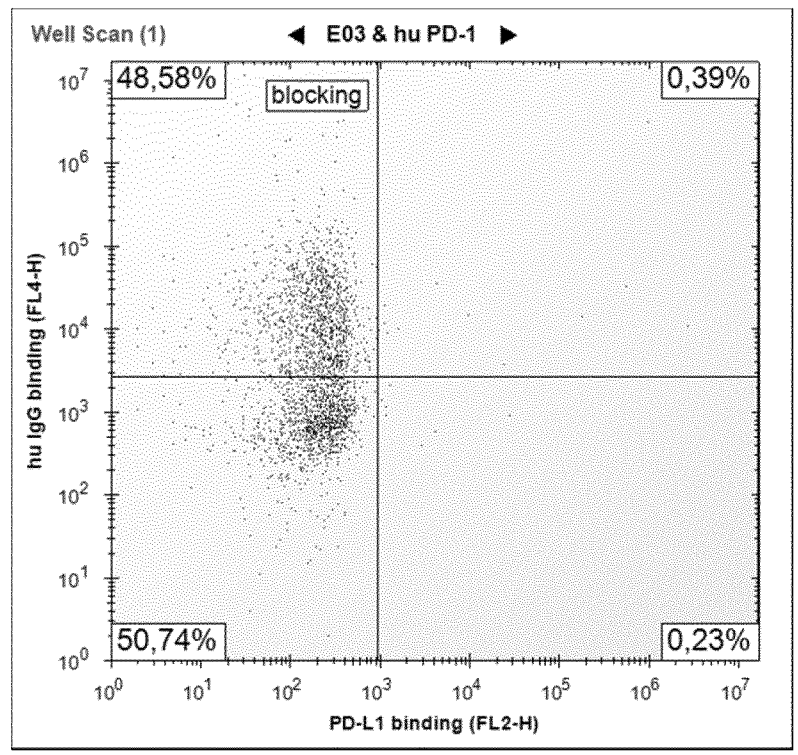
Figure 2F:
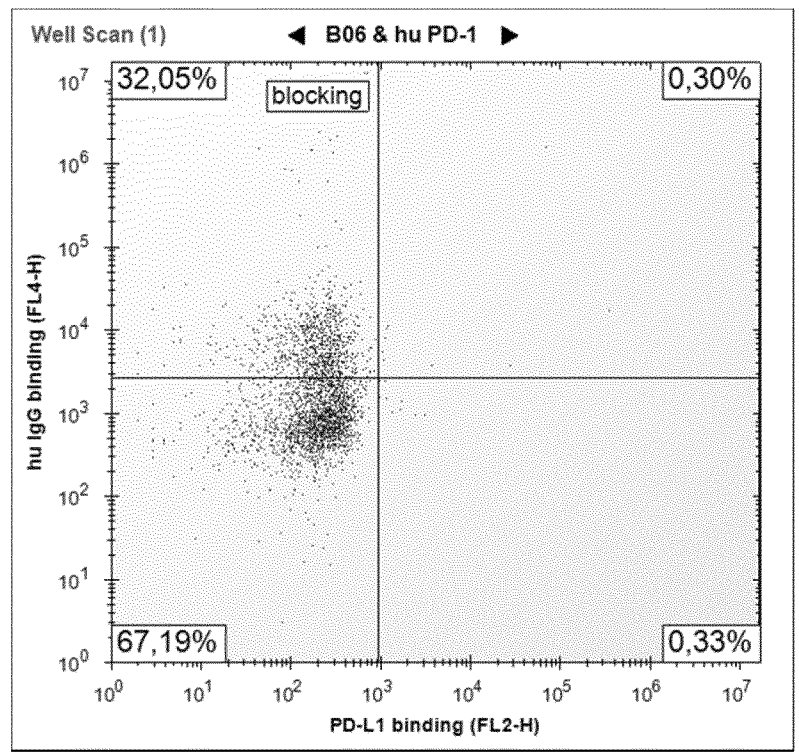
Figure 2G:
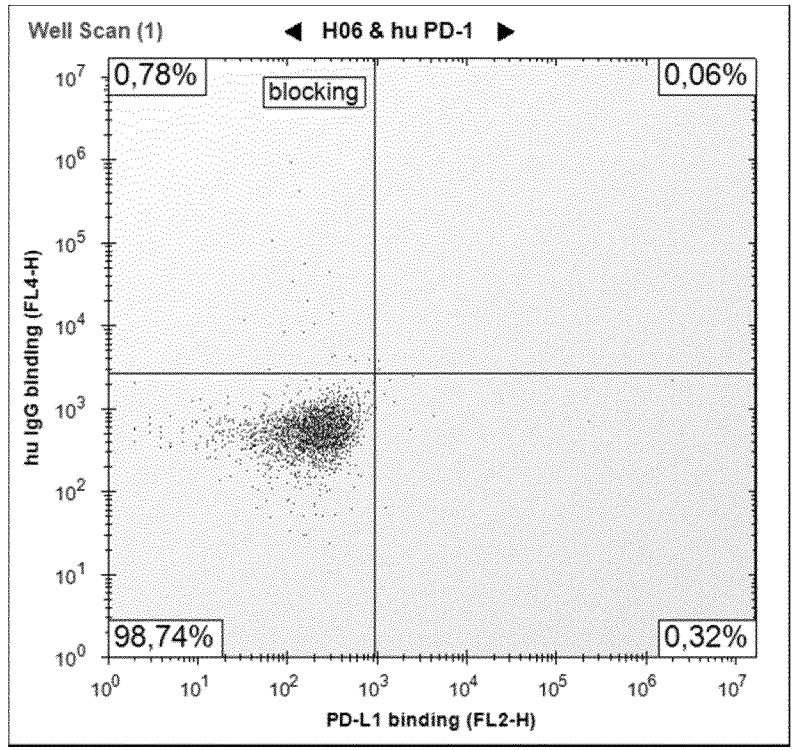
Figure 2G:
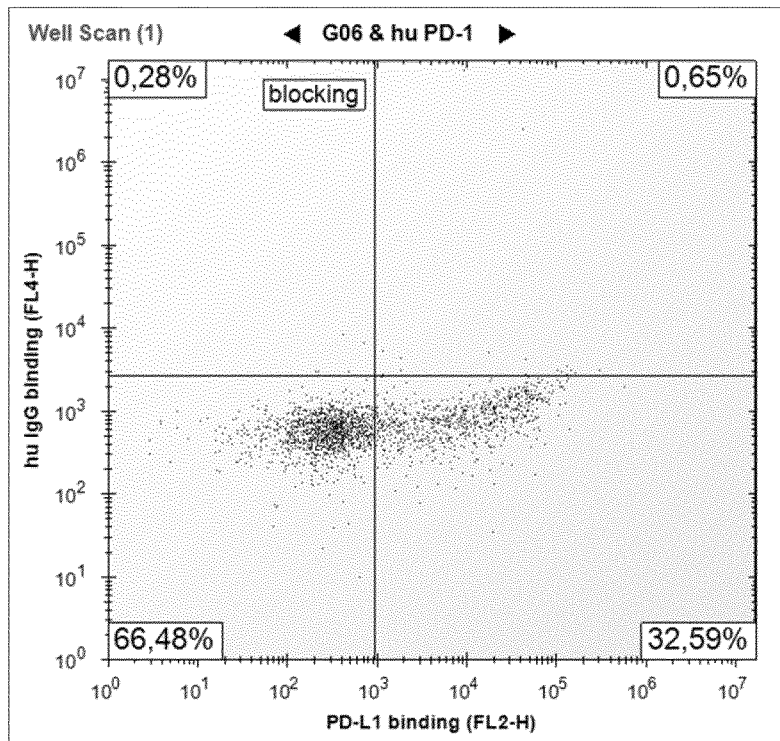
Figure 2H:
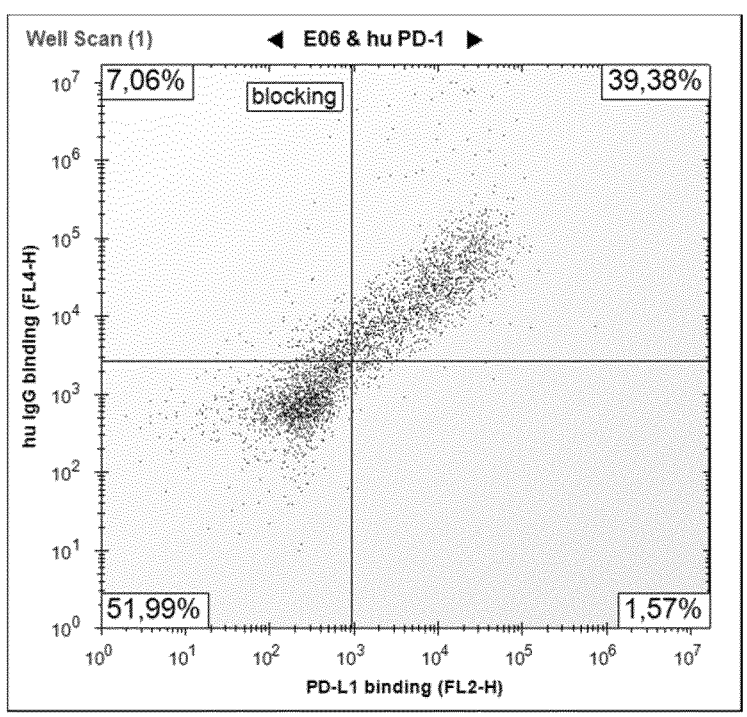
Figure 3A:
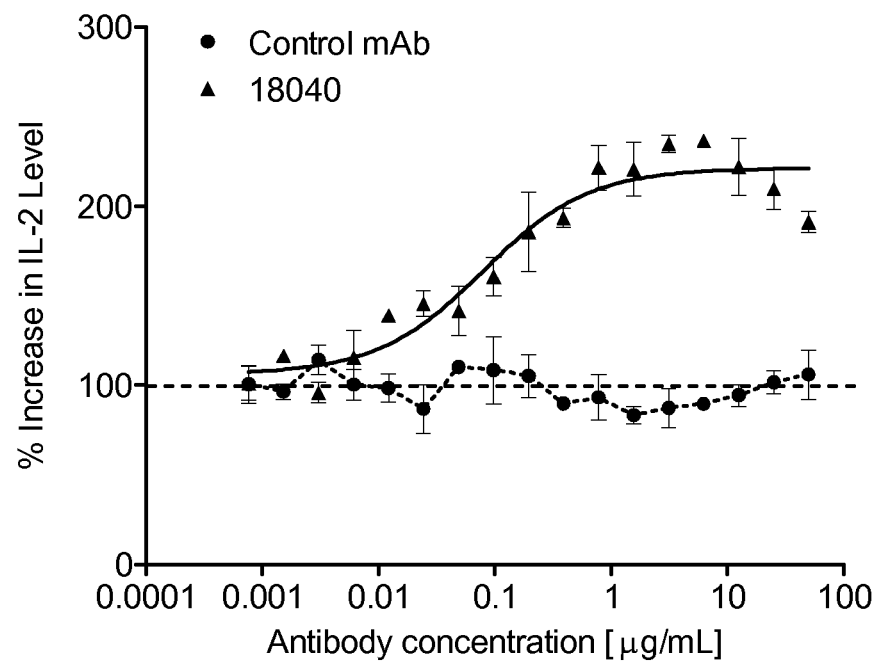
FIGS. 3A-3F show dose-response curves of twelve anti-PD-1 antibodies in the SEB whole blood assay.
Figure 3A:
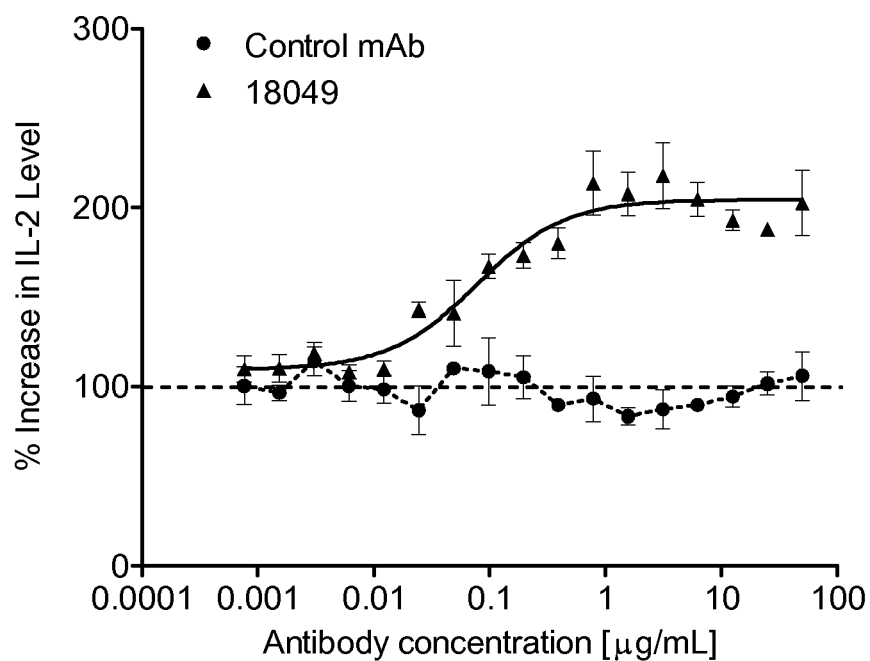
Figure 3B:
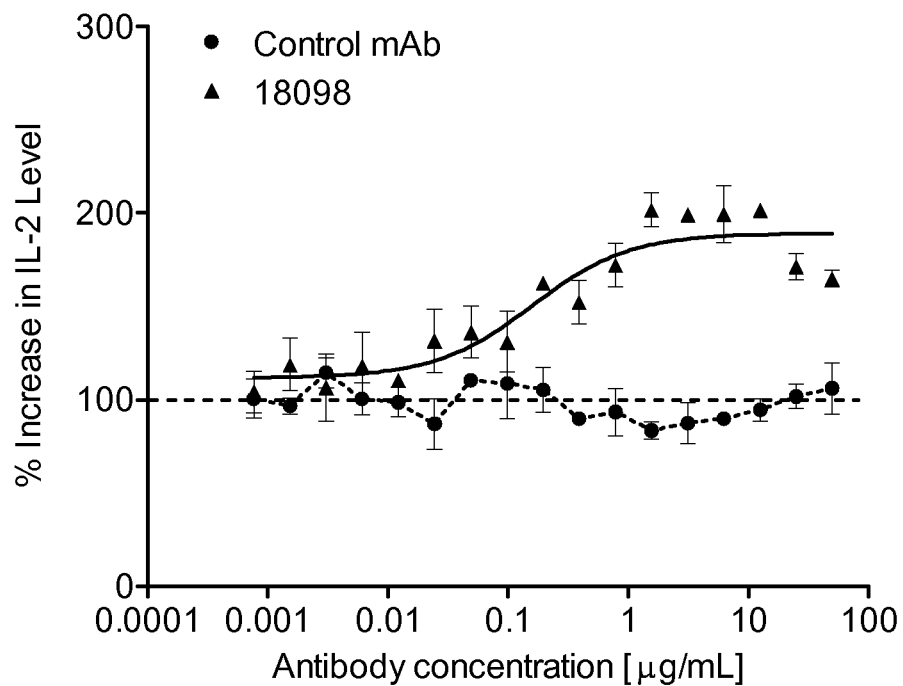
Figure 3B:
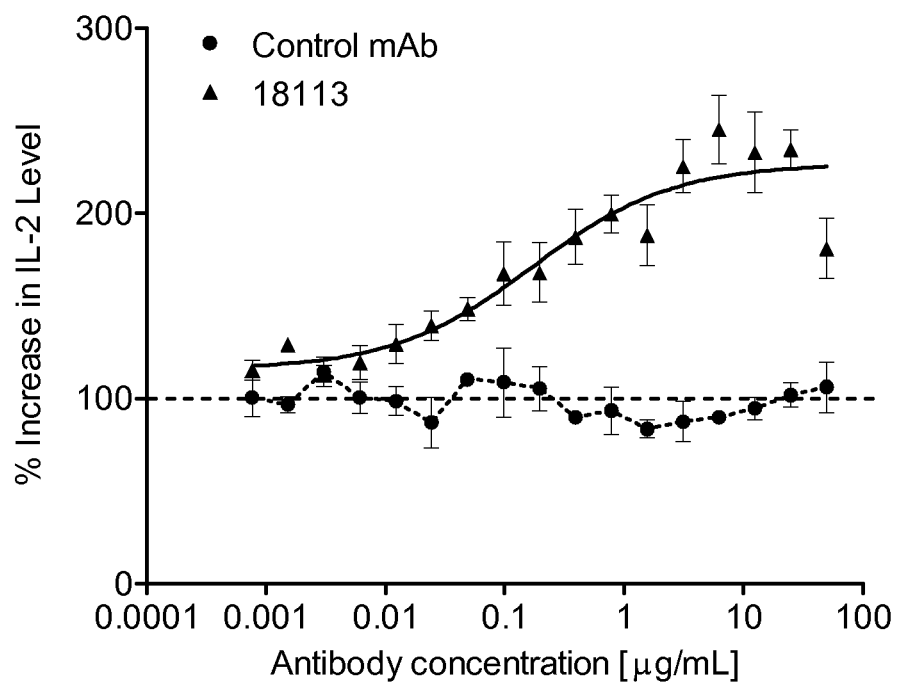
Figure 3C:
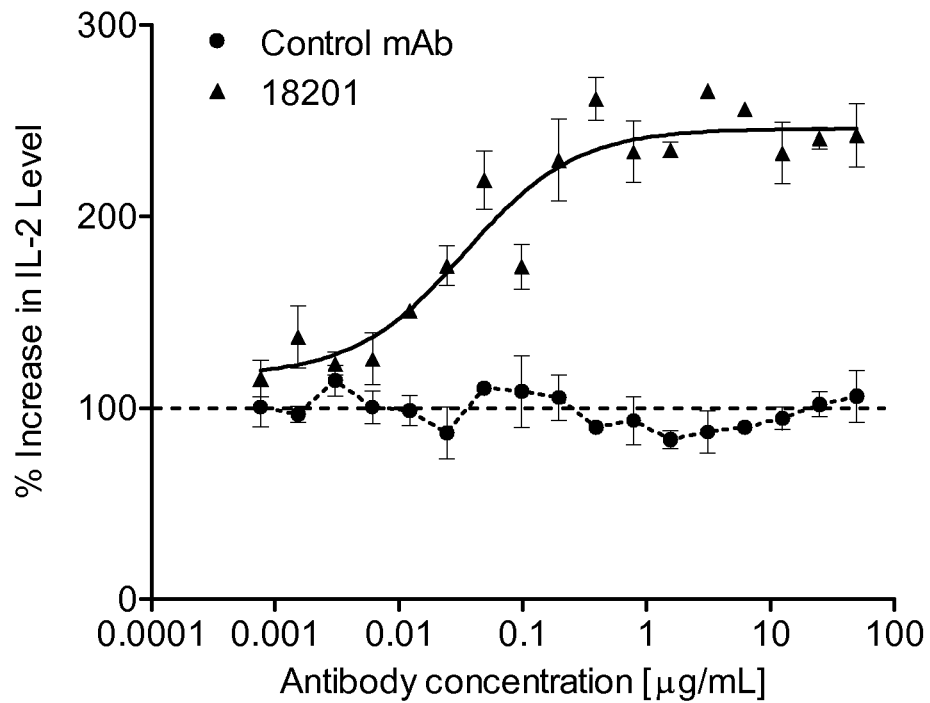
Figure 3C:
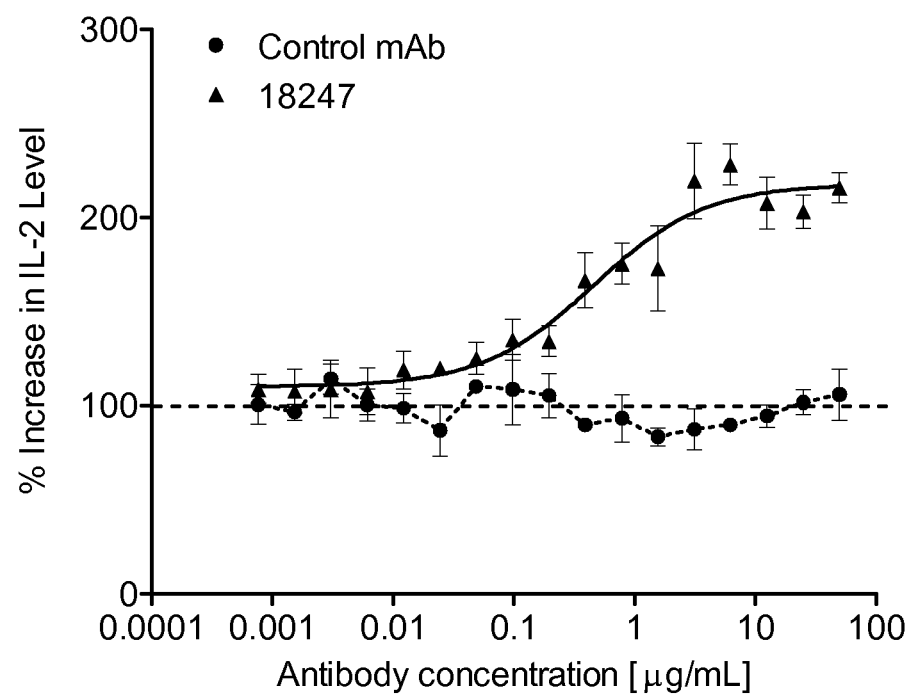
Figure 3D:
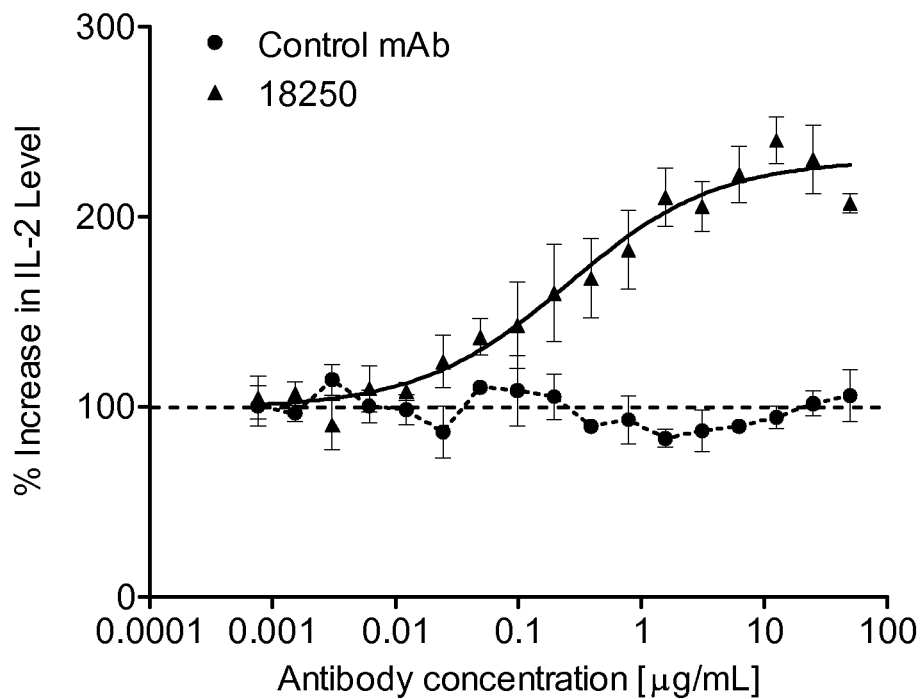
Figure 3D:
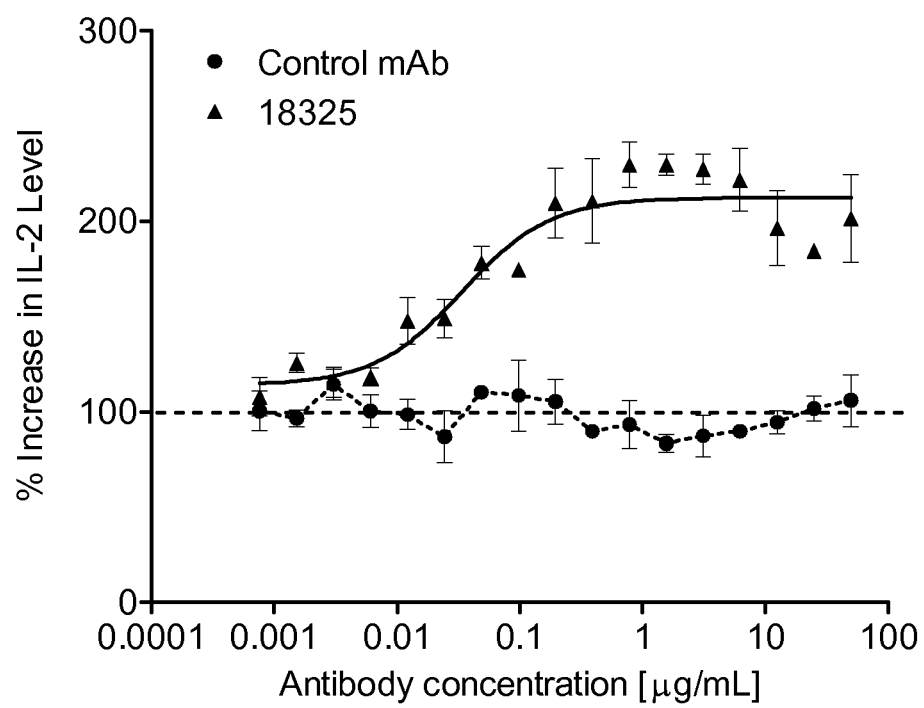
Figure 3E:
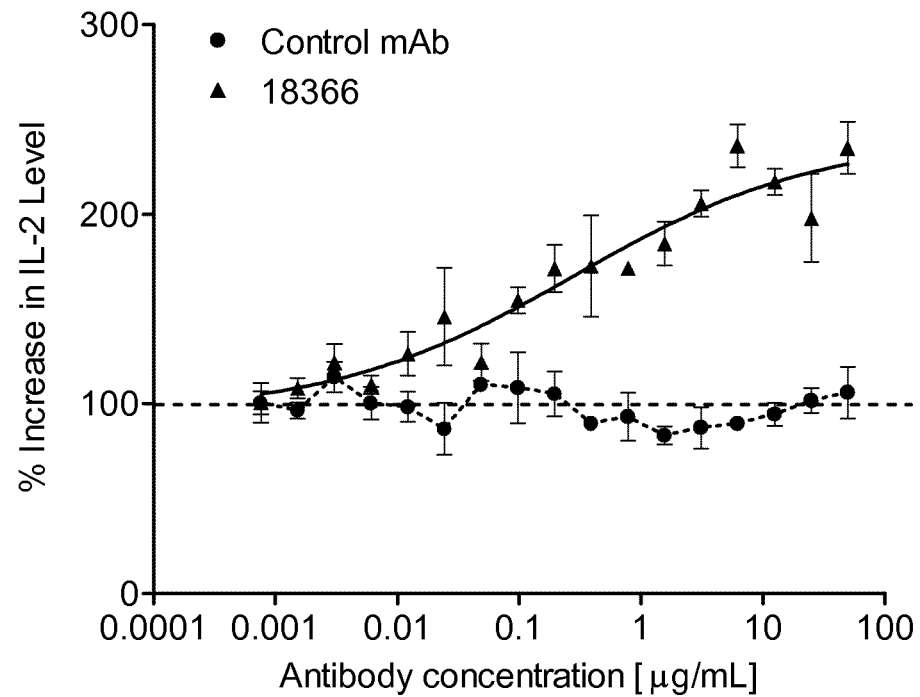
Figure 3E:
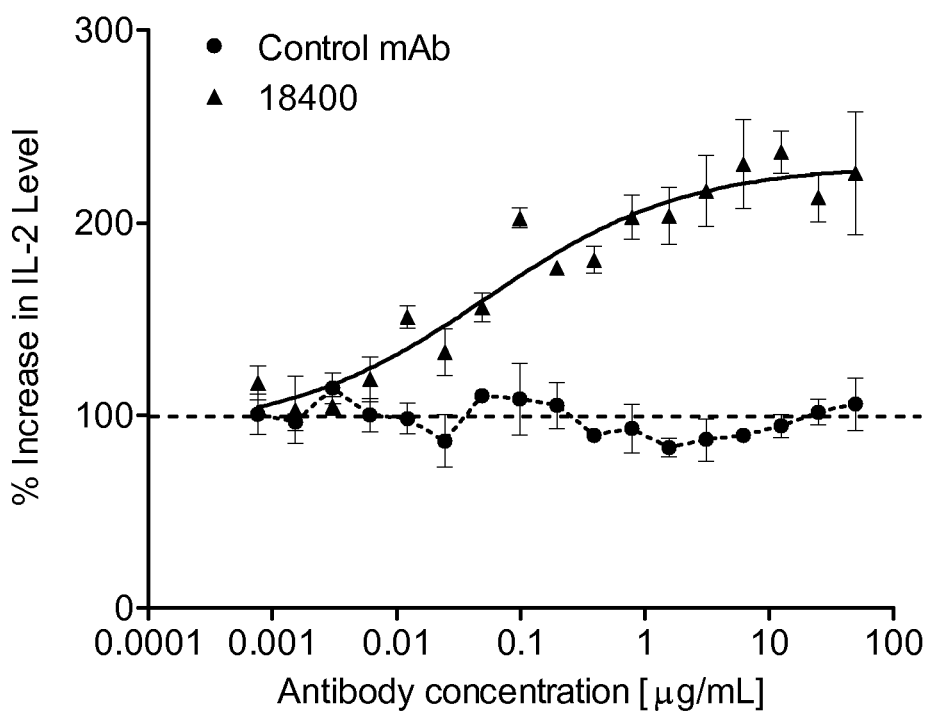
Figure 3F:
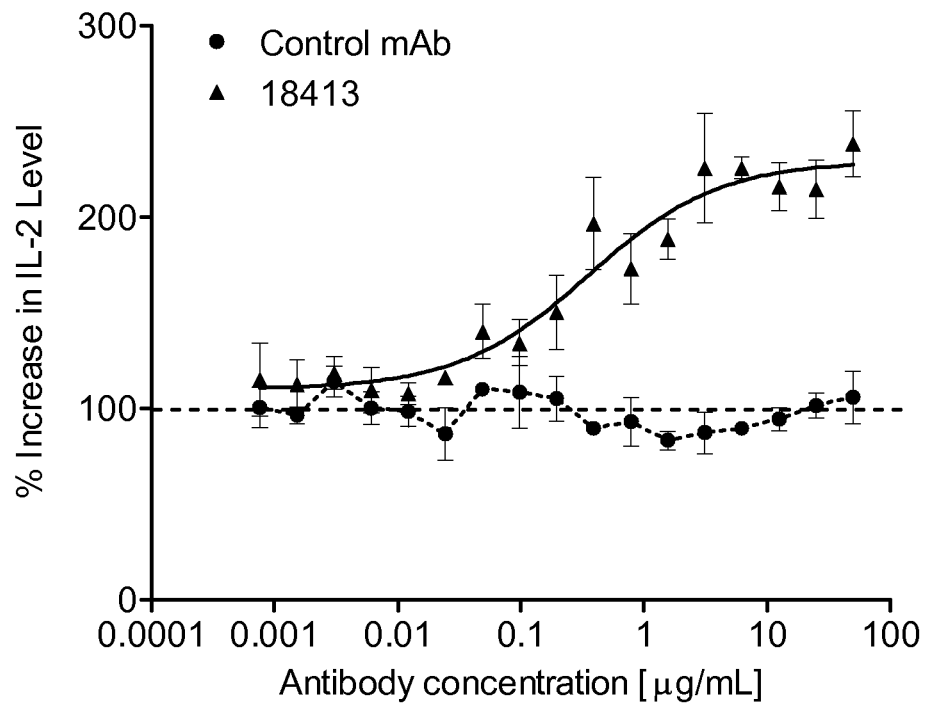
Figure 3F:
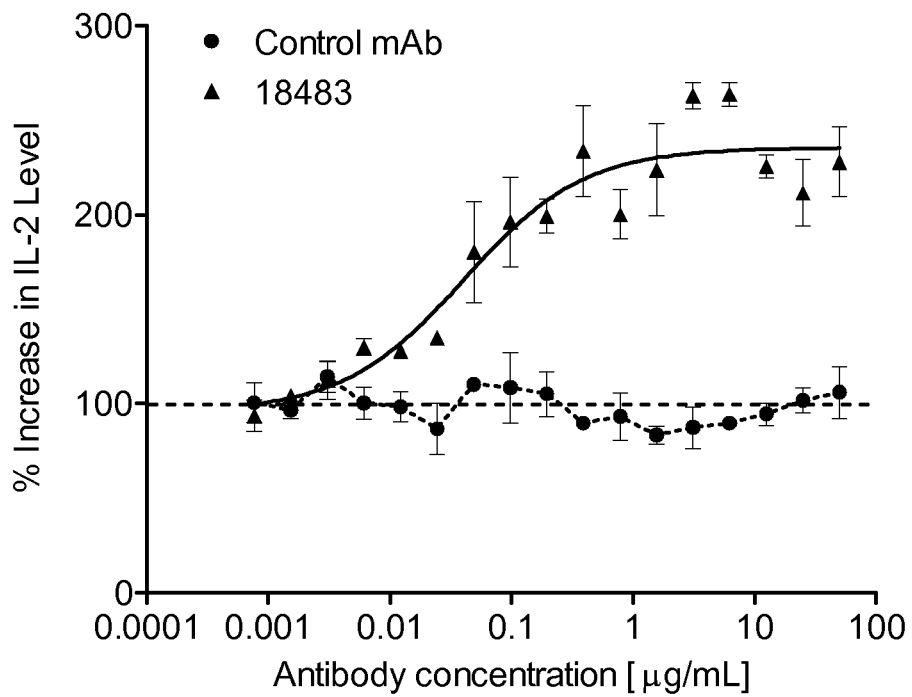
Figure 4A:
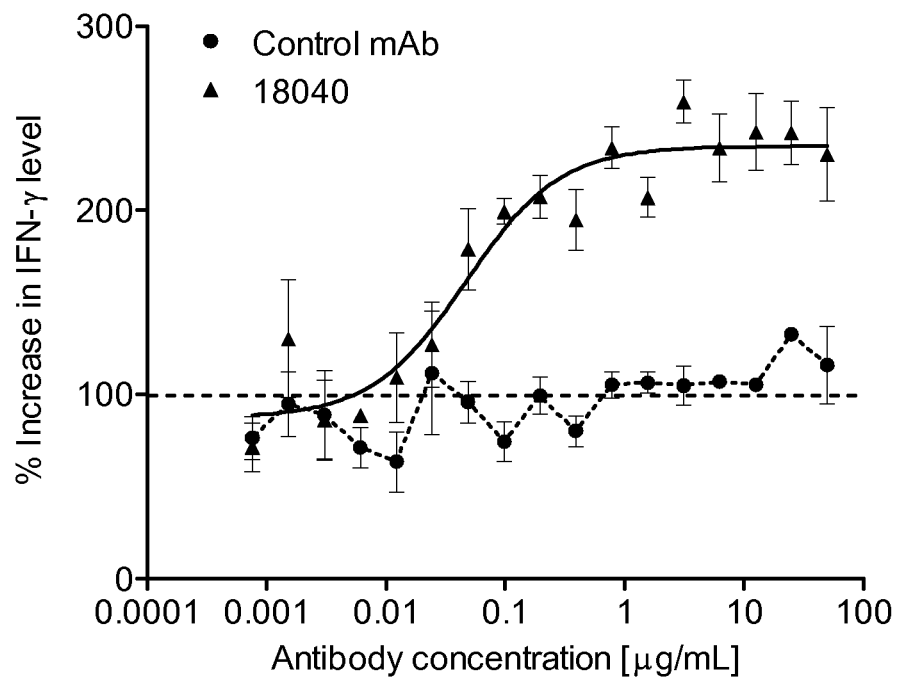
FIGS. 4A-4F show dose-response curves of twelve anti-PD-1 antibodies in the MLR (one-way mixed lymphocyte reaction) assay.
Figure 4A:
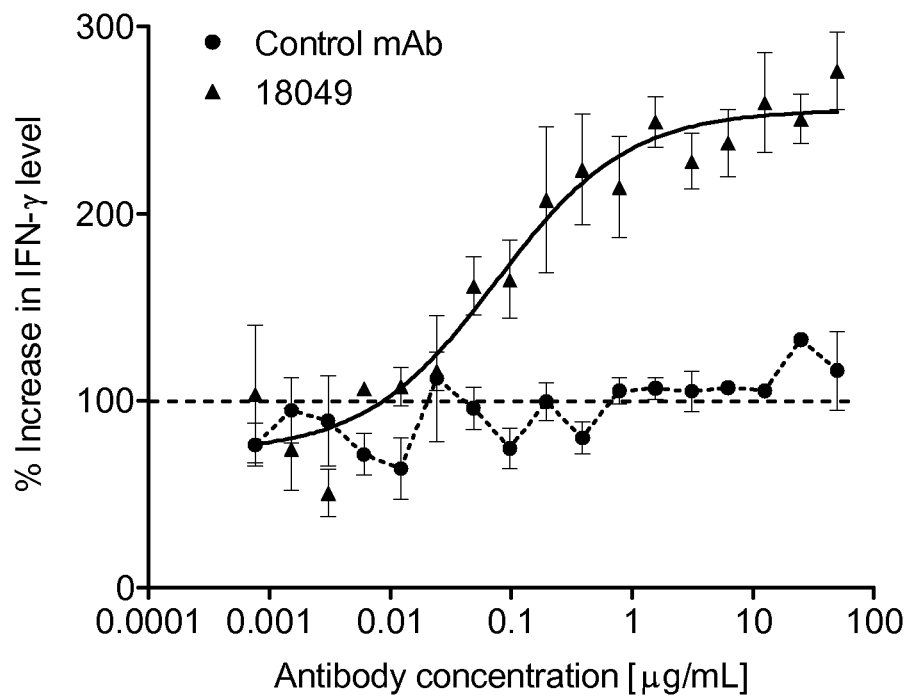
Figure 4B:
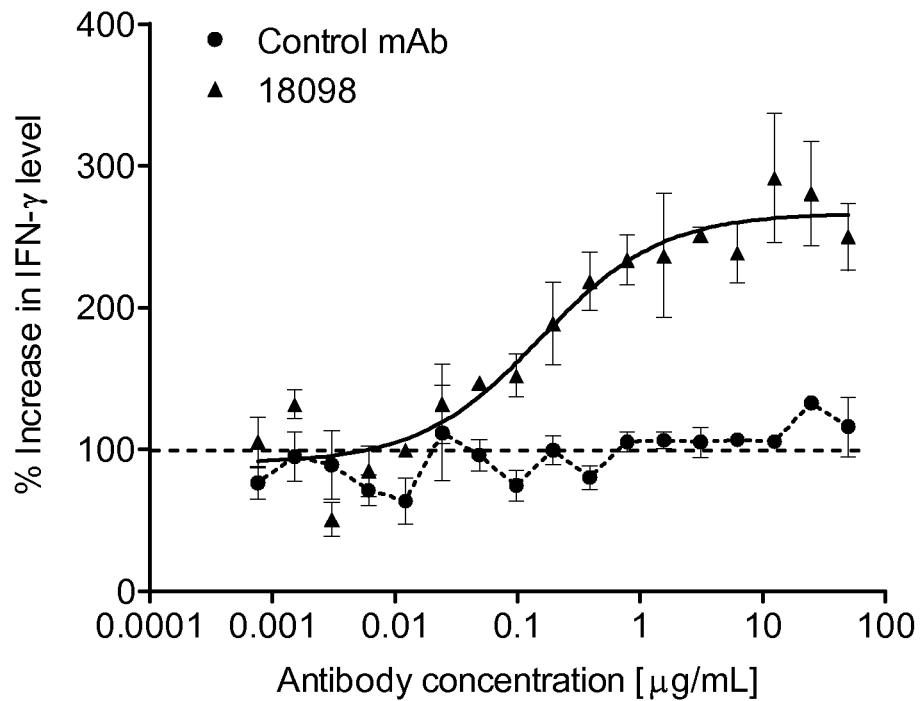
Figure 4B:
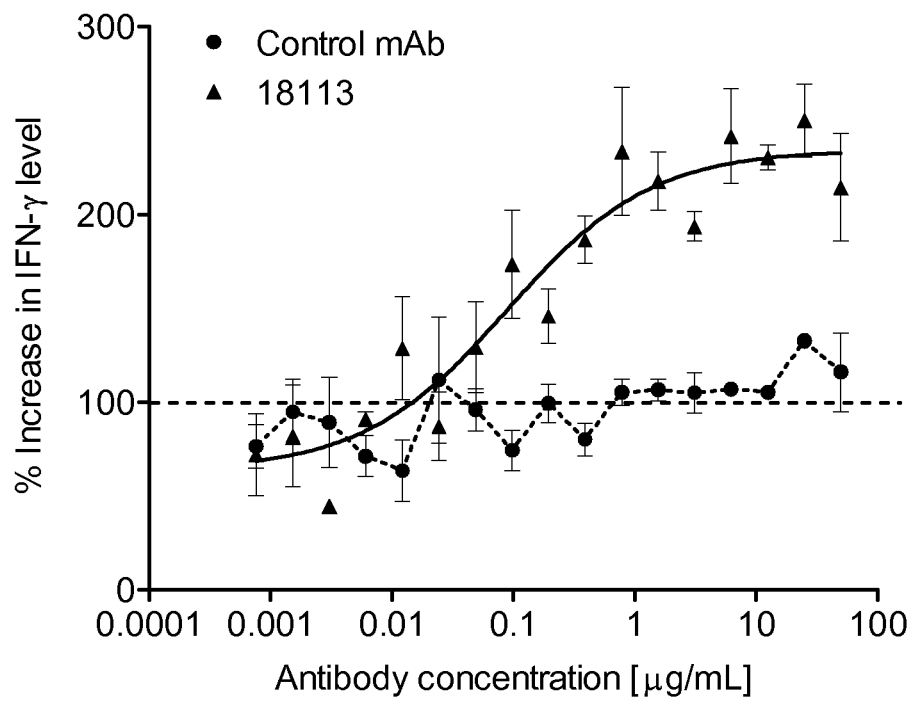
Figure 4C:
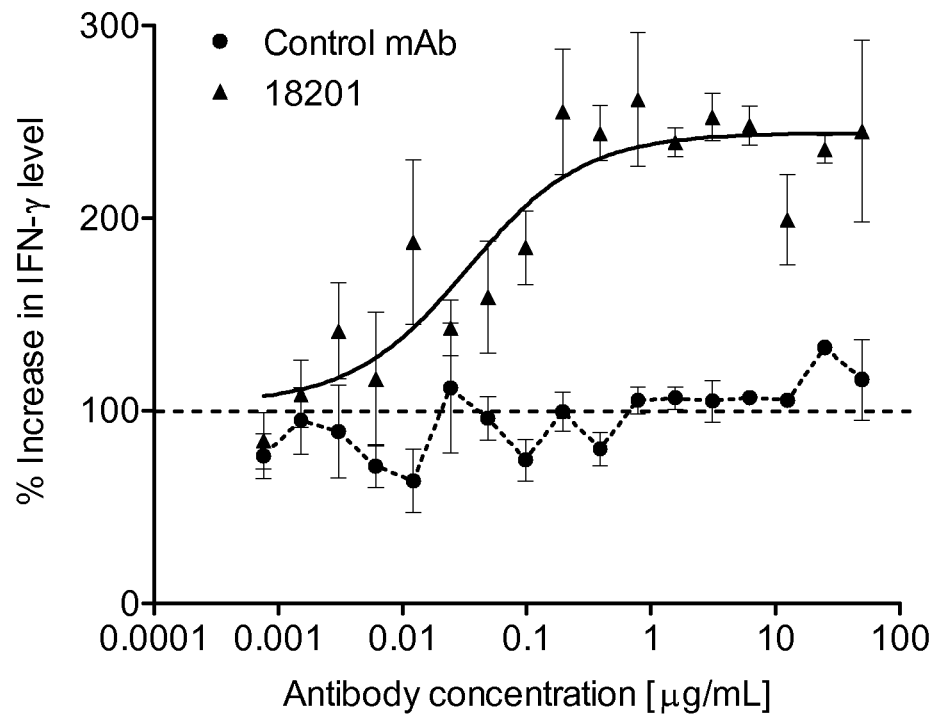
Figure 4C:
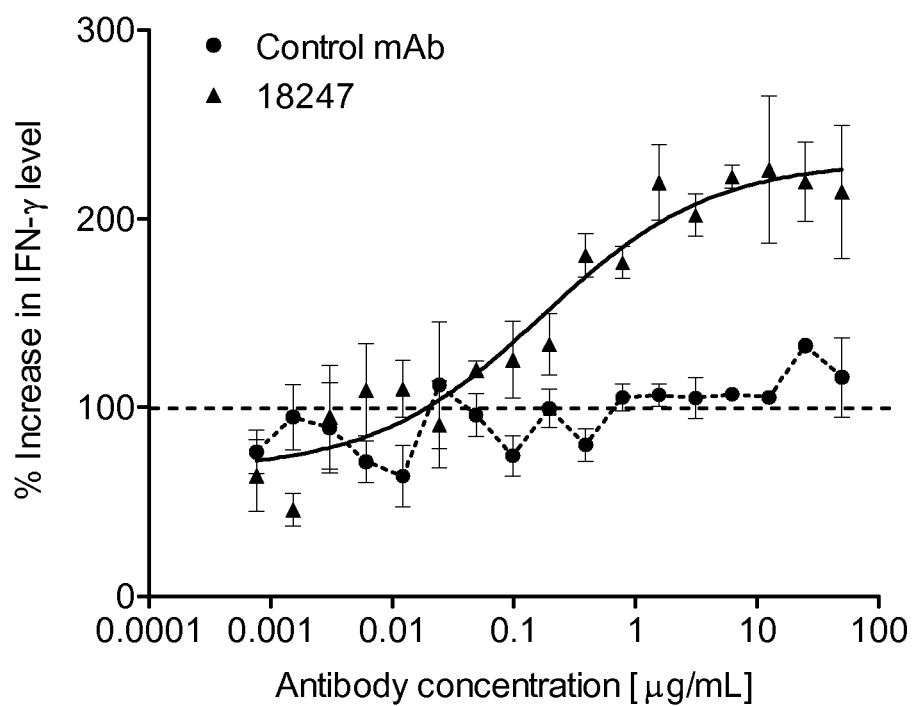
Figure 4D:
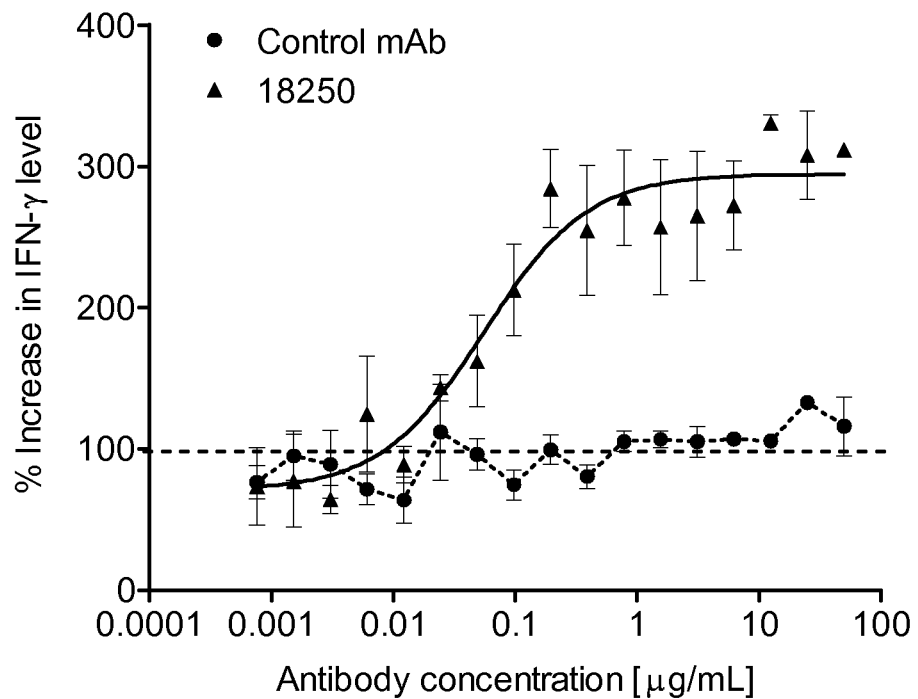
Figure 4D:
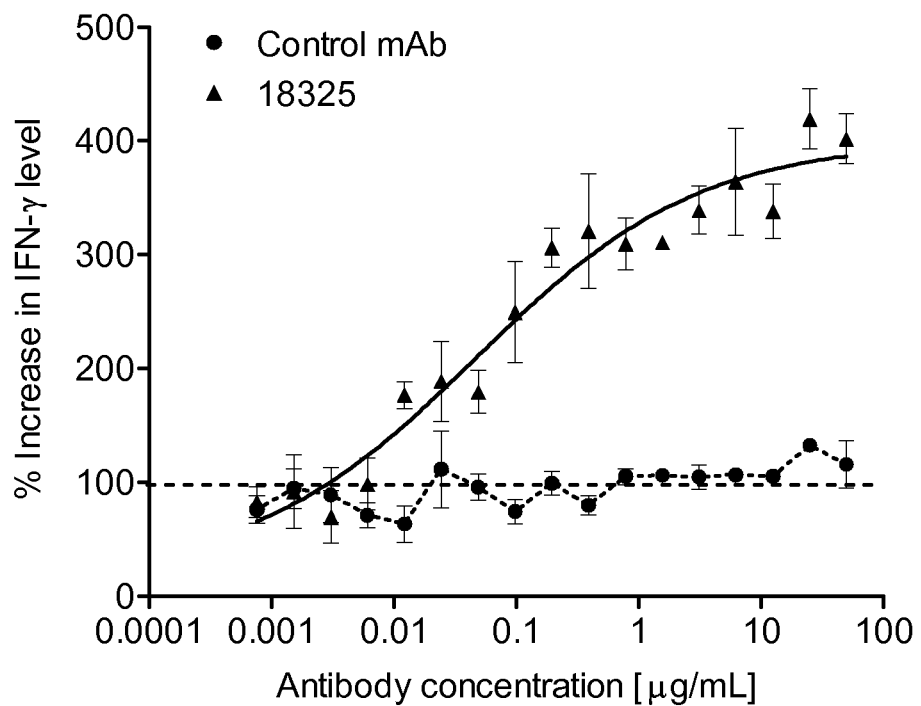
Figure 4E:
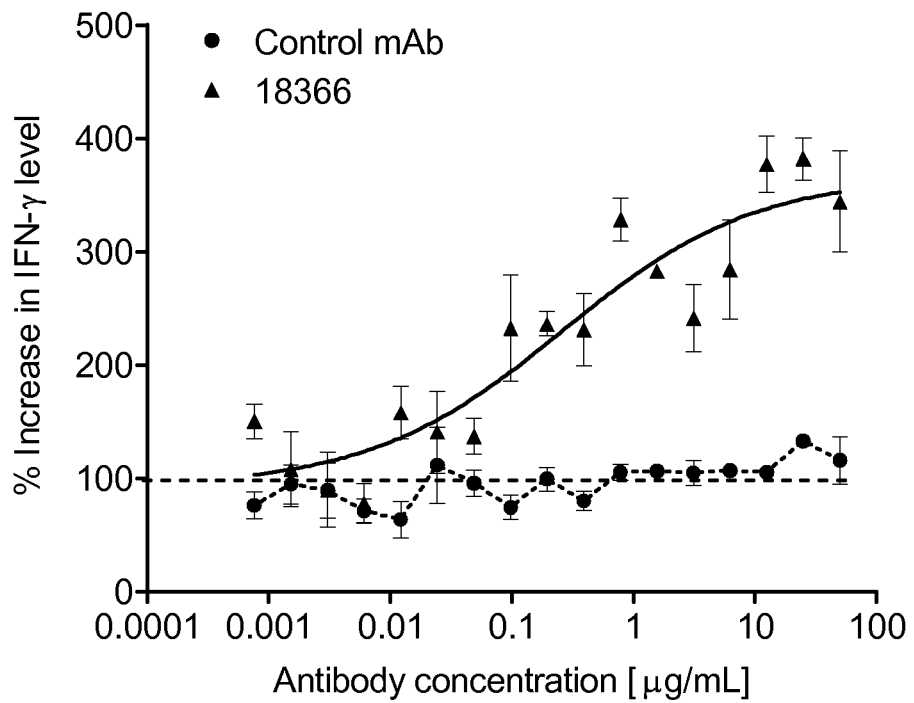
Figure 4E:
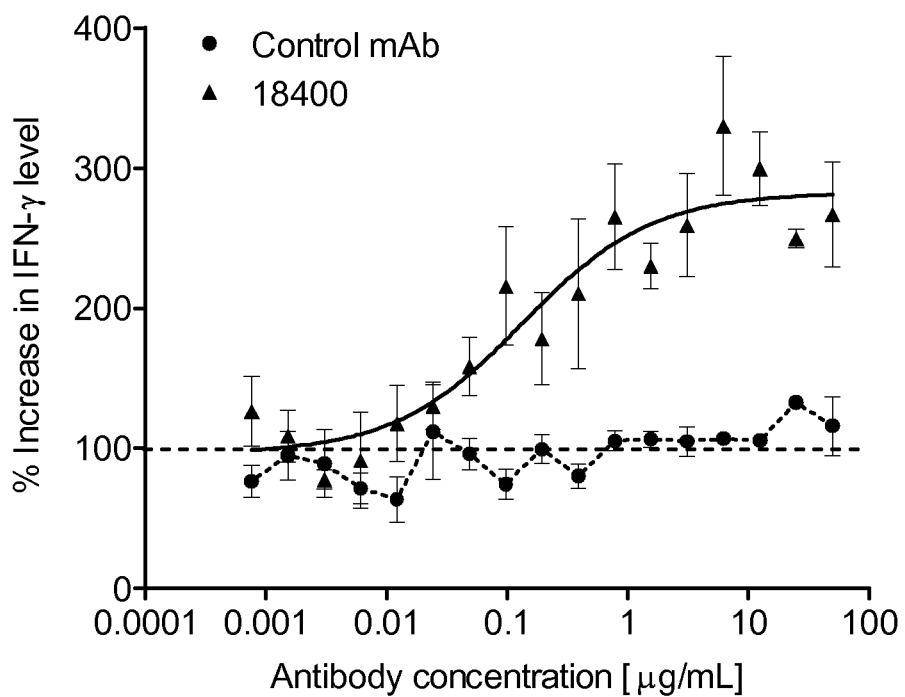
Figure 4F:
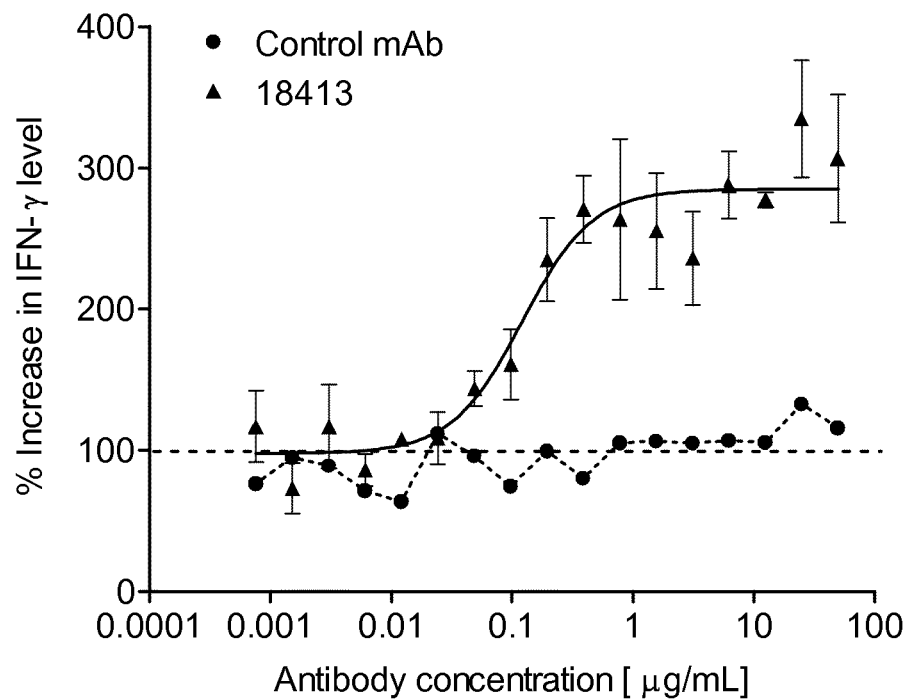
Figure 4F:
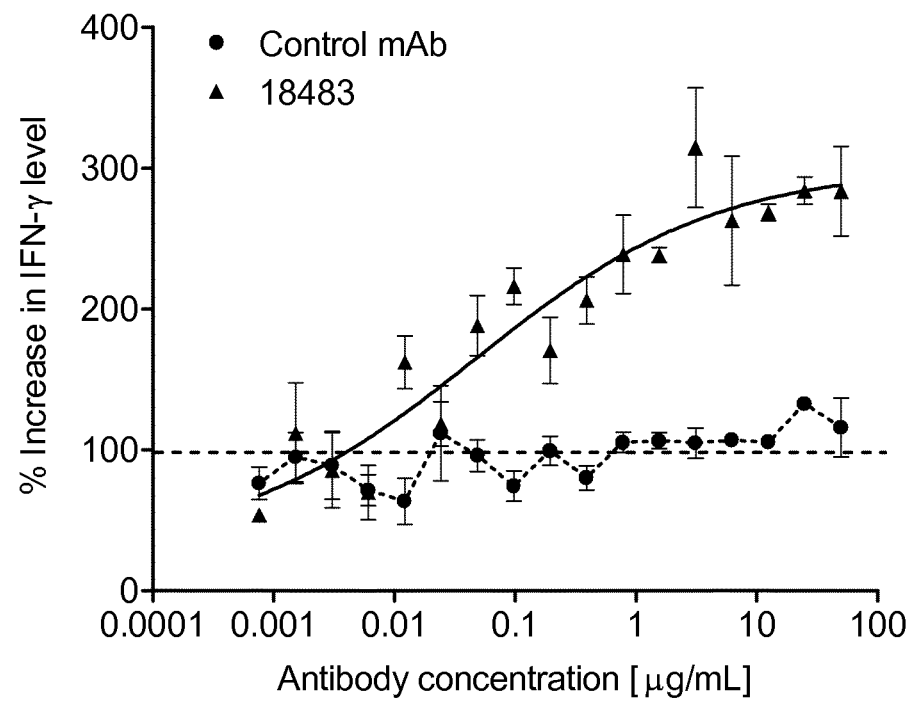

The present invention provides new anti-human PD-1 antibodies that can be used to enhance the immune system in a human patient, such as a cancer patient. Unless otherwise stated, as used herein, "PD-1" refers to human PD-1. A human PD-1 polypeptide sequence is available under Uniprot Accession No. Q15116 (PDCD1 _HUMAN).

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers in the heavy or light chain may be in accordance with IMGT® definitions (Lefranc et al., *Dev Comp Immunol* 27(1):55-77 (2003)); or the definitions of Kabat, *Sequences of Proteins of Immunological Interest* (National Institutes of Health, Bethesda, Md. (1987 and 1991)); Chothia & Lesk, *J. Mol. Biol.* 196:901-917 (1987); or Chothia et al., Nature 342:878-883 (1989).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, the term "germline" refers to the nucleotide and amino acid sequences of antibody genes and gene segments as they are passed from parents to offspring via germ cells. Germline sequences are distinguished from the nucleotide sequences encoding antibodies in mature B cells, which have been altered by recombination and hypermutation events during the course of B cell maturation. An antibody that "utilizes" a particular germline sequence has a nucleotide or amino acid sequence that aligns with that germline nucleotide sequence or with the amino acid sequence that it specifies more closely than with any other germline nucleotide or amino acid sequence.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is ≤1 mM, preferably ≤100 nM. A $K_D$ binding affinity constant can be measured, e.g., by surface plasmon resonance (SPR) (BIAcore™) or Bio-Layer Interferometry, for example using the IBIS MX96 SPR system from IBIS Technologies, the ProteOn™ XPR36 SPR system from Bio-Rad, or the Octet™ system from ForteBio.

The term "$k_{off}$" refers to the dissociation rate constant of a particular antibody-antigen interaction. A $k_{off}$ dissociation rate constant can be measured by SPR or Bio-Layer Interferometry, for example using one of the systems listed above.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., PD-1) or a relevant portion thereof, then screening for binding to the epitope.

One can determine whether an antibody binds to the same epitope as or competes for binding with an anti-PD-1 antibody of the invention by using methods known in the art, including, without limitation, competition assays, epitope binning, and alanine scanning. In some embodiments, the test antibody and an anti-PD-1 antibody of the invention bind to at least one common residue (e.g., at least two, three, four, five, or six common residues) on PD-1. In further embodiments, the contact residues on PD-1 are completely identical between the test antibody and the anti-PD-1 antibody of the invention. In one embodiment, one allows the anti-PD-1 antibody of the invention to bind to PD-1 under saturating conditions and then measures the ability of the test antibody to bind to PD-1. If the test antibody is able to bind to PD-1 at the same time as the reference anti-PD-1 antibody, then the test antibody binds to a different epitope than the reference anti-PD-1 antibody. However, if the test antibody is not able to bind to PD-1 at the same time, then the test antibody binds to the same epitope, an overlapping epitope, or an epitope that is in close proximity to the epitope bound by the anti-PD-1 antibody of the invention. This experiment can be performed using, e.g., ELISA, RIA, BIACORE™, SPR, Bio-Layer Interferometry or flow cytometry. To test whether an anti-PD-1 antibody cross-competes with another anti-PD-1 antibody, one may use the competition method described above in two directions, i.e., determining if the known antibody blocks the test antibody and vice versa. Such cross-competition experiments may be performed, e.g., using an *IBIS* MX96 SPR instrument or the Octet™ system.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., *Proc Natl Acad Sci USA*, 94:412-417 (1997), and the stepwise in vitro affinity maturation method of Wu et al., *Proc Natl Acad Sci USA* 95:6037-6042 (1998).

In some embodiments, the antibodies of the invention may be chimeric, humanized, or fully human. Although it is not possible to precisely predict the immunogenicity of a particular antibody drug, non-human antibodies tend to be more immunogenic in humans than human antibodies. Chimeric antibodies, where the foreign (e.g. rodent or avian) constant regions have been replaced with sequences of human origin, have been shown to be generally less immunogenic than antibodies of fully foreign origin. The trend in therapeutic antibodies is towards humanized or fully human antibodies.

The term "chimeric antibody" refers to an antibody that comprises sequences from two different animal species. For example, a chimeric antibody may contain the variable domains of a murine antibody (i.e., an antibody encoded by murine antibody genes such as an antibody obtained from an immunized mouse using hybridoma technology) linked to the constant regions of an antibody from another species (e.g., human, rabbit, or rat). In the case of a chimeric antibody, the non-human parts may be subjected to further alteration in order to humanize the antibody.

The term "humanize" refers to modifying an antibody that is wholly or partially of non-human origin (for example, a murine or chicken antibody obtained from immunization of mice or chickens, respectively, with an antigen of interest, or a chimeric antibody based on such a murine or chicken antibody), by replacing certain amino acid sequences, in particular in the framework regions (FR) and constant regions of the heavy and light chains, with corresponding human FR and constant region amino aicd sequences, in order to avoid or minimize an anti-drug antibody response in human patients. Antibodies of non-human origin thus can be humanized to reduce the risk of a human anti-drug antibody response.

The term "human antibody" refers to an antibody in which the variable domain and constant region sequences are derived from human sequences. The term encompasses antibodies with sequences that are derived from human genes but have been modified, e.g., to decrease immunogenicity, increase affinity, and/or increase stability. Further, the term encompasses antibodies produced recombinantly in nonhuman cells, which may impart glycosylation not typical of human cells. The term also encompasses antibodies produced in transgenic nonhuman organisms with human antibody genes (e.g., OmniRat® rats).

The term "antigen-binding portion" of an antibody (or simply "antibody portion"), as used herein, refers to one or more portions or fragments of an antibody that retain the ability to specifically bind to an antigen (e.g., human PD-1, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the VL, VH, CL and CH1 domains; (ii) a F(ab')2 fragment: a bivalent fragment comprising two Fab fragments linked by a disulfide bridge at the hinge region; (iii) an Fd fragment consisting of the VH and CH1 domains; (iv) a Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Also within the invention are antigen-binding molecules comprising a VH and/or a VL. In the case of a VH, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')₂ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The class (isotype) and subclass of anti-PD-1 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

When referring to particular amino acid residues in a given position of an antibody sequence, an indication of, e.g., "35S" refers to the position and residue, i.e., in this case indicating that a serine residue (S) is present in position 35 of the sequence. Similarly, an indication of, e.g., "13Q+35S" refers to the two residues in the respective positions. Unless otherwise indicated, all antibody amino acid residue numbers referred to in this disclosure are those under the IMGT® numbering scheme.

Anti-PD-1 Antibodies

The present invention provides antibodies directed against PD-1, and antigen-binding portions thereof. In a particular embodiment, the antibodies disclosed herein are human antibodies, e.g., generated from transgenic rats with human antibody genes. In certain embodiments, the human antibodies may contain certain mutations, e.g., to mutate primer-derived mutations back to the germline sequence (see, e.g., the "Symplex-corrected" variant sequences below) or to change mutations in framework regions back to the sequence of the closest V- or J-germline (see, e.g., the "germlined" variant sequences below).

In one embodiment, the anti-PD-1 antibody is selected from the group consisting of:
a) an antibody whose H-CDR1-3 comprise the amino acid sequences of SEQ ID NOs: 29-31, respectively;
b) an antibody whose heavy chain variable domain (VH) is at least 90% identical in sequence to the amino acid sequence of SEQ ID NO: 1;
c) an antibody whose VH comprises the amino acid sequence of SEQ ID NO: 1;
d) an antibody whose heavy chain (HC) comprises the amino acid sequences of SEQ ID NOs: 1 and 26;
e) an antibody whose L-CDR1-3 comprise the amino acid sequences of SEQ ID NOs: 32-34, respectively;
f) an antibody whose light chain variable domain (VL) is at least 90% identical in sequence to the amino acid sequence of SEQ ID NO: 2;
g) an antibody whose VL comprises the amino acid sequence of SEQ ID NO: 2;
h) an antibody whose light chain (LC) comprises the amino acid sequences of SEQ ID NOs: 2 and 28;
i) an antibody whose H-CDR1-3 and L-CDR1-3 comprise the amino acid sequences of SEQ ID NOs: 29-34, respectively;
j) an antibody whose VH is at least 90% identical in sequence to the amino acid sequence of SEQ ID NO: 1 and whose VL is at least 90% identical in sequence to the amino acid sequence of SEQ ID NO: 2;
k) an antibody whose VH comprises the amino acid sequence of SEQ ID NO: 1 and whose VL comprises the amino acid sequence of SEQ ID NO: 2; and
l) an antibody whose HC comprises the amino acid sequences of SEQ ID NOs: 1 and 26 and whose LC comprises the amino acid sequences of SEQ ID NOs: 2 and 28.

In one embodiment, the anti-PD-1 antibody is selected from the group consisting of:
a) an antibody whose H-CDR1-3 comprise the amino acid sequences of SEQ ID NOs: 35-37, respectively;
b) an antibody whose heavy chain variable domain (VH) is at least 90% identical in sequence to the amino acid sequence of SEQ ID NO: 3;
c) an antibody whose VH comprises the amino acid sequence of SEQ ID NO: 3;
d) an antibody whose heavy chain (HC) comprises the amino acid sequences of SEQ ID NOs: 3 and 26;
e) an antibody whose L-CDR1-3 comprise the amino acid sequences of SEQ ID NOs: 38-40, respectively;
f) an antibody whose light chain variable domain (VL) is at least 90% identical in sequence to the amino acid sequence of SEQ ID NO: 4;
g) an antibody whose VL comprises the amino acid sequence of SEQ ID NO: 4;
h) an antibody whose light chain (LC) comprises the amino acid sequences of SEQ ID NOs: 4 and 28;
i) an antibody whose H-CDR1-3 and L-CDR1-3 comprise the amino acid sequences of SEQ ID NOs: 35-40, respectively;
j) an antibody whose VH is at least 90% identical in sequence to the amino acid sequence of SEQ ID NO: 3 and whose VL is at least 90% identical in sequence to the amino acid sequence of SEQ ID NO: 4;
k) an antibody whose VH comprises the amino acid sequence of SEQ ID NO: 3 and whose VL comprises the amino acid sequence of SEQ ID NO: 4; and
l) an antibody whose HC comprises the amino acid sequences of SEQ ID NOs: 3 and 26 and whose LC comprises the amino acid sequences of SEQ ID NOs: 4 and 28.

In one embodiment, the anti-PD-1 antibody is selected from the group consisting of:
a) an antibody whose H-CDR1-3 comprise the amino acid sequences of SEQ ID NOs: 41-43, respectively;
b) an antibody whose heavy chain variable domain (VH) is at least 90% identical in sequence to the amino acid sequence of SEQ ID NO: 5;
c) an antibody whose VH comprises the amino acid sequence of SEQ ID NO: 5;
d) an antibody whose heavy chain (HC) comprises the amino acid sequences of SEQ ID NOs: 5 and 26;
e) an antibody whose L-CDR1-3 comprise the amino acid sequences of SEQ ID NOs: 44-46, respectively;
f) an antibody whose light chain variable domain (VL) is at least 90% identical in sequence to the amino acid sequence of SEQ ID NO: 6;
g) an antibody whose VL comprises the amino acid sequence of SEQ ID NO: 6;
h) an antibody whose light chain (LC) comprises the amino acid sequences of SEQ ID NOs: 6 and 28;
i) an antibody whose H-CDR1-3 and L-CDR1-3 comprise the amino acid sequences of SEQ ID NOs: 41-46, respectively;
j) an antibody whose VH is at least 90% identical in sequence to the amino acid sequence of SEQ ID NO: 5 and whose VL is at least 90% identical in sequence to the amino acid sequence of SEQ ID NO: 6;
k) an antibody whose VH comprises the amino acid sequence of SEQ ID NO: 5 and whose VL comprises the amino acid sequence of SEQ ID NO: 6; and
l) an antibody whose HC comprises the amino acid sequences of SEQ ID NOs: 5 and 26 and whose LC comprises the amino acid sequences of SEQ ID NOs: 6 and 28.

In one embodiment, the anti-PD-1 antibody is selected from the group consisting of:
a) an antibody whose H-CDR1-3 comprise the amino acid sequences of SEQ ID NOs: 29, 47 and 48, respectively;
b) an antibody whose heavy chain variable domain (VH) is at least 90% identical in sequence to the amino acid sequence of SEQ ID NO: 7;
c) an antibody whose VH comprises the amino acid sequence of SEQ ID NO: 7;
d) an antibody whose heavy chain (HC) comprises the amino acid sequences of SEQ ID NOs: 7 and 26;
e) an antibody whose L-CDR1-3 comprise the amino acid sequences of SEQ ID NOs: 49-51, respectively;
f) an antibody whose light chain variable domain (VL) is at least 90% identical in sequence to the amino acid sequence of SEQ ID NO: 8;
g) an antibody whose VL comprises the amino acid sequence of SEQ ID NO: 8;
h) an antibody whose light chain (LC) comprises the amino acid sequences of SEQ ID NOs: 8 and 28;
i) an antibody whose H-CDR1-3 and L-CDR1-3 comprise the amino acid sequences of SEQ ID NOs: 29, 47, 48 and 49-51, respectively;
j) an antibody whose VH is at least 90% identical in sequence to the amino acid sequence of SEQ ID NO: 7 and whose VL is at least 90% identical in sequence to the amino acid sequence of SEQ ID NO: 8;
k) an antibody whose VH comprises the amino acid sequence of SEQ ID NO: 7 and whose VL comprises the amino acid sequence of SEQ ID NO: 8; and
l) an antibody whose HC comprises the amino acid sequences of SEQ ID NOs: 7 and 26 and whose LC comprises the amino acid sequences of SEQ ID NOs: 8 and 28.

In one embodiment, the anti-PD-1 antibody is selected from the group consisting of:
a) an antibody whose H-CDR1-3 comprise the amino acid sequences of SEQ ID NOs: 52-54, respectively;
b) an antibody whose heavy chain variable domain (VH) is at least 90% identical in sequence to the amino acid sequence of SEQ ID NO: 9;
c) an antibody whose VH comprises the amino acid sequence of SEQ ID NO: 9;
d) an antibody whose heavy chain (HC) comprises the amino acid sequences of SEQ ID NOs: 9 and 26;
e) an antibody whose L-CDR1-3 comprise the amino acid sequences of SEQ ID NOs: 38, 45 and 55, respectively;
f) an antibody whose light chain variable domain (VL) is at least 90% identical in sequence to the amino acid sequence of SEQ ID NO: 10;
g) an antibody whose VL comprises the amino acid sequence of SEQ ID NO: 10;
h) an antibody whose light chain (LC) comprises the amino acid sequences of SEQ ID NOs: 10 and 28;
i) an antibody whose H-CDR1-3 and L-CDR1-3 comprise the amino acid sequences of SEQ ID NOs: 52-54 and 38, 45 and 55, respectively;
j) an antibody whose VH is at least 90% identical in sequence to the amino acid sequence of SEQ ID NO: 9 and whose VL is at least 90% identical in sequence to the amino acid sequence of SEQ ID NO: 10;
k) an antibody whose VH comprises the amino acid sequence of SEQ ID NO: 9 and whose VL comprises the amino acid sequence of SEQ ID NO: 10; and
l) an antibody whose HC comprises the amino acid sequences of SEQ ID NOs: 9 and 26 and whose LC comprises the amino acid sequences of SEQ ID NOs: 10 and 28.

In one embodiment, the anti-PD-1 antibody is selected from the group consisting of:
a) an antibody whose H-CDR1-3 comprise the amino acid sequences of SEQ ID NOs: 29, 56 and 48, respectively;
b) an antibody whose heavy chain variable domain (VH) is at least 90% identical in sequence to the amino acid sequence of SEQ ID NO: 1;
c) an antibody whose VH comprises the amino acid sequence of SEQ ID NO: 11;
d) an antibody whose heavy chain (HC) comprises the amino acid sequences of SEQ ID NOs: 11 and 26;
e) an antibody whose L-CDR1-3 comprise the amino acid sequences of SEQ ID NOs: 57, 33 and 51, respectively;
f) an antibody whose light chain variable domain (VL) is at least 90% identical in sequence to the amino acid sequence of SEQ ID NO: 12;
g) an antibody whose VL comprises the amino acid sequence of SEQ ID NO: 12;
h) an antibody whose light chain (LC) comprises the amino acid sequences of SEQ ID NOs: 12 and 28;
i) an antibody whose H-CDR1-3 and L-CDR1-3 comprise the amino acid sequences of SEQ ID NOs: 29, 56 and 48 and 57, 33 and 51, respectively;
j) an antibody whose VH is at least 90% identical in sequence to the amino acid sequence of SEQ ID NO: 11 and whose VL is at least 90% identical in sequence to the amino acid sequence of SEQ ID NO: 12;
k) an antibody whose VH comprises the amino acid sequence of SEQ ID NO: 11 and whose VL comprises the amino acid sequence of SEQ ID NO: 12; and
l) an antibody whose HC comprises the amino acid sequences of SEQ ID NOs: 11 and 26 and whose LC comprises the amino acid sequences of SEQ ID NOs: 12 and 28.

In one embodiment, the anti-PD-1 antibody is selected from the group consisting of:
a) an antibody whose H-CDR1-3 comprise the amino acid sequences of SEQ ID NOs: 58-60, respectively;
b) an antibody whose heavy chain variable domain (VH) is at least 90% identical in sequence to the amino acid sequence of SEQ ID NO: 13;
c) an antibody whose VH comprises the amino acid sequence of SEQ ID NO: 13;
d) an antibody whose heavy chain (HC) comprises the amino acid sequences of SEQ ID NOs: 13 and 26;
e) an antibody whose L-CDR1-3 comprise the amino acid sequences of SEQ ID NOs: 57, 33 and 34, respectively;
f) an antibody whose light chain variable domain (VL) is at least 90% identical in sequence to the amino acid sequence of SEQ ID NO: 14;
g) an antibody whose VL comprises the amino acid sequence of SEQ ID NO: 14;
h) an antibody whose light chain (LC) comprises the amino acid sequences of SEQ ID NOs: 14 and 28;

i) an antibody whose H-CDR1-3 and L-CDR1-3 comprise the amino acid sequences of SEQ ID NOs: 58-60 and 57, 33 and 34, respectively;
j) an antibody whose VH is at least 90% identical in sequence to the amino acid sequence of SEQ ID NO: 13 and whose VL is at least 90% identical in sequence to the amino acid sequence of SEQ ID NO: 14;
k) an antibody whose VH comprises the amino acid sequence of SEQ ID NO: 13 and whose VL comprises the amino acid sequence of SEQ ID NO: 14; and
l) an antibody whose HC comprises the amino acid sequences of SEQ ID NOs: 13 and 26 and whose LC comprises the amino acid sequences of SEQ ID NOs: 14 and 28.

In one embodiment, the anti-PD-1 antibody is selected from the group consisting of:
a) an antibody whose H-CDR1-3 comprise the amino acid sequences of SEQ ID NOs: 61, 62 and 43, respectively;
b) an antibody whose heavy chain variable domain (VH) is at least 90% identical in sequence to the amino acid sequence of SEQ ID NO: 15;
c) an antibody whose VH comprises the amino acid sequence of SEQ ID NO: 15;
d) an antibody whose heavy chain (HC) comprises the amino acid sequences of SEQ ID NOs: 15 and 26;
e) an antibody whose L-CDR1-3 comprise the amino acid sequences of SEQ ID NOs: 44-46, respectively;
f) an antibody whose light chain variable domain (VL) is at least 90% identical in sequence to the amino acid sequence of SEQ ID NO: 16;
g) an antibody whose VL comprises the amino acid sequence of SEQ ID NO: 16;
h) an antibody whose light chain (LC) comprises the amino acid sequences of SEQ ID NOs: 16 and 28;
i) an antibody whose H-CDR1-3 and L-CDR1-3 comprise the amino acid sequences of SEQ ID NOs: 61, 62 and 43 and 44-46, respectively;
j) an antibody whose VH is at least 90% identical in sequence to the amino acid sequence of SEQ ID NO: 15 and whose VL is at least 90% identical in sequence to the amino acid sequence of SEQ ID NO: 16;
k) an antibody whose VH comprises the amino acid sequence of SEQ ID NO: 15 and whose VL comprises the amino acid sequence of SEQ ID NO: 16; and
l) an antibody whose HC comprises the amino acid sequences of SEQ ID NOs: 15 and 26 and whose LC comprises the amino acid sequences of SEQ ID NOs: 16 and 28.

In one embodiment, the anti-PD-1 antibody is selected from the group consisting of:
a) an antibody whose H-CDR1-3 comprise the amino acid sequences of SEQ ID NOs: 63-65, respectively;
b) an antibody whose heavy chain variable domain (VH) is at least 90% identical in sequence to the amino acid sequence of SEQ ID NO: 17;
c) an antibody whose VH comprises the amino acid sequence of SEQ ID NO: 17;
d) an antibody whose heavy chain (HC) comprises the amino acid sequences of SEQ ID NOs: 17 and 26;
e) an antibody whose L-CDR1-3 comprise the amino acid sequences of SEQ ID NOs: 32-34, respectively;
f) an antibody whose light chain variable domain (VL) is at least 90% identical in sequence to the amino acid sequence of SEQ ID NO: 18;
g) an antibody whose VL comprises the amino acid sequence of SEQ ID NO: 18;
h) an antibody whose light chain (LC) comprises the amino acid sequences of SEQ ID NOs: 18 and 28;
i) an antibody whose H-CDR1-3 and L-CDR1-3 comprise the amino acid sequences of SEQ ID NOs: 63-65 and 32-34, respectively;
j) an antibody whose VH is at least 90% identical in sequence to the amino acid sequence of SEQ ID NO: 17 and whose VL is at least 90% identical in sequence to the amino acid sequence of SEQ ID NO: 18;
k) an antibody whose VH comprises the amino acid sequence of SEQ ID NO: 17 and whose VL comprises the amino acid sequence of SEQ ID NO: 18; and
l) an antibody whose HC comprises the amino acid sequences of SEQ ID NOs: 17 and 26 and whose LC comprises the amino acid sequences of SEQ ID NOs: 18 and 28.

In one embodiment, the anti-PD-1 antibody is selected from the group consisting of:
a) an antibody whose H-CDR1-3 comprise the amino acid sequences of SEQ ID NOs: 66-68, respectively;
b) an antibody whose heavy chain variable domain (VH) is at least 90% identical in sequence to the amino acid sequence of SEQ ID NO: 19;
c) an antibody whose VH comprises the amino acid sequence of SEQ ID NO: 19;
d) an antibody whose heavy chain (HC) comprises the amino acid sequences of SEQ ID NOs: 19 and 26;
e) an antibody whose L-CDR1-3 comprise the amino acid sequences of SEQ ID NOs: 38, 45 and 55, respectively;
f) an antibody whose light chain variable domain (VL) is at least 90% identical in sequence to the amino acid sequence of SEQ ID NO: 20;
g) an antibody whose VL comprises the amino acid sequence of SEQ ID NO: 20;
h) an antibody whose light chain (LC) comprises the amino acid sequences of SEQ ID NOs: 20 and 28;
i) an antibody whose H-CDR1-3 and L-CDR1-3 comprise the amino acid sequences of SEQ ID NOs: 66-68 and 38, 45 and 55, respectively;
j) an antibody whose VH is at least 90% identical in sequence to the amino acid sequence of SEQ ID NO: 19 and whose VL is at least 90% identical in sequence to the amino acid sequence of SEQ ID NO: 20;
k) an antibody whose VH comprises the amino acid sequence of SEQ ID NO: 19 and whose VL comprises the amino acid sequence of SEQ ID NO: 20; and
l) an antibody whose HC comprises the amino acid sequences of SEQ ID NOs: 19 and 26 and whose LC comprises the amino acid sequences of SEQ ID NOs: 20 and 28.

In one embodiment, the anti-PD-1 antibody is selected from the group consisting of:
a) an antibody whose H-CDR1-3 comprise the amino acid sequences of SEQ ID NOs: 69-71, respectively;
b) an antibody whose heavy chain variable domain (VH) is at least 90% identical in sequence to the amino acid sequence of SEQ ID NO: 21;
c) an antibody whose VH comprises the amino acid sequence of SEQ ID NO: 21;
d) an antibody whose heavy chain (HC) comprises the amino acid sequences of SEQ ID NOs: 21 and 26;
e) an antibody whose L-CDR1-3 comprise the amino acid sequences of SEQ ID NOs: 72, 45 and 73, respectively;
f) an antibody whose light chain variable domain (VL) is at least 90% identical in sequence to the amino acid sequence of SEQ ID NO: 22;

g) an antibody whose VL comprises the amino acid sequence of SEQ ID NO: 22;
h) an antibody whose light chain (LC) comprises the amino acid sequences of SEQ ID NOs: 22 and 28;
i) an antibody whose H-CDR1-3 and L-CDR1-3 comprise the amino acid sequences of SEQ ID NOs: 69-71 and 72, 45 and 73, respectively;
j) an antibody whose VH is at least 90% identical in sequence to the amino acid sequence of SEQ ID NO: 21 and whose VL is at least 90% identical in sequence to the amino acid sequence of SEQ ID NO: 22;
k) an antibody whose VH comprises the amino acid sequence of SEQ ID NO: 21 and whose VL comprises the amino acid sequence of SEQ ID NO: 22; and
l) an antibody whose HC comprises the amino acid sequences of SEQ ID NOs: 21 and 26 and whose LC comprises the amino acid sequences of SEQ ID NOs: 22 and 28.

In one embodiment, the anti-PD-1 antibody is selected from the group consisting of:
a) an antibody whose H-CDR1-3 comprise the amino acid sequences of SEQ ID NOs: 74-76, respectively;
b) an antibody whose heavy chain variable domain (VH) is at least 90% identical in sequence to the amino acid sequence of SEQ ID NO: 23;
c) an antibody whose VH comprises the amino acid sequence of SEQ ID NO: 23;
d) an antibody whose heavy chain (HC) comprises the amino acid sequences of SEQ ID NOs: 23 and 26;
e) an antibody whose L-CDR1-3 comprise the amino acid sequences of SEQ ID NOs: 57, 33 and 34, respectively;
f) an antibody whose light chain variable domain (VL) is at least 90% identical in sequence to the amino acid sequence of SEQ ID NO: 24;
g) an antibody whose VL comprises the amino acid sequence of SEQ ID NO: 24;
h) an antibody whose light chain (LC) comprises the amino acid sequences of SEQ ID NOs: 24 and 28;
i) an antibody whose H-CDR1-3 and L-CDR1-3 comprise the amino acid sequences of SEQ ID NOs: 74-76 and 57, 33 and 34, respectively;
j) an antibody whose VH is at least 90% identical in sequence to the amino acid sequence of SEQ ID NO: 23 and whose VL is at least 90% identical in sequence to the amino acid sequence of SEQ ID NO: 24;
k) an antibody whose VH comprises the amino acid sequence of SEQ ID NO: 23 and whose VL comprises the amino acid sequence of SEQ ID NO: 24; and
l) an antibody whose HC comprises the amino acid sequences of SEQ ID NOs: 23 and 26 and whose LC comprises the amino acid sequences of SEQ ID NOs: 24 and 28.

In other embodiments, the anti-PD-1 antibody has a VH and VL that are at least 90% identical in amino acid sequence to the the VH and VL, respectively, of any one of antibodies 18040, 18049, 18098, 18113, 18201, 18247, 18250, 18325, 18366, 18400, 18413 and 18483, e.g., at least 92%, 95%, 96%, 97%, 98%, or 99% identical in sequence to the VH and VL of any of said antibodies. In some embodiments, an antigen-binding portion of the anti-PD-1 antibody has said VH and VL.

In some embodiments, the anti-PD-1 antibody has a VH and VL that comprise the VH and VL amino acid sequences, respectively, of any one of antibodies 18040, 18049, 18098, 18113, 18201, 18247, 18250, 18325, 18366, 18400, 18413 and 18483. In some embodiments, an antigen-binding portion of the anti-PD-1 antibody has said VH and VL.

In some embodiments, the anti-PD-1 antibody or antigen-binding portion of the invention comprises the H-CDR1-3 and L-CDR1-3 amino acid sequences of:
a) SEQ ID NOs: 29, 30, 31, 32, 33, and 34, respectively;
b) SEQ ID NOs: 35, 36, 37, 38, 39, and 40, respectively;
c) SEQ ID NOs: 41, 42, 43, 44, 45, and 46, respectively;
d) SEQ ID NOs: 29, 47, 48, 49, 50, and 51, respectively;
e) SEQ ID NOs: 52, 53, 54, 38, 45, and 55, respectively;
f) SEQ ID NOs: 29, 56, 48, 57, 33, and 51, respectively;
g) SEQ ID NOs: 58, 59, 60, 57, 33, and 34, respectively;
h) SEQ ID NOs: 61, 62, 43, 44, 45, and 46, respectively;
i) SEQ ID NOs: 63, 64, 65, 32, 33, and 34, respectively;
j) SEQ ID NOs: 66, 67, 68, 38, 45, and 55, respectively;
k) SEQ ID NOs: 69, 70, 71, 72, 45, and 73, respectively; or
l) SEQ ID NOs: 74, 75, 76, 57, 33, and 34, respectively.

In some embodiments, the anti-PD-1 antibody or antigen-binding portion of the invention comprises a VH and a VL that are 80%, 85%, 90%, 91%, 92%, 93%, 94%, 95%, 96%, 97%, 98%, or 99% identical to the amino acid sequences of:
a) SEQ ID NOs: 1 and 2, respectively;
b) SEQ ID NOs: 3 and 4, respectively;
c) SEQ ID NOs: 5 and 6, respectively;
d) SEQ ID NOs: 7 and 8, respectively;
e) SEQ ID NOs: 9 and 10, respectively;
f) SEQ ID NOs: 11 and 12, respectively;
g) SEQ ID NOs: 13 and 14, respectively;
h) SEQ ID NOs: 15 and 16, respectively;
i) SEQ ID NOs: 17 and 18, respectively;
j) SEQ ID NOs: 19 and 20, respectively;
k) SEQ ID NOs: 21 and 22, respectively; or
l) SEQ ID NOs: 23 and 24, respectively.

In some embodiments, the anti-PD-1 antibody or antigen-binding portion of the invention comprises a VH and a VL that have the amino acid sequences of:
a) SEQ ID NOs: 1 and 2, respectively;
b) SEQ ID NOs: 3 and 4, respectively;
c) SEQ ID NOs: 5 and 6, respectively;
d) SEQ ID NOs: 7 and 8, respectively;
e) SEQ ID NOs: 9 and 10, respectively;
f) SEQ ID NOs: 11 and 12, respectively;
g) SEQ ID NOs: 13 and 14, respectively;
h) SEQ ID NOs: 15 and 16, respectively;
i) SEQ ID NOs: 17 and 18, respectively;
j) SEQ ID NOs: 19 and 20, respectively;
k) SEQ ID NOs: 21 and 22, respectively; or
l) SEQ ID NOs: 23 and 24, respectively.

In some embodiments, the anti-PD-1 antibody comprises:
a) an HC with the amino acid sequences of SEQ ID NOs: 1 and 26 and an LC with the amino acid sequences of SEQ ID NOs: 2 and 28;
b) an HC with the amino acid sequences of SEQ ID NOs: 3 and 26 and an LC with the amino acid sequences of SEQ ID NOs: 4 and 28;
c) an HC with the amino acid sequences of SEQ ID NOs: 5 and 26 and an LC with the amino acid sequences of SEQ ID NOs: 6 and 28;
d) an HC with the amino acid sequences of SEQ ID NOs: 7 and 26 and an LC with the amino acid sequences of SEQ ID NOs: 8 and 28;
e) an HC with the amino acid sequences of SEQ ID NOs: 9 and 26 and an LC with the amino acid sequences of SEQ ID NOs: 10 and 28;
f) an HC with the amino acid sequences of SEQ ID NOs: 11 and 26 and an LC with the amino acid sequences of SEQ ID NOs: 12 and 28;

g) an HC with the amino acid sequences of SEQ ID NOs: 13 and 26 and an LC with the amino acid sequences of SEQ ID NOs: 14 and 28;
h) an HC with the amino acid sequences of SEQ ID NOs: 15 and 26 and an LC with the amino acid sequences of SEQ ID NOs: 16 and 28;
i) an HC with the amino acid sequences of SEQ ID NOs: 17 and 26 and an LC with the amino acid sequences of SEQ ID NOs: 18 and 28;
j) an HC with the amino acid sequences of SEQ ID NOs: 19 and 26 and an LC with the amino acid sequences of SEQ ID NOs: 20 and 28;
k) an HC with the amino acid sequences of SEQ ID NOs: 21 and 26 and an LC with the amino acid sequences of SEQ ID NOs: 22 and 28; or
l) an HC with the amino acid sequences of SEQ ID NOs: 23 and 26 and an LC with the amino acid sequences of SEQ ID NOs: 24 and 28.

In one embodiment, the anti-PD-1 antibody has a VH and VL that comprise the VH and VL amino acid sequences, respectively, of antibody 18040, i.e., where the VH comprises the amino acid sequence of SEQ ID NO: 1 and the VL comprises the amino acid sequence of SEQ ID NO: 2. In this embodiment, the VH may comprise the amino acid sequence of SEQ ID NO: 1, wherein X in position 35 is S, and/or X in position 84 is N. In certain embodiments, the VL may also comprise the amino acid sequence of SEQ ID NO: 2, wherein X in position 40 is A, and/or X in position 55 is Y.

In one embodiment, the anti-PD-1 antibody has a VH and VL that comprise the VH and VL amino acid sequences, respectively, of antibody 18049, i.e., where the VH comprises the amino acid sequence of SEQ ID NO: 3 and the VL comprises the amino acid sequence of SEQ ID NO: 4. In this embodiment, the VL may comprise the amino acid sequence of SEQ ID NO: 4, wherein X in position 1 is D, and/or X in position 3 is Q. In some embodiments, the VL comprises D in position 1 and Q in position 3. In certain embodiments, the VL may also comprise the amino acid sequence of SEQ ID NO: 4, wherein X in position 53 is S.

In one embodiment, the anti-PD-1 antibody has a VH and VL that comprise the VH and VL amino acid sequences, respectively, of antibody 18098, i.e., where the VH comprises the amino acid sequence of SEQ ID NO: 5 and the VL comprises the amino acid sequence of SEQ ID NO: 6. In this embodiment, the VH may comprise the amino acid sequence of SEQ ID NO: 5, wherein: X in position 1 is E, and/or X in position 5 is V. In some embodiments, the VH comprises E in position 1 and V in position 5. In certain embodiments, the VH may also comprise the amino acid sequence of SEQ ID NO: 5, wherein X in position 13 is Q, X in position 35 is S, X in position 46 is E, X in position 50 is A, X in position 77 is N, X in position 80 is Y, and/or X in position 115 is M. The VL may comprise the amino acid sequence of SEQ ID NO: 6, wherein X in position 4 is M.

In one embodiment, the anti-PD-1 antibody has a VH and VL that comprise the VH and VL amino acid sequences, respectively, of antibody 18113, i.e., where the VH comprises the amino acid sequence of SEQ ID NO: 7 and the VL comprises the amino acid sequence of SEQ ID NO: 8. In this embodiment, the VH may comprise the amino acid sequence of SEQ ID NO: 7 wherein X in position 64 is V. The VL may comprise the amino acid sequence of SEQ ID NO: 8, wherein X in position 3 is V, and/or X in position 4 is M. In some embodiments, the VL comprises V in position 3 and M in position 4. In certain embodiments, the VL may also comprise the amino acid sequence of SEQ ID NO: 8 wherein X in position 69 is S.

In one embodiment, the anti-PD-1 antibody has a VH and VL that comprise the VH and VL amino acid sequences, respectively, of antibody 18201, i.e., where the VH comprises the amino acid sequence of SEQ ID NO: 9 and the VL comprises the amino acid sequence of SEQ ID NO: 10. In this embodiment, the VH may comprise the amino acid sequence of SEQ ID NO: 9 wherein X in position 5 is Q. In some embodiments, the VH may also comprise the amino acid sequence of SEQ ID NO: 9, wherein X in position 59 is N, X in position 76 is K, and/or X in position 83 is L. The VL may comprise the amino acid sequence of SEQ ID NO: 10 wherein X in position 1 is A.

In one embodiment, the anti-PD-1 antibody has a VH and VL that comprise the VH and VL amino acid sequences, respectively, of antibody 18247, i.e., where the VH comprises the amino acid sequence of SEQ ID NO: 11 and the VL comprises the amino acid sequence of SEQ ID NO: 12. In this embodiment, the VH may comprise the amino acid sequence of SEQ ID NO: 11, wherein X in position 10 is G, and/or X in position 16 is G. The VL may comprise the amino acid sequence of SEQ ID NO: 12, wherein: X in position 1 is D, and/or X in position 4 is M. In some embodiments, the VL comprises D in position 1 and M in position 4. In certain embodiments, the VL may also comprise the amino acid sequence of SEQ ID NO: 12, wherein X in position 55 is Y, and/or X in position 93 is Y.

In one embodiment, the anti-PD-1 antibody has a VH and VL that comprise the VH and VL amino acid sequences, respectively, of antibody 18250, i.e., where the VH comprises the amino acid sequence of SEQ ID NO: 13 and the VL comprises the amino acid sequence of SEQ ID NO: 14. In this embodiment, the VH may comprise the amino acid sequence of SEQ ID NO: 13 wherein X in position 5 is V. In some embodiments, the VH may also comprise the amino acid sequence of SEQ ID NO: 13, wherein X in position 50 is Y, X in position 59 is Y, and/or X in position 61 is A. The VL may comprise the amino acid sequence of SEQ ID NO: 14, wherein X in position 3 is V, and/or X in position 4 is M. In some embodiments, the VL comprises V in position 3 and M in position 4. In certain embodiments, the VL may also comprise the amino acid sequence of SEQ ID NO: 14 wherein X in position 55 is Y.

In one embodiment, the anti-PD-1 antibody has a VH and VL that comprise the VH and VL amino acid sequences, respectively, of antibody 18325, i.e., where the VH comprises the amino acid sequence of SEQ ID NO: 15 and the VL comprises the amino acid sequence of SEQ ID NO: 16. In this embodiment, the VH may comprise the amino acid sequence of SEQ ID NO: 15, wherein X in position 1 is E, X in position 5 is V, and/or X in position 6 is E. In some embodiments, the VH comprises E in position 1, V in position 5 and E in position 6. In certain embodiments, the VH may also comprise the amino acid sequence of SEQ ID NO: 15, wherein X in position 35 is S, X in position 49 is S, X in position 50 is A, X in position 73 is D, and/or X in position 78 is T. The VL may comprise the amino acid sequence of SEQ ID NO: 16, wherein X in position 1 is D, X in position 3 is Q, and/or X in position 4 is M. In some embodiments, the VL comprises D in position 1, Q in position 3 and M in position 4.

In one embodiment, the anti-PD-1 antibody has a VH and VL that comprise the VH and VL amino acid sequences, respectively, of antibody 18366, i.e., where the VH comprises the amino acid sequence of SEQ ID NO: 17 and the VL comprises the amino acid sequence of SEQ ID NO: 18. In this embodiment, the VH may comprise the amino acid sequence of SEQ ID NO: 17, wherein X in position 1 is E, and/or X in position 6 is E. In some embodiments, the VH comprises E in position 1 and E in position 6. The VL may comprise the amino acid sequence of SEQ ID NO: 18 wherein X in position 1 is D. In certain embodiments, the VL may also comprise the amino acid sequence of SEQ ID NO: 18 wherein X in position 40 is A, and/or X in position 55 is Y.

In one embodiment, the anti-PD-1 antibody has a VH and VL that comprise the VH and VL amino acid sequences, respectively, of antibody 18400, i.e., where the VH comprises the amino acid sequence of SEQ ID NO: 19 and the VL comprises the amino acid sequence of SEQ ID NO: 20. In this embodiment, the VH may comprise the amino acid sequence of SEQ ID NO: 19 wherein X in position 2 is V. In certain embodiments, the VH may also comprise the amino acid sequence of SEQ ID NO: 19, wherein X in position 43 is G, X in position 49 is I, X in position 59 is N, X in position 70 is I, and/or X in position 111 is Q. The VL may comprise the amino acid sequence of SEQ ID NO: 20, wherein X in position 1 is A, and/or X in position 3 is Q. In some embodiments, the VL comprises A in position 1 and Q in position 3. In certain embodiments, the VL may also comprise the amino acid sequence of SEQ ID NO: 20, wherein X in position 10 is S.

In one embodiment, the anti-PD-1 antibody has a VH and VL that comprise the VH and VL amino acid sequences, respectively, of antibody 18413, i.e., where the VH comprises the amino acid sequence of SEQ ID NO: 21 and the VL comprises the amino acid sequence of SEQ ID NO: 22. In this embodiment, the VH may comprise the amino acid sequence of SEQ ID NO: 21, wherein X in position 48 is V, and/or X in position 50 is A. The VL may comprise the amino acid sequence of SEQ ID NO: 22 wherein X in position 4 is M. In certain embodiments, the VL may also comprise the amino acid sequence of SEQ ID NO: 22, wherein X in position 12 is S.

In one embodiment, the anti-PD-1 antibody has a VH and VL that comprise the VH and VL amino acid sequences, respectively, of antibody 18483, i.e., where the VH comprises the amino acid sequence of SEQ ID NO: 23 and the VL comprises the amino acid sequence of SEQ ID NO: 24. In this embodiment, the VH may comprise the amino acid sequence of SEQ ID NO: 23, wherein X in position 1 is E, X in position 5 is V, and/or X in position 6 is E. In some embodiments, the VL comprises E in position 1, V in position 5 and E in position 6. In certain embodiments, the VH may also comprise the amino acid sequence of SEQ ID NO: 23, wherein X in position 35 is S. The VL may comprise the amino acid sequence of SEQ ID NO: 24 wherein X in position 3 is V. In certain embodiments, the VL may also comprise the amino acid sequence of SEQ ID NO: 24, wherein X in position 40 is A, and/or X in position 55 is Y.

In certain embodiments, the anti-PD-1 antibody or antigen-binding portion comprises the H-CDR1-3 and L-CDR1-3 amino acid sequences of an antibody selected from 18040, 18049, 18098, 18113, 18201, 18247, 18250, 18325, 18366, 18400, 18413, and 18483, and further utilizes the same heavy and/or light chain germline sequences as the selected antibody.

In certain embodiments, the anti-PD-1 antibody or antigen-binding portion comprises the H-CDR1-3 and L-CDR1-3 amino acid sequences of an antibody selected from 18040, 18049, 18098, 18113, 18201, 18247, 18250, 18325, 18366, 18400, 18413, and 18483, and further comprises framework regions (FRs) that are 80%, 85%, 90%, 91%, 92%, 93%, 94%, 95%, 96%, 97%, 98%, or 99% identical to the FRs of the selected antibody.

In some embodiments, any of the anti-PD-1 antibodies or antigen-binding portions described herein may inhibit binding of PD-L1 or PD-L2, or both, to PD-1.

In some embodiments, any of the anti-PD-1 antibodies or antigen-binding portions described herein may have at least one of the following properties:
a) binds to cynomolgus PD-1 with a $K_D$ of, for example, $4 \times 10^{-8}$ M or less;
b) binds to mouse PD-1 with a $K_D$ of, for example, $2 \times 10^{-8}$ M or less;
c) binds to human PD-1 with a $K_D$ of $3 \times 10^{-9}$ M or less;
d) inhibits the interaction of PD-1 with PD-L1 at a concentration of 10 µg/ml;
e) stimulates IL-2 production in an SEB whole blood assay; and
f) stimulates IFN-γ production in a one-way mixed lymphocyte reaction assay. In some embodiments, any of the anti-PD1 antibodies or antigen-binding portions described herein may bind to human PD-1 with a $K_D$ of $5 \times 10^{-9}$ M or less, $4 \times 10^{-9}$ M or less, $3 \times 10^{-9}$ M or less, $2 \times 10^{-9}$ M or less, $1 \times 10^{-9}$ M or less, $9 \times 10^{-10}$ M or less, $8 \times 10^{-10}$ M or less, $7 \times 10^{-10}$ M or less, $6 \times 10^{-10}$ M or less, $5 \times 10^{-10}$ M or less, $4 \times 10^{-10}$ M or less, $3 \times 10^{-10}$ M or less, $2 \times 10^{-10}$ M or less, or $1 \times 10^{-10}$ M or less. In certain embodiments, the $K_D$ is determined using surface plasmon resonance.

In some embodiments, any of the anti-PD1 antibodies or antigen-binding portions described herein may inhibit the interaction of PD-1 with PD-L1 at a concentration of 50, 40, 30, 20, 10, 9, 8, 7, 6, 5, 4, 3, 2, or 1 µg/ml.

The class of an anti-PD-1 antibody obtained by the methods described herein may be changed or switched with another class or subclass. In one aspect of the invention, a nucleic acid molecule encoding VL or VH is isolated using methods well-known in the art such that it does not include nucleic acid sequences encoding CL or CH. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH chain, as described above. For example, an anti-PD-1 antibody that was originally IgM may be class switched to IgG. Further, the class switching may be used to convert one IgG subclass to another, e.g., from IgG1 to IgG2. A κ light chain constant region can be changed, e.g., to a λ light chain constant region. A preferred method for producing an antibody of the invention with a desired Ig isotype comprises the steps of isolating a nucleic acid molecule encoding the heavy chain of an anti-PD-1 antibody and a nucleic acid molecule encoding the light chain of an anti-PD-1 antibody, obtaining the variable domain of the heavy chain, ligating the variable domain of the heavy chain with the constant region of a heavy chain of the desired isotype, expressing the light chain and the ligated heavy chain in a cell, and collecting the anti-PD-1 antibody with the desired isotype.

The anti-PD-1 antibody of the invention can be an IgG, an IgM, an IgE, an IgA, or an IgD molecule, but is typically of the IgG isotype, e.g., of IgG subclass IgG1, IgG2a or IgG2b, IgG3, or IgG4. In one embodiment, the antibody is an IgG1. In another embodiment, the antibody is an IgG4.

In one embodiment, the anti-PD-1 antibody may comprise at least one mutation in the Fc region. A number of different Fc mutations are known, where these mutations provide altered effector function. For example, in many cases it will be desirable to reduce or eliminate effector function, e.g., where ligand/receptor interactions are undesired or in the case of antibody-drug conjugates.

In one embodiment, the anti-PD-1 antibody comprises at least one mutation in the Fc region that reduces effector function. Fc region amino acid positions that may be advantageous to mutate in order to reduce effector function include one or more of positions 228, 233, 234 and 235, where amino acid positions are numbered according to the IMGT numbering scheme.

In one embodiment, one or both of the amino acid residues at positions 234 and 235 may be mutated, for example from Leu to Ala (L234A/L235A). These mutations reduce effector function of the Fc region of IgG1 antibodies. Additionally or alternatively, the amino acid residue at position 228 may be mutated, for example to Pro. In some embodiments, the amino acid residue at position 233 may be mutated, e.g., to Pro, the amino acid residue at position 234 may be mutated, e.g., to Val, and/or the amino acid residue at position 235 may be mutated, e.g., to Ala. The amino acid positions are numbered according to the IMGT® numbering scheme.

In some embodiments, where the antibody is of the IgG4 subclass, it may comprise the mutation S228P, i.e., having a proline in position 228, where the amino acid position is numbered according to the IMGT® numbering scheme. This mutation is known to reduce undesired Fab arm exchange.

In certain embodiments, an antibody or antigen-binding portion thereof of the invention may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., Human Antibodies and Hybridomas 6:93-101 (1995)) and use of a cysteine residue, a marker peptide and a C-terminal polyhistidine tag to make bivalent and biotinylated scFv molecules (Kipriyanov et al., Mol. Immunol. 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an anti-PD-1 antibody of the invention linked to another polypeptide. In certain embodiments, only the variable domains of the anti-PD-1 antibody are linked to the polypeptide. In certain embodiments, the VH domain of an anti-PD-1 antibody is linked to a first polypeptide, while the VL domain of an anti-PD-1 antibody is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence (Gly4-Ser)3 (SEQ ID NO: 115), such that the VH and VL sequences can be expressed as a contiguous single-chain protein, with the VL and VH domains joined by the flexible linker. See, e.g., Bird et al., Science 242:423-426 (1988); Huston et al., Proc. Natl. Acad. Sci. USA 85:5879-5883 (1988); and McCafferty et al., Nature 348:552-554 (1990). The single chain antibody may be monovalent, if only a single VH and VL are used; bivalent, if two VH and VL are used; or polyvalent, if more than two VH and VL are used. Bi-specific or polyvalent antibodies may be generated that bind specifically to human PD-1 and to another molecule, for instance.

In other embodiments, other modified antibodies may be prepared using anti-PD-1 antibody-encoding nucleic acid molecules. For instance, "kappa bodies" (Ill et al., Protein Eng. 10:949-57 (1997)), "minibodies" (Martin et al., EMBO J. 13:5303-9 (1994)), "diabodies" (Holliger et al., Proc. Natl. Acad. Sci. USA 90:6444-6448 (1993)), or "Janusins" (Traunecker et al., EMBO J. 10:3655-3659 (1991) and Traunecker et al., Int. J. Cancer (Suppl.) 7:51-52 (1992)) may be prepared using standard molecular biological techniques following the teachings of the specification.

An anti-PD-1 antibody or antigen-binding portion of the invention can be derivatized or linked to another molecule (e.g., another peptide or protein). In general, the antibodies or portions thereof are derivatized such that PD-1 binding is not affected adversely by the derivatization or labeling. Accordingly, the antibodies and antibody portions of the invention are intended to include both intact and modified forms of the human anti-PD-1 antibodies described herein. For example, an antibody or antibody portion of the invention can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Il.

An anti-PD-1 antibody can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody according to the present invention may also be labeled. As used herein, the terms "label" or "labeled" refer to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies of the invention may be present in a neutral form (including zwitter ionic forms) or as a positively or negatively-charged species. In some embodiments, the antibodies may be complexed with a counterion to form a pharmaceutically acceptable salt.

The term "pharmaceutically acceptable salt" refers to a complex comprising one or more antibodies and one or more counterions, wherein the counterions are derived from pharmaceutically acceptable inorganic and organic acids and bases.

Bi-specific Binding Molecules

In a further aspect, the invention provides a bi-specific binding molecule having the binding specificity of an anti-PD-1 antibody described herein and the binding specificity of another anti-PD-1 antibody (e.g., another anti-PD-1 antibody described herein) or an antibody that targets a different protein, such as another immune checkpoint protein, a cancer antigen, or another cell surface molecule whose activity mediates a disease condition such as cancer. Such bi-specific binding molecules are known in the art, and examples of different types of bi-specific binding molecules are given elsewhere herein.

Nucleic Acid Molecules and Vectors

The present invention also provides nucleic acid molecules and sequences encoding anti-PD-1 antibodies or antigen-binding portions thereof described herein. In some embodiments, different nucleic acid molecules encode the heavy chain and light chain amino acid sequences of the anti-PD-1 antibody or an antigen-binding portion thereof. In other embodiments, the same nucleic acid molecule encodes the heavy chain and light chain amino acid sequences of the anti-PD-1 antibody or an antigen-binding portion thereof.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single and double stranded forms.

In any of the above embodiments, the nucleic acid molecules may be isolated.

In a further aspect, the present invention provides a vector suitable for expressing one of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode the heavy chain of an anti-PD-1 antibody of the invention or an antigen-binding portion thereof, the light chain of an anti-PD-1 antibody of the invention or an antigen-binding portion thereof, or both the heavy and light chains of an anti-PD-1 antibody of the invention or an antigen-binding portion thereof. The invention further provides vectors comprising nucleic acid molecules encoding fusion proteins, modified antibodies, antibody fragments, and probes thereof.

A nucleic acid molecule encoding the heavy and/or light chain of an anti-PD-1 antibody or antigen-binding portion thereof of the invention can be isolated from any source that produces such an antibody or portion. In various embodiments, the nucleic acid molecules are isolated from B cells that express an anti-PD-1 antibody isolated from an animal immunized with a human PD-1 antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule of the invention can be synthesized rather than isolated.

In some embodiments, a nucleic acid molecule of the invention can comprise a nucleotide sequence encoding a VH domain from an anti-PD-1 antibody or antigen-binding portion of the invention joined in-frame to a nucleotide sequence encoding a heavy chain constant region from any source. Similarly, a nucleic acid molecule of the invention can comprise a nucleotide sequence encoding a VL domain from an anti-PD-1 antibody or antigen-binding portion of the invention joined in-frame to a nucleotide sequence encoding a light chain constant region from any source.

In a further aspect of the invention, nucleic acid molecules encoding the variable domain of the heavy (VH) and/or light (VL) chains may be "converted" to full-length antibody genes. In one embodiment, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL region using standard molecular biological techniques. Nucleic acid molecules encoding the full-length heavy and/ or light chains may then be expressed from a cell into which they have been introduced and the anti-PD-1 antibody isolated.

The nucleic acid molecules may be used to recombinantly express large quantities of anti-PD-1 antibodies. The nucleic acid molecules also may be used to produce chimeric antibodies, bi-specific antibodies, single chain antibodies, immunoadhesins, diabodies, mutated antibodies and antibody derivatives, as described herein.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-PD-1 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of the anti-PD-1 antibodies or antigen-binding portions thereof of the invention as described herein.

In another embodiment, the nucleic acid molecules and vectors may be used to make mutated anti-PD-1 antibodies. The antibodies may be mutated in the variable domains of the heavy and/or light chains, e.g., to alter a binding property of the antibody. For example, a mutation may be made in one or more of the CDRs to increase or decrease the $K_D$ of the anti-PD-1 antibody, to increase or decrease $k_{off}$, or to alter the binding specificity of the antibody. In another embodiment, one or more mutations are made at an amino acid residue that is known to be changed compared to the germline in a monoclonal antibody of the invention. The mutations may be made in a CDR or framework region of a variable domain, or in a constant region. In a preferred embodiment, the mutations are made in a variable domain. In some embodiments, one or more mutations are made at an amino acid residue that is known to be changed compared to the germline in a CDR or framework region of a variable domain of an antibody or antigen-binding portion thereof of the invention.

In another embodiment, the framework region(s) are mutated so that the resulting framework region(s) have the amino acid sequence of the corresponding germline gene. A mutation may be made in a framework region or constant region to increase the half-life of the anti-PD-1 antibody. See, e.g., PCT Publication WO 00/09560. A mutation in a framework region or constant region also can be made to alter the immunogenicity of the antibody, and/or to provide a site for covalent or non-covalent binding to another molecule. According to the invention, a single antibody may have mutations in any one or more of the CDRs or framework regions of the variable domain or in the constant region.

In some embodiments, the anti-PD-1 antibodies of the invention or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody coding sequence may be ligated into a vector such that transcriptional and translational control sequences within the vector serve their intended function of regulating the transcription and translation of the antibody coding sequence. The expression vector and expression control sequences may be chosen to be compatible with the expression host cell used. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Host Cells and Methods of Antibody and Antibody Composition Production

An additional aspect of the invention relates to methods for producing the antibody compositions and antibodies and antigen-binding portions thereof of the invention. One embodiment of this aspect of the invention relates to a method for producing an antibody as defined herein, comprising providing a recombinant host cell capable of expressing the antibody, cultivating said host cell under conditions suitable for expression of the antibody, and isolating the resulting antibody. Antibodies produced by such expression in such recombinant host cells are referred to herein as "recombinant antibodies." The invention also provides progeny cells of such host cells, and antibodies produced by same.

The term "recombinant host cell" (or simply "host cell"), as used herein, means a cell into which a recombinant expression vector has been introduced. The invention provides host cells that may comprise, e.g., a vector according to the invention described above. The invention also provides host cells that comprise, e.g., a nucleotide sequence encoding the heavy chain or an antigen-binding portion thereof, a nucleotide sequence encoding the light chain or an antigen-binding portion thereof, or both, of an anti-PD-1 antibody or antigen-binding portion thereof of the invention. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-PD-1 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected by determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention or antigen-binding portions thereof from production cell lines can be enhanced using a number of known techniques. For example, the glutamine synthetase gene expression system (the GS system) is a common approach for enhancing expression under certain conditions. The GS system is discussed in whole or part in connection with EP Patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein, are part of the instant invention, regardless of the glycosylation state of the antibodies, and more generally, regardless of the presence or absence of post-translational modification(s).

Pharmaceutical Compositions

Another aspect of the invention is a pharmaceutical composition comprising as an active ingredient (or as the sole active ingredient) an anti-PD-1 antibody or antigen-binding portion thereof or anti-PD-1 antibody composition of the invention. The pharmaceutical composition may comprise any anti-PD-1 antibody composition or antibody or antigen-binding portion thereof as described herein. In some embodiments, the compositions are intended for amelioration, prevention, and/or treatment of a PD-1-related disorder and/or cancer. As used herein, a PD-1-related or -mediated disorder refers to a disorder, disease or condition that improves, or slows down in its progression, by modulation of PD-1 activity. In some embodiments, the compositions are intended for activation of the immune system. In certain embodiments, the compositions are intended for amelioration, prevention, and/or treatment of cancer originating in tissues such as skin, lung, intestine, colon, ovary, brain, prostate, kidney, soft tissues, the hematopoietic system, head and neck, liver, bladder, breast, stomach, uterus and pancreas.

Generally, the antibodies, antigen-binding portions thereof, and bi-specific binding molecules of the invention are suitable to be administered as a formulation in association with one or more pharmaceutically acceptable excipient(s), e.g., as described below.

Pharmaceutical compositions of the invention will comprise one or more anti-PD-1 antibodies or binding portions or bi-specific binding molecules of the invention, e.g., one or two anti-PD-1 antibodies, binding portions, or bi-specific binding molecules. In one embodiment, the composition comprises a single anti-PD-1 antibody of the invention or binding portion thereof.

In another embodiment, the pharmaceutical composition may comprise at least one anti-PD-1 antibody or antigen-binding portion thereof, e.g., one anti-PD-1 antibody or portion, and one or more additional antibodies that target one or more relevant cell surface receptors, e.g. one or more cancer-relevant receptors.

The term "excipient" is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and antigen-binding portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Particular embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-PD-1 antibody or antigen-binding portion thereof, bi-specific binding molecule, or anti-PD-1 antibody composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antibody of the invention per actuation and the actuation volume may for example vary from 1 μL to 100 μL.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses of Antibodies and Compositions of the Invention

In one aspect, the anti-PD-1 antibodies and antigen-binding portions thereof, anti-PD-1 compositions, and bi-specific binding molecules of the invention are used to enhance or activate the immune system in a human in need thereof. In some embodiments, the patient is immune-suppressed. For example, a physician can boost the anti-cancer activity of a patient's own immune system by administering an anti-PD-1 antibody, antibody-binding portion, composition, or bi-specific binding molecule of the present invention, alone or in combination with other therapeutic agents (sequentially or concurrently). The anti-PD-1 antibody or portion, composition, or bi-specific binding molecule modulates the activity of PD-1 in immune cells, resulting in enhancement of anti-cancer immunity. In certain embodiments, the antibody or antigen-binding portion thereof, composition, or bi-specific binding molecule is for use in the treatment of cancer, e.g., cancers that originate in tissues such as skin, lung, intestine, colon, ovary, brain, prostate, kidney, soft tissues, the hematopoietic system, head and neck, liver, bladder, breast, stomach, uterus and pancreas, and any cancers or other conditions which rely on PD-1 activity and/or in which the patient expresses or overexpresses PD1, PD-L1, and/or PD-L2. Cancers treated by the anti-PD-1 antibodies, antigen-binding portions thereof, anti-PD-1 compositions, and/or bi-specific binding molecules of the invention may include, e.g., melanoma (such as advanced melanoma, or unresectable or metastatic melanoma), non-small cell lung cancer, bladder cancer, head and neck squamous cell carcinoma, ovarian cancer, colorectal cancer, gastric cancer, microsatellite instability-high cancer, hepatocellular carcinoma, mesothelioma, Merkel cell carcinoma, glioma, multiple myeloma, diffuse large B cell lymphoma, Hodgkin's lymphoma, and renal cell carcinoma (RCC).

In some embodiments, cancers treated by the anti-PD-1 antibodies, antigen-binding portions, anti-PD-1 compositions, and/or bi-specific binding molecules of the invention may include, e.g., advanced or metastatic melanoma, non-small cell lung cancer, head and neck squamous cell cancer, renal cell carcinoma, Hodgkin's lymphoma, non-Hodgkin's lymphoma, glioblastoma, glioma, neuroendocrine tumors, squamous cell lung cancer, small-cell lung cancer, hepatocellular carcinoma, bladder cancer, upper urinary tract cancer, esophageal cancer, gastroesophageal junction cancer, gastric cancer, liver cancer, colon cancer, colorectal carcinoma, multiple myeloma, sarcomas, acute myeloid leukemia, chronic myeloid leukemia, myelodysplastic syndrome, nasopharyngeal cancer, chronic lymphocytic leukemia, acute lymphoblastic leukemia, small lymphocytic lymphoma, ovarian cancer, gastrointestinal cancer, primary peritoneal cancer, fallopian tube cancer, urothelial cancer, HTLV-associated T-cell leukemia/lymphoma, prostate cancer, genitourinary cancer, meningioma, adrenocortical cancer, gliosarcoma, kidney cancer, breast cancer, pancreatic cancer, endometrial cancer, skin basal cell cancer, cancer of the appendix, biliary tract cancer, salivary gland cancer, advanced Merkel cell cancer, urological cancer, bone cancer, thoracic cancer, respiratory tract cancer, adenoid cystic carcinoma, cervical cancer, astrocytoma, chordoma, hematologic neoplasms, neuroblastoma, oral cavity cancer, cutaneous squamous cell carcinoma, thyroid cancer, Kaposi sarcoma, anal cancer, gallbladder cancer, thymic cancer, uterine cancer, diffuse large B cell lymphoma, follicular lymphoma, mesothelioma, or solid tumors. The cancer may be, e.g., at an early, intermediate, late, or metastatic stage.

In some embodiments, the anti-PD-1 antibodies, antigen-binding portions, compositions, and/or bi-specific binding molecules of the invention may be used to treat viral and/or parasitic infections, e.g., where the pathogens inhibit the host immune response. For example, the pathogen may be, e.g., HIV, hepatitis (A, B, or C), human papilloma virus (HPV), lymphocytic choriomeningitis virus (LCMV), adenovirus, flavivirus, echovirus, rhinovirus, coxsackie virus, cornovirus, respiratory syncytial virus, mumps virus, rotavirus, measles virus, rubella virus, parvovirus, vaccinia virus, human T-cell lymphotrophic virus (HTLV), dengue virus, molluscum virus, poliovirus, rabies virus, John Cunningham (JC) virus, arboviral encephalitis virus, simian immunodeficiency virus (Sly), influenza, herpes, Giardia, malaria, *Leishmania, Staphylococcus aureus*, or *Pseudomonas aeruginosa*.

In some embodiments, the anti-PD-1 antibodies, antigen-binding portions, compositions, and/or bi-specific binding molecules of the invention may be used to treat a patient who is, or is at risk of being, immunocompromised (e.g., due to chemotherapeutic or radiation therapy).

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in tumor shrinkage, increased survival, elimination of cancer cells, decreased disease progression, reversal of metastasis, or other clinical endpoints desired by healthcare professionals.

The anti-PD-1 antibodies or antigen-binding portions thereof, compositions, or bi-specific binding molecules of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the antibodies and antigen-binding portions thereof, compositions, and bi-specific binding molecules of the invention with one or more other therapeutic agents, is intended to mean, and does refer to and include the following:

simultaneous administration of such combination of antibody/antigen-binding portion/antibody composition/bi-specific binding molecule of the invention and therapeutic agent(s) to a patient in need of treatment, when such components are formulated together into a single dosage form which releases said components at substantially the same time to said patient, substantially simultaneous administration of such combination of antibody/antigen-binding portion/antibody composition/bi-specific binding molecule of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of antibody/antigen-binding portion/antibody composition/bi-specific binding molecule of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of antibody/antigen-binding portion/antibody composition/bi-specific binding molecule of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The antibodies and antigen-binding portions thereof, antibody compositions, and bi-specific binding molecules of the invention may be administered without additional therapeutic treatments, i.e., as a stand-alone therapy (monotherapy). Alternatively, treatment with the antibodies and antigen-binding portions thereof, compositions, and bi-specific binding molecules of the invention may include at least one additional therapeutic treatment (combination therapy), e.g., another immunostimulatory agent, an anti-cancer agent, an anti-viral agent, or a vaccine (e.g., a tumor vaccine). In some embodiments, the antibody or antigen-binding portion thereof, composition, or bi-specific binding molecule may be co-administered or formulated with another medication/drug for the treatment of cancer. The additional therapeutic treatment may comprise, e.g., a chemotherapeutic, anti-neoplastic, or anti-angiogenic agent, a different anti-cancer antibody, and/or radiation therapy.

By combining the antibodies, antigen-binding portions, compositions, or bi-specific binding molecules of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. In some embodiments, the compound is selected from the group consisting of retinoic acid, phenylbutyrate, all-trans-retinoic acid and active form vitamin D.

Pharmaceutical articles comprising an anti-PD-1 antibody or antigen-binding portion thereof, composition, or bi-specific binding molecule of the invention and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, e.g., fluorouracil and/or other fluoropyrimidines.

An anti-PD-1 antibody or antigen-binding portion thereof, antibody composition, or bi-specific binding molecule of the invention may also be used in combination with other anti-cancer therapies such as vaccines, cytokines, enzyme inhibitors, immunostimulatory compounds, and T cell therapies. In the case of a vaccine, it may, e.g., be a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example 1-methyl-D-tryptophan (1-D-MT). Adoptive T cell therapy refers to various immunotherapy techniques that involve expanding or engineering patients' own T cells to recognize and attack their tumors.

It is also contemplated that an anti-PD-1 antibody or antigen-binding portion thereof, antibody composition, or bi-specific binding molecule of the invention may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation by competing for the intracellular Mg-ATP binding site.

In some embodiments, the antibody or antigen-binding portion thereof, composition, or bi-specific binding molecule may be used in combination with another medication/drug that mediates immune system activation, including, but not limited to, an agent that modulates the expression or activity of A2AR, BTLA, B7-H3, B7-H4, CTLA-4, CD27, CD28, CD40, CD55, CD73, CD122, CD137, CD160, CGEN-15049, CHK1, CHK2, CTLA-3, CEACAM (e.g., CEACAM-1 and/or CEACAM-5), GALS, GITR, HVEM, ICOS, IDO, KIR, LAIR1, LAG-3, OX40, TIGIT, TIM-3, TGFR-beta, VISTA, LILRB2, CMTM6, and/or 2B4. In certain embodiments, the agent is an antibody or an antigen-binding fragment thereof that binds to one of the above molecules. In certain embodiments, the antibody or antigen-binding portion thereof, composition, or bi-specific binding molecule of the invention may be administered in combination with a CTLA-4 inhibitor (e.g., an anti-CTLA-4 antibody such as tremelimumab or ipilimumab). In one embodiment, the antibody or antigen-binding portion thereof, composition, or bi-specific binding molecule of the invention may be administered in combination with ipilimumab.

In certain aspects, the antibodies and antigen-binding portions, compositions, and bi-specific binding molecules of the invention may be administered in combination with another inhibitor of the PD-1 pathway, which may target PD-1 or one or more of its ligands. Examples of such inhibitors include other anti-PD-1 antibodies, anti-PD-L1 antibodies, and anti-PD-L2 antibodies. In some embodiments, an anti-PD1 antibody or antigen-binding portion thereof, bi-specific antibody, or antibody composition of the invention may be administered in combination with pembrolizumab and/or nivolumab.

It is understood that the antibodies and antigen-binding portions thereof, antibody compositions, and bi-specific binding molecules of the invention may be used in a method of treatment as described herein, may be for use in a treatment as described herein, and/or may be for use in the manufacture of a medicament for a treatment as described herein. The invention also provides kits and articles of manufacture comprising the antibodies and antigen-binding portions thereof, antibody compositions, and/or bi-specific binding molecules described herein.

Dose and Route of Administration

The antibodies or antigen-binding portions thereof, compositions, and bi-specific binding molecules of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

It is contemplated that a suitable dose of an antibody or antigen-binding portion thereof, composition, or bi-specific binding molecule of the invention will be in the range of 0.1-100 mg/kg, such as about 0.5-50 mg/kg, e.g., about 1-20 mg/kg. The antibody, antigen-binding portion, composition, or bi-specific binding molecule may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, composition, or bi-specific binding molecule of the invention to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

Diagnostic Uses and Compositions

The antibodies of the present invention also are useful in diagnostic processes (e.g., in vitro, ex vivo). For example, the antibodies can be used to detect and/or measure the level of PD-1 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the antibodies described herein.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1. Generation and Screening of Anti-PD-1 Antibody Repertoires

Materials and Methods

OmniRat® rats (Osborn et al., *J Immunol.* 2013, 190(4): 1481-90), an engineered rat strain from OMT (Open Monoclonal Technology, Inc.) capable of producing human antibodies, were immunized with human, cynomolgus, or mouse PD-1 antigens. Cloning of antibody genes from single-cell sorted antibody-secreting B cells (ASC) derived from the rats was performed by means of the Symplex™ antibody discovery technology (Meijer et al., *J Mol Biol* 2006, 358(3):764-72; U.S. Pat. No. 7,749,697; WO 2008/104184).

A Symplex™ antibody library was prepared from single-cell sorted B cells from the immunized OMT rats, the library containing cognate VH and VL encoding pairs for each sorted B cell. The antibody repertoire expression constructs encoded fully human immunoglobulins in IgG1 format carrying two mutations (L234A/L235A) known to reduce effector function of the Fc region of IgG1 antibodies (Hezareh et al., *J Virol.* 75(24): 12161-8 (2001)).

CHO-S cells were transfected in 384-well format with expression constructs to display human, cynomolgus or mouse PD-1 using the FreeStyle™ MAX reagent (Invitrogen). Furthermore, another cell population was transfected with a control vector encoding the irrelevant protein human VEGFR2 and subsequently used as a negative control. In order to allow for a multiplexed screening setup, control cells labelled with intermediate intensity carboxyfluorescein succinimidyl ester (CFSE$^{Inter}$), cyno PD-1 transfected cells labelled with high intensity CFSE (CFSE$^{high}$), and non-labelled human PD-1-transfected cells, were mixed at a ratio of 1:1:1, at a density of 1×10E6 cells per ml. In 384-well plates, 40 µl of this cell mix was mixed with 10 µl of antibody-containing supernatant, and cell-bound antibody was revealed by addition of goat anti-human IgG (H+L) AF647 secondary antibody (Molecular Probes, Cat. No. A21445). In parallel, antibodies were screened for binding to human (CFSE$^{pos}$) and mouse PD-1 (CFSE$^{neg}$) in a similar setup. Samples were acquired using high throughput flow cytometry (iQue® Screener, Intellicyt) and data was analyzed using ForeCyt® software by plotting CFSE vs. IgG binding (AF647). PD-1-specific primary hits were identified as antibody clones binding to both human (CSFE$^{neg}$) and cynomolgus PD-1-transfected cells (CFSE$^{high}$), but not to control cells (CFSE$^{inter}$), and plate numbers and plate coordinates were collected for hit picking and subsequent sequence analysis. A number of primary hits exhibiting additional reactivity towards mouse PD-1 in the second screening (CFSE$^{neg}$) were also selected for further analysis.

Results

FIGS. 1(a)-1(d) show representative flow cytometry dot plots for four antibody clones exhibiting different reactivity towards PD-1 orthologs:
(a) an antibody clone binding non-specifically to CHO-S cells,
(b) an antibody clone binding specifically to human PD-1-transfected cells only,
(c) an antibody clone binding specifically to human and cynomolgus PD-1, and
(d) an antibody clone binding to all three PD-1 species tested in the screening.

The upper dot plots in each of (a), (b), (c) and (d) represent a first screening round testing antibodies for binding to human PD-1 (huPD1) and cynomolgus PD-1 (cynoPD1) as compared to negative control cells (neg). The lower dot plots represent a second screening round testing antibodies for binding to mouse PD-1 (moPD1) and human PD-1 (huPD1). The x-axis (horizontal) shows CFSE, and the y-axis (vertical) shows human IgG binding.

Example 2. Antibody Sequences

Screening hits were analyzed by DNA sequencing and antibody-encoding DNA sequences were extracted. 488 primary hits exhibiting cross reactivity to both human and cynomolgus PD-1 were sequenced. This revealed that the anti-PD-1 hit repertoire contained 254 unique antibodies representing 140 genetic clusters. Selected antibody clones were individually expressed and tested functionally as described below. Twelve antibodies exhibiting functional activity in in vitro assays are described hereafter. The numbering of the protein sequences of the twelve antibody VH and VL domains is shown in Table 1. Sequence numbering of the immunoglobulin constant regions (Ig heavy chain (IgHC) with L234A/L235A mutations and Ig kappa light chain (IgKV)) used to clone the variable VH and VL genes is shown in Table 2. Sequence numbering of the CDRs of the twelve functional antibodies is shown in Table 3. The CDR sequences herein were determined according to the IMGT® definitions for CDR1 and CDR2. For heavy and light chain CDR3, the definitions herein include one extra amino acid residue amino-terminal to the IMGT-CDR3 (Cys).

TABLE 1

Numbering of antibody variable domain amino acid sequences

| Antibody number | VH protein SEQ ID NO. | VL protein SEQ ID NO. |
|---|---|---|
| 18040 | 1 | 2 |
| 18049 | 3 | 4 |
| 18098 | 5 | 6 |
| 18113 | 7 | 8 |
| 18201 | 9 | 10 |
| 18247 | 11 | 12 |
| 18250 | 13 | 14 |
| 18325 | 15 | 16 |
| 18366 | 17 | 18 |
| 18400 | 19 | 20 |
| 18413 | 21 | 22 |
| 18483 | 23 | 24 |

TABLE 2

Numbering of antibody constant region DNA and amino acid sequences

| Sequence name | DNA SEQ ID NO. | Protein SEQ ID NO. |
|---|---|---|
| IgHC | 25 | 26 |
| IgKC | 27 | 28 |

TABLE 3

SEQ ID NOs for the amino acid sequences of the heavy chain CDR1, CDR2 and CDR3 and light chain CDR1 and CDR3 of anti-PD-1 antibodies

| Antibody | H-CDR1 | H-CDR2 | H-CDR3 | L-CDR1 | L-CDR2 | L-CDR3 |
|---|---|---|---|---|---|---|
| 18040 | 29 | 30 | 31 | 32 | 33 | 34 |
| 18049 | 35 | 36 | 37 | 38 | 39 | 40 |
| 18098 | 41 | 42 | 43 | 44 | 45 | 46 |
| 18113 | 29 | 47 | 48 | 49 | 50 | 51 |
| 18201 | 52 | 53 | 54 | 38 | 45 | 55 |
| 18247 | 29 | 56 | 48 | 57 | 33 | 51 |
| 18250 | 58 | 59 | 60 | 57 | 33 | 34 |
| 18325 | 61 | 62 | 43 | 44 | 45 | 46 |
| 18366 | 63 | 64 | 65 | 32 | 33 | 34 |
| 18400 | 66 | 67 | 68 | 38 | 45 | 55 |
| 18413 | 69 | 70 | 71 | 72 | 45 | 73 |
| 18483 | 74 | 75 | 76 | 57 | 33 | 34 |

Example 3. Framework Mutations in Antibody Sequences

Alignment of the VH and VL amino acid sequences of Example 2 to human germline sequences was performed to reveal the germline genes from which the VH and VL sequences originate. Table 4 shows the assignment of the closest V- and J-germline gene for VH and VL of each clone, as well as information on framework mutations as described in the following.

Since the antibody genes were isolated by RT-PCR using the Symplex™ antibody discovery technology (Mejier et al., J Mol Biol 358:764-772 (2006); WO 2005/042774) with degenerate primers, the initial six amino acids are prone to mutations that do not arise during the maturation of the antibody sequence. Hence, these primer-derived mutations can be mutated back to germline sequence without risk of reduced binding affinity. The numbers and specific amino acid substitutions of VH and VL in these "Symplex-corrected" variant sequences are shown in Table 4. Furthermore, antibodies harbouring somatic hypermutations in framework regions of variable domains, i.e., mutations in the VH or VL outside the CDRs, can be changed back to the sequence of the closest V- or J-germline. The numbers and specific amino acid substitutions in antibody frameworks that may be changed to that of germline in these "germlined" variant sequences are also shown in Table 4. It will be apparent that the "germlined" variant mutations indicated in Table 4 (see the columns "Number of VH framework mutations in germlined variant" and "Mutations of VH framework mutations in germlined variant") include any "Symplex-corrected" mutations as well as mutations outside of the initial six amino acid positions.

As noted above, alteration of degenerate primer-derived mutations in the first six amino acids in each VH or VL sequence is not expected to deteriorate the binding properties compared to the original antibody. Therefore, it is preferred that the anti-PD-1 antibodies of the invention include the "Symplex-corrected" mutations indicated in the tables below.

As for the "germlined variant" mutations that are outside the initial six amino acid positions of each sequence, any one or more of these mutations may be selected. Determination of whether an individual mutation has a negative effect on the antigen-binding properties of an antibody may be performed by preparing germlined variant VH and VL sequences with the indicated mutation and comparing the antigen-binding properties of the antibody with those of the parent with the corresponding original or Symplex-corrected sequences. In the event that a reduction in binding affinity or other altered binding property is observed, variants may, for example, be tested using a 2×2 VH/VL matrix with a Symplex-corrected variant and a germlined variant of the heavy and light chains of each antibody, i.e., in this case four combinations for each antibody. This allows determination of whether one or the other, or both, of the germlined VH and VL sequences are contributing to any observed altered binding properties. Alternatively or additionally, a series of corresponding antibodies in which single germlined variant mutations are avoided may be tested to determine specific mutations that are influencing binding of the germlined variant having all mutations listed.

Table 5 shows the VH and VL sequence numbers for the original sequences as well as the corresponding Symplex-corrected and germlined variants. It will be apparent from the numbers in Table 5 that in some cases there is no difference between the original sequence and the Symplex-corrected sequence, or between the Symplex-corrected sequence and the germlined sequence. Mutations to germline framework residues are based on the IMGT definitions. In the appended sequence listing the resulting amino acid substitutions are underlined and marked by bold type.

TABLE 4

(Part 1: VH sequence framework mutations)

| Antibody | Closest V-, J-germline | # of VH FR mutations in Symplex-corrected variant | VH FR mutations in Symplex-corrected variant | # of VH FR mutations in germlined variant | VH FR mutations in germlined variant |
|---|---|---|---|---|---|
| 18040 | IGHV3-11*01, IGHJ5*02 | 0 | | 2 | N35S, D84N |
| 18049 | IGHV3-33*04, IGHJ4*02 | 0 | | 0 | |
| 18098 | IGHV3-23*04, IGHJ3*02 | 2 | Q1E, Q5V | 9 | Q1E, Q5V, R13Q, N35S, V46E, T50A, S77N, F80Y, T115M |
| 18113 | IGHV3-11*01, IGHJ5*02 | 0 | | 1 | A64V |
| 18201 | IGHV4-4*02, IGHJ3*02 | 1 | V5Q | 4 | V5Q, T59N, R76K, M83L |
| 18247 | IGHV3-11*01, IGHJ4*02 | 0 | | 2 | D10G, R16G |
| 18250 | IGHV3-11*01, IGHJ4*03 | 1 | Q5V | 4 | Q5V, H50Y, D59Y, V61A |
| 18325 | IGHV3-23*04, IGHJ3*02 | 3 | Q1E, Q5V, Q6E | 8 | Q1E, Q5V, Q6E, N35S, A49S, T50A, G73D, M78T |
| 18366 | IGHV3-7*02, IGHJ5*02 | 2 | Q1E, Q6E | 2 | Q1E, Q6E |
| 18400 | IGHV4-4*02, IGHJ3*02 | 1 | L2V | 6 | L2V, K43G, V49I, S59N, M70I, P111Q |
| 18413 | IGHV3-23*04, IGHJ4*03 | 0 | | 2 | L48V, T50A |
| 18483 | IGHV3-7*02, IGHJ5*02 | 3 | Q1E, Q5V, Q6E | 4 | Q1E, Q5V, Q6E, N35S |

TABLE 4-continued (Part 2: VL sequence framework mutations)

| Antibody | Closest V-, J- germline | # of VL FR mutations in Symplex-corrected variant | VL FR mutations in Symplex-corrected variant | # of VL FR mutations in germlined variant | VL FR mutations in germlined variant |
|---|---|---|---|---|---|
| 18040 | IGKV4-1*01, IGKJ1*01 | 1 | E1D | 3 | E1D, F40A, F55Y |
| 18049 | IGKV1-17*01, IGKJ1*01 | 2 | E1D, V3Q | 3 | E1D, V3Q, N53S |
| 18098 | IGKV1D-2*01, IGKJ1*01 | 1 | L4M | 1 | L4M |
| 18113 | IGKV4-1*01, IGKJ1*01 | 2 | Q3V, L4M | 3 | Q3V, L4M, R69S |
| 18201 | IGKV1-6*01, IGKJ1*01 | 1 | D1A | 1 | D1A |
| 18247 | IGKV4-1*01, IGKJ1*01 | 2 | E1D, L4M | 4 | E1D, L4M, F55Y, F93Y |
| 18250 | IGKV4-1*01, IGKJ2*01 | 2 | Q3V, L4M | 3 | Q3V, L4M, S55Y |
| 18325 | IGKV1D-2*02, IGKJ1*01 | 3 | E1D, V3Q, L4M | 3 | E1D, V3Q, L4M |
| 18366 | IGKV4-1*01, IGKJ2*01 | 1 | E1D | 3 | E1D, L40A, F55Y |
| 18400 | IGKV1-6*01, IGKJ1*01 | 2 | E1A, V3Q | 3 | E1A, V3Q, P10S |
| 18413 | IGKV1D-2*01, IGKJ4*02 | 1 | L4M | 2 | L4M, P12S |
| 18483 | IGKV4-1*01, IGKJ2*01 | 1 | Q3V | 3 | Q3V, L40A, F55Y |

TABLE 5

SEQ ID NOs for the amino acid sequences of the VH and VL of anti-PD-1 antibodies, including for Symplex-corrected and germlined variants

| Antibody number | VH protein sequence number | Symplex-corrected VH variant | Germlined VH variant | VL protein sequence number | Symplex-corrected VL variant | Germlined VL variant |
|---|---|---|---|---|---|---|
| 18040 | 1 | 1 | 96 | 2 | 84 | 106 |
| 18049 | 3 | 3 | 3 | 4 | 85 | 107 |
| 18098 | 5 | 77 | 97 | 6 | 86 | 86 |
| 18113 | 7 | 7 | 98 | 8 | 87 | 108 |
| 18201 | 9 | 78 | 99 | 10 | 88 | 88 |
| 18247 | 11 | 11 | 100 | 12 | 89 | 109 |
| 18250 | 13 | 79 | 101 | 14 | 90 | 110 |
| 18325 | 15 | 80 | 102 | 16 | 91 | 91 |
| 18366 | 17 | 81 | 81 | 18 | 92 | 111 |
| 18400 | 19 | 82 | 103 | 20 | 93 | 112 |
| 18413 | 21 | 21 | 104 | 22 | 94 | 113 |
| 18483 | 23 | 83 | 105 | 24 | 95 | 114 |

Example 4. Flow Cytometric Analysis of Anti-PD-1 Antibodies for PD-L1 Blocking Activity This example describes testing of the anti-PD-1 antibodies for PD-L1 blocking activity by means of flow cytometry.
Methods
PD-L1 ligand blocking activity was investigated in a cellular assay, in which human PD-1 was recombinantly expressed on CHO-S cells, and binding of R-PE (R-phycoerythrin) labeled human PD-L1-Fc chimera protein was analyzed by flow cytometry. Commercially available recombinant PD-L1-Fc chimera protein (R&D Systems, USA) was conjugated to R-PE using the Lightning-Link® R-Phycoerythrin Conjugation Kit (Innova Biosciences, UK). The CHO-S cells were transiently transfected to express human PD-1. Cells were then incubated with 50 µl anti-PD-1 antibody at 20 µg/ml on ice, followed by addition of 50 µl R-PE-labeled PD-L1-Fc at approx. 3.4 µg/ml (16.4 nM final concentration) with further incubation for an additional 20 min (final anti-PD-1 antibody concentration: 10 µg/ml). Bound antibody was detected using APC (allophycocyanin) conjugated anti-human IgG light chain antibody. Binding of PD-L1 and anti-PD-1 antibody was quantified by flow cytometry detecting R-PE and APC fluorescence, respectively.
Results
The results of the competition experiment are presented in FIGS. 2(a)-2(h), where the X-axis (horizontal) shows PD-L1 binding, and the Y-axis (vertical) shows human IgG binding. All anti-PD-1 antibodies tested were able to inhibit the interaction of PD-1 with PD-L1 at a final antibody concentration of 10 µg/ml. Binding of PD-L1 to PD-1-expressing cells in the presence of a non-specific antibody was used as a negative control for PD-L1 blocking. In addition, a representative plot for binding of PD-L1 in the presence of a non-blocking antibody is presented.

Example 5. Measurement of PD-1 Antibody Affinities Against Human and Cynomolgus PD-1 ECD Antigen This example demonstrates how twelve functional anti-PD-1 antibodies exhibit strong binding affinity for human PD-1, with $K_D$ in the range of low nM to intermediate pM. The same antibodies also cross-react with cynomolgus PD-1 with $K_D$ in the range of intermediate to low nM. Antibodies 18201 and 18400 also cross react with mouse PD-1 with $K_D$ in the range of intermediate or low nM.

Methods

The kinetic binding analysis was performed by Surface Plasmon Resonance (SPR) using a Continuous Flow Microspotter (CFM, Wasatch Microfluidics, US) combined with an Ibis MX96 SPR instrument (IBIS Technologies, The Netherlands). Surface Plasmon Resonance imaging analysis was performed on G-a-hu-IgG Fc SensEye® SPR sensors (Ssens BV, The Netherlands). Anti-PD-1 antibodies expressed in IgG$_1$ LALA format (i.e., having the mutations L234A/L235A) were diluted to 2.5 nM in PBS-T (1×PBS with 0.05% Tween 20, pH 7.4). Antibodies were spotted onto a G-a-hu-IgG Fc SensEye® for 15 minutes using a Continuous Flow Microspotter (CFM, Wasatch Microfluidics, Salt Lake City, US). After spotting, the SensEye® was positioned in the *IBIS* MX96 biosensor, and antibodies were chemically fixed to the sensor surface using Fix It Kit (Ssens BV, The Netherlands). Kinetic analysis was performed by applying a kinetic titration series (Karlsson et. al., Anal. Biochem. 349(1):136-47 (2006)), where monomeric PD-1 antigen was injected in increasing concentrations from 2 nM to 100 nM without application of surface regeneration steps after each antigen injection. Binding was tested to human PD-1 ECD (Acro Biosystems cat. no. PD1-H52219), mouse PD-1 ECD (Sino Biological. cat. no. 50124-MO8H) and cynomolgus PD-1 ECD (Acro Biosystems cat. no. PD1-05223) in three separate experiments. Antigen association was performed for 15 minutes and antigen dissociation was performed for 60 minutes. The kinetic analysis was performed at 25° C. After completion, the recorded binding responses were fitted to a simple Langmuir 1:1 binding model with Scrubber 2 software for calculation of the on-rate ($k_{on}$ or $k_a$), off-rate ($k_{off}$ or $k_d$) and affinity ($K_D$) constants.

Results

The Surface Plasmon Resonance (SPR) results are shown below in Table 6. Generally, antibodies were of high affinity and all tested antibodies cross-reacted with cynomolgus PD-1. Antibodies 18201 and 18400 also cross-reacted with mouse PD-1, indicating that the epitopes recognized by these two antibodies were unique as compared to the other PD-1 antibodies, including the reference antibodies, pembrolizumab and nivolumab, which did not cross-react with mouse PD-1. These properties are advantageous because they allow the antibodies to be directly tested in non-human primate or murine models prior to testing in human subjects.

TABLE 6

Kinetics of anti-PD-1 antibodies' binding to human, cynomolgus or mouse PD-1 ECD as measured by Surface Plasmon Resonance (SPR).

| Antibody | PD-1 ECD | $k_{on}$ (M$^{-1}$s$^{-1}$) | $k_{off}$ (s$^{-1}$) | $K_D$ (M) |
|---|---|---|---|---|
| 18040 | Human | 2.6E+05 | 1.1E−04 | 4.1E−10 |
| 18040 | Cynomolgus | 3.4E+05 | 9.7E−04 | 2.9E−09 |
| 18040 | Mouse | N.B. | N.B. | N.B. |
| 18049 | Human | 3.4E+04 | 6.0E−05 | 1.8E−09 |
| 18049 | Cynomolgus | 3.8E+04 | 8.0E−05 | 2.1E−09 |
| 18049 | Mouse | N.B. | N.B. | N.B. |
| 18098 | Human | 1.0E+05 | 2.3E−04 | 2.3E−09 |
| 18098 | Cynomolgus | 3.9E+04 | 1.3E−03 | 3.4E−08 |
| 18098 | Mouse | N.B. | N.B. | N.B. |
| 18113 | Human | 1.7E+05 | 1.0E−04 | 6.0E−10 |
| 18113 | Cynomolgus | 1.4E+05 | 7.6E−04 | 5.3E−09 |
| 18113 | Mouse | N.B. | N.B. | N.B. |
| 18201 | Human | 2.9E+05 | 1.3E−04 | 4.3E−10 |
| 18201 | Cynomolgus | 1.9E+05 | 2.3E−04 | 1.2E−09 |
| 18201 | Mouse | 3.8E+04 | 7.3E−05 | 1.9E−09 |
| 18247 | Human | 1.1E+05 | 1.5E−04 | 1.4E−09 |
| 18247 | Cynomolgus | 9.8E+04 | 2.7E−03 | 2.8E−08 |
| 18247 | Mouse | N.B. | N.B. | N.B. |
| 18250 | Human | 3.5E+05 | 2.9E−04 | 8.3E−10 |
| 18250 | Cynomolgus | 2.8E+05 | 1.8E−03 | 6.4E−09 |
| 18250 | Mouse | N.B. | N.B. | N.B. |
| 18325 | Human | 1.3E+05 | 1.1E−04 | 8.2E−10 |
| 18325 | Cynomolgus | 1.4E+05 | 6.2E−04 | 4.3E−09 |
| 18325 | Mouse | N.B. | N.B. | N.B. |
| 18366 | Human | 3.0E+05 | 4.0E−04 | 1.3E−09 |
| 18366 | Cynomolgus | 2.2E+05 | 6.4E−03 | 2.9E−08 |
| 18366 | Mouse | N.B. | N.B. | N.B. |
| 18400 | Human | 2.3E+05 | 3.5E−04 | 1.6E−09 |
| 18400 | Cynomolgus | 2.3E+05 | 8.7E−04 | 3.7E−09 |
| 18400 | Mouse | 4.7E+03 | 5.0E−05 | 1.1E−08 |
| 18413 | Human | 7.7E+04 | 1.1E−04 | 1.5E−09 |
| 18413 | Cynomolgus | 9.7E+04 | 6.2E−04 | 6.4E−09 |
| 18413 | Mouse | N.B. | N.B. | N.B. |
| 18483 | Human | 5.8E+05 | 1.7E−04 | 2.9E−10 |
| 18483 | Cynomolgus | 2.6E+05 | 8.0E−04 | 3.1E−09 |
| 18483 | Mouse | N.B. | N.B. | N.B. |
| nivolumab analogue | Human | 2.4E+05 | 1.9E−04 | 8.0E−10 |
| nivolumab analogue | Cynomolgus | 4.1E+05 | 6.2E−04 | 1.5E−09 |
| nivolumab analogue | Mouse | N.B. | N.B. | N.B. |
| pembrolizumab/ Keytruda | Human | 4.2E+05 | 1.4E−03 | 3.4E−09 |
| pembrolizumab/ Keytruda | Cynomolgus | 3.5E+05 | 1.3E−03 | 3.6E−09 |
| pembrolizumab/ Keytruda | Mouse | N.B. | N.B. | N.B. |

(N.B. = not binding)

Example 6. In Vitro Functional Evaluation of Anti-PD-1 Monoclonal Antibodies This example demonstrates how the twelve anti-PD-1 antibodies perform in two different functional assays: the Staphylococcal Enterotoxin B (SEB) whole blood assay and a one-way mixed lymphocyte reaction (MLR). The ability of the twelve anti-PD-1 mAbs to stimulate IL-2 production in the SEB treated whole blood assay or interferon-gamma (IFN-γ) production in the one-way MLR assay was evaluated as described below.

Methods

SEB is a super-antigen that binds to MHC class II molecules and specific Vβ regions of T cell receptors (TCR) and drives non-specific stimulation of T-cells. This results in polyclonal T cell activation/proliferation and cytokine release, including IL-2 and IFN-γ. SEB was added at 1 µg/ml to whole blood, and after two days of culture, supernatants were harvested and IL-2 levels were determined by regular ELISA.

In the one-way MLR assay, dendritic cells (DCs) and CD4-positive (CD4+) T-cells isolated from two different healthy donors were co-cultured to induce an alloantigen specific reaction, resulting in cytokine production and T-cell activation/proliferation. Dendritic cells were differentiated from CD14+ monocytes by six days of culture with 20 ng/ml granulocyte-macrophage colony-stimulating factor (GM-CSF) and 20 ng/ml interleukin-4 (IL-4), and mixed in a 1:10 ratio with CD4+ T-cells isolated from peripheral blood mononuclear cells (PBMCs) from healthy donor material. After 5 days of culture, supernatants were harvested, and IFN-γ levels were determined using the Meso Scale electrochemiluminescence (MSD) cytokine assay.

Dose-response curves were generated by two-fold dilutions of the antibodies with a starting concentration of 50 µg/ml.

Results

Dose-response curves of the twelve antibodies in the SEB whole blood assay and one-way MLR assay are shown in FIGS. 3(a)-3(f) and FIGS. 4(a)-4(f), respectively. Each point on the graph represents the average of three replicates, with the error bars representing the SEM. All of the antibodies were found to induce a dose-dependent increase in IL-2 production in the SEB whole blood assay and in IFN-γ production in the MLR assay.

Example 7. Epitope Binning of Anti-PD-1 Monoclonal Antibodies

This example illustrates how anti-PD-1 antibodies were grouped into epitope bins based on paired competition patterns. Antibodies belonging to different epitope bins recognize different epitopes on the PD-1 ECD.

Methods

Investigation of paired antibody competition was performed by Surface Plasmon Resonance (SPR) analysis using a Continuous Flow Microspotter (CFM) (Wasatch Microfluidics, US) combined with an *IBIS* MX96 SPR instrument (*IBIS* Technologies, The Netherlands). Surface Plasmon Resonance imaging analysis was performed on G-a-hu-IgG Fc SensEye® SPR sensor (Ssens BV, The Netherlands). A total of eighteen anti-PD-1 antibodies (human, IgG1) were diluted to 10 µg/mL in PBS buffer containing 0.05% Tween 20 (PBS-T), pH 7.0. Antibodies were captured onto the anti-Fc sensor surface by spotting for 15 minutes using a Continuous Flow Microspotter. After spotting, the SensEye® was positioned in the *IBIS* MX96 biosensor and residual anti-Fc sites blocked by injection of 30 µg/mL non-specific human IgG1. Captured antibodies were conjugated to the surface using a FixIt kit (Ssens BV, The Netherlands). After sensor preparation, antibody competition analysis was performed using a classical sandwich assay. Monovalent PD-1 ECD antigen (Sino Biological, China) was diluted in HBS-EP running buffer and injected at 50 nM concentration and captured by the conjugated array of anti-PD-1 antibodies. Next, individual injections of each of the eighteen PD-1 antibodies diluted to 100 nM in HBS-EP running buffer were performed to establish antibody competition patterns. After each competition cycle, the sensor surface was regenerated with 10 mM Glycine HCl buffer, pH 2.0.

Results

Figure 5:
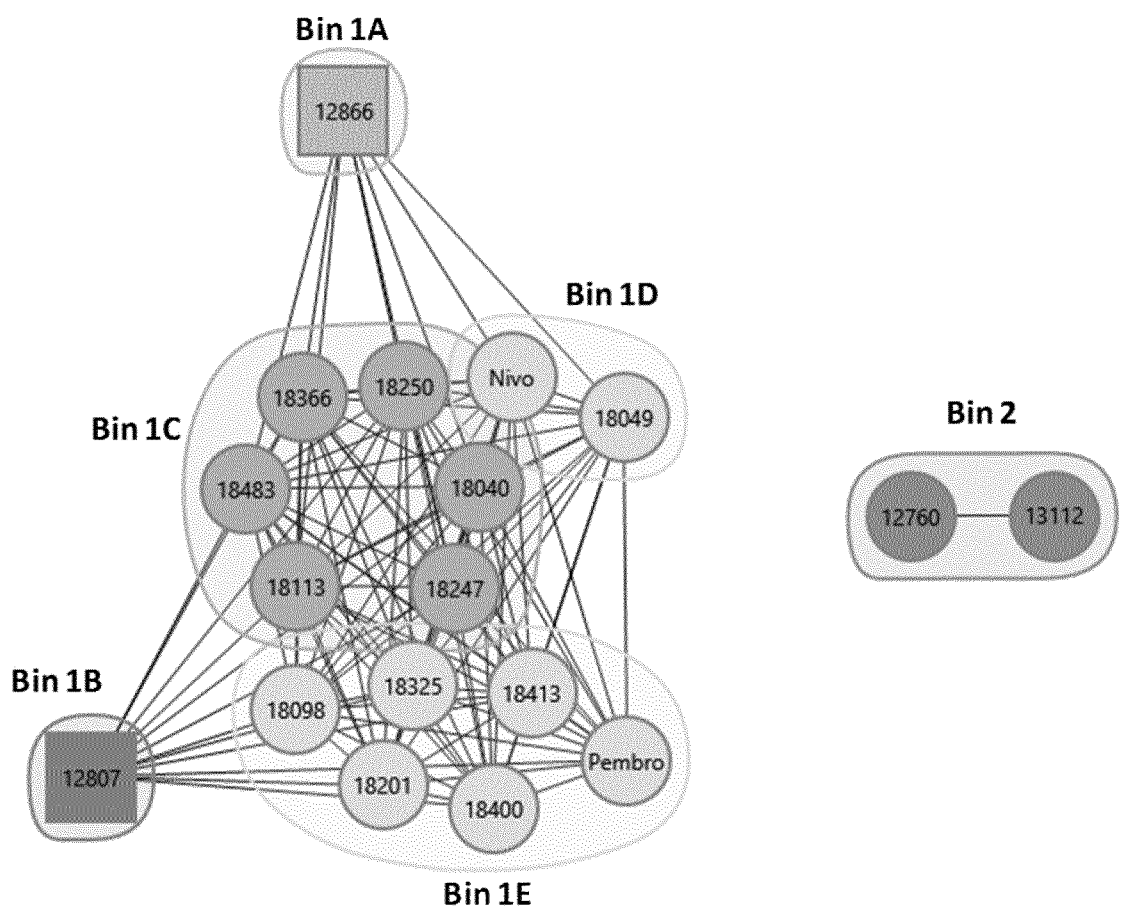
FIG. 5 shows an overview of the identified epitope groups (epitope bins) for tested anti-PD-1 antibodies and nivolumab and pembrolizumab analogues. Antibodies connected by black lines indicate cross blocking activity. Antibodies are grouped according to competition patterns with other anti-PD-1 antibodies. Nivo: nivolumab analogue; Pembro: pembrolizumab analogue.

The competition pattern of eighteen anti-PD-1 antibodies is presented in FIG. 5. Antibodies 12866 and 12807 were not found to have functional activity in cell-based assays (data not shown), but were included because they recognize distinct epitopes useful for characterizing the other epitope bins. The tested anti-PD-1 antibodies could be assigned to two main non-overlapping epitope bins. Functional antibodies belonging to epitope bin 1 all cross blocked each other, and could be further divided into sub bins based on blocking of antibodies 12866 and 12807. For instance, antibodies that blocked both mAbs 12866 and 12807 were assigned to epitope bin 1C. Epitope bin 1C includes antibodies 18366, 18483, 18113, 18247, 18040, and 18250. Antibodies in epitope bin 1D include nivolumab analogue ("Nivo") and 18049 and were characterized by blocking mAb 12866 but not 12807. Antibodies belonging to epitope bin 1 E were characterized by only blocking mAb 12807. Epitope bin 1 E includes pembrolizumab analogue ("Pembro") and antibodies 18098, 18201, 18400, 18413, and 18325.

Antibodies 12760 and 13112 do not block PD-L1 and PD-L2 ligand, and were assigned to separate epitope bin 2 because they cross blocked each other but did not block the binding of any of the antibodies from epitope Bin 1. Antibodies 12760 and 13112 likely bind to a site on PD-1 that does not overlap with the PD-L1 and PD-L2 ligand binding site.

```
                        List of Sequences

SEQ ID NO: 1
QVQLVESGGGLVKPGGSLRLSCAASGFTFSDYYMXWIRQAPGKGLEWVSYISSTGSTIYYAD
SVKGRFTISRDNAKNSLYLQMXSLRAEDTAVYYCARATNWGSDYWGQGTLVTVSS
X in position 35 is N or S
X in position 84 is D or N SEQ ID NO: 2
XIVMTQSPDSLAVSLGERATINCKSSQSVLYSSNNKNYLXWYQQKPGQPPKLLIXWASTRES
GVPDRFSGSGSGTDFTLTISSLQAEDVAVYYCQQYYSTPYTFGQGTKVEIK
X in position 1 is E or D
X in position 40 is F or A
X in position 55 is F or Y SEQ ID NO: 3
QVQLVESGGGVVQPGRSLRLSCAASGFTFSNYGMHWVRQAPGKGLEWVAVIWYDGSDKYYAD
SVKGRFTISRDNSKNTLYLQMNSLRAEDTAVYYCAGGGNYYGDFWGQGTLVTVSS SEQ ID NO: 4
XIXMTQSPSSLSASVGDRVTITCRASQGIRNDLGWYQQKPGKAPKRLIYVASXLQSGVPSRF
SGSGSGTEFTLTISSLQPEDFATYYCLQYNSYPWTFGQGTKVEIK
X in position 1 is E or D
X in position 3 is V or Q
X in position 53 is N or S
```

List of Sequences

SEQ ID NO: 5
XVQLXESGGGLVXPGGSLRLSCAASGFTFSSFAMXWVRQAPGKGLXWVSXITGGGTTSYYAD
SVKGRFTISRDNSKXTLXLQMNSLRAEDTAVYYCAKWGSWSAGAFDIWGQGTXVTVSS
X in position 1 is Q or E
X in position 5 is Q or V
X in position 13 is R or Q
X in position 35 is N or S
X in position 46 is V or E
X in position 50 is T or A
X in position 77 is S or N
X in position 80 is F or Y
X in position 115 is T or M SEQ ID NO: 6
DIQXTQSPSSVSASVGDRVTITCRASQGISSWLAWYQQKPGKAPKLLIYAASSLQSGVPSRF
SGSGSGTDFTLTISSLQPEDFATYYCQQANSFPWTFGQGTKVEIK
X in position 4 is L or M SEQ ID NO: 7
QVQLVESGGGLVKPGGSLRLSCAASGFTFSDYYMSWIRQAPGKGLEWVSYISSSGSTIYYAD
SXKGRFTISRDNAKNSLYLQMNSLRAEDTAVYYCARDTNWAFDYWGQGTLVTVSS
X in position 64 is A or V SEQ ID NO: 8
DIXXTQSPDSLAVSLGERATINCKSSQSVFYSANNKNYLAWYQQKPGQPPKLLIYWTSTRES
GVPDRFXGSGSGTDFTLTISSLQAEDVAVYYCQQFYSTPRTFGQGTKVEIK
X in position 3 is Q or V
X in position 4 is L or M
X in position 69 is R or S SEQ ID NO: 9
QVQLXESGPGLVKPSGTLSLTCAVSGGSISSNNWWSWVRQPPGKGLEWIGEIYHDGTTXYNP
SLKSTVTISVDKSXNQFSLKXSSVTAADTAVYYCARGDWGSGAFDIWGQGTMVTVSS
X in position 5 is V or Q
X in position 59 is T or N
X in position 76 is R or K
X in position 83 is M or L SEQ ID NO: 10
XIQMTQSPSSLSASVGDRVTITCRASQGIRNDLGWYQQKPGKAPKLLIYAASSLQSGVPSRF
TGSGSGTDFTLTISSLQPEDFATYYCLQDYNYPRTFGQGTKVEIK
X in position 1 is D or A SEQ ID NO: 11
QVQLVESGGXLVKPGXSLRLSCAASGFTFSDYYMSWIRQAPGKGLEWVSYISSSSSTIYYAD
SVKGRFTISTDNAKNTLYLQMNSLRAEDTAVYYCARDTNWAFDYWGQGTLVTVSS
X in position 10 is D or G
X in position 16 is R or G SEQ ID NO: 12
XIVXTQSPDSLAVSLGERATINCKSSQSVFYSSNNKNYLAWYQQKPGQPPKLLIXWASTRES
GVPTRFSGSGSGTDFTLTISSLQAEDVAVYXCQQFYSTPRTFGQGTKVEIK
X in position 1 is E or D
X in position 4 is L or M
X in position 55 is F or Y
X in position 93 is F or Y SEQ ID NO: 13
QVQLXESGGGLVKPGGSLRLSCAASGFTFRDYYMSWIRQAPGKGLEWVSXISSSGSIIXYXD
SVKGTFTISRDNAKNSLYLQMNSLRAEDTAVYYCARDTNWALDYWGQGTLVTVSS
X in position 5 is Q or V
X in position 50 is H or Y
X in position 59 is D or Y
X in position 61 is V or A SEQ ID NO: 14
DIXXTQSPDSLAVSLGERATINCKSSQSVFYSSNNKNYLAWYQQKPGQPPKLLIXWASTRES
GVPDRFSGSGSGTDFTLTISSLQAEDVAVYYCQQYYSTPYTFGQGTKLEIK
X in position 3 is Q or V
X in position 4 is L or M
X in position 55 is S or Y -continued

| List of Sequences |
|---|

SEQ ID NO: 15
XVQLXXSGGGLVQPGGSLRLSCAASGFTFSSHVMXWVRQAPGKGLEWVXXISGSGVDTYYAD
SVKGRFTISRXNSKNXLYLQMNSLRAEDTAVYYCAKWGSWSAGAFDIWGQGTMVTVSS
X in position 1 is Q or E
X in position 5 is Q or V
X in position 6 is Q or E
X in position 35 is N or S
X in position 49 is A or S
X in position 50 is T or A
X in position 73 is G or D
X in position 78 is M or T SEQ ID NO: 16
XIXXTQSPSSVSASVGDRVTITCRASQGISSWLAWYQQKPGKAPKLLIYAASSLQSGVPSRF
SGSGSGTDFTLTISSLQPEDFATYYCQQANSFPWTFGQGTKVEIK
X in position 1 is E or D
X in position 3 is V or Q
X in position 4 is L or M SEQ ID NO: 17
XVQLVXSGGGLVQPGGSLRLSCAASGFTFSSYWMSWVRQAPGKGLEWVANIKQDGSEKYYVD
SVKGRFTISRDNAKNSLYLQMNSLRAEDTAVYYCARDTNWGFDNWGQGTLVTVSS
X in position 1 is Q or E
X in position 6 is Q or E SEQ ID NO: 18
XIVMTQSPDSLAVSLGERATINCKSSQSVLYSSNNKNYLXWYQQKPGQPPKLLIXWASTRES
GVPDRFSGSGSGTDFTLTISSLQAEDVAVYYCQQYYSTPYTFGQGTKLEIK
X in position 1 is E or D
X in position 40 is L or A
X in position 55 is F or Y SEQ ID NO: 19
QXQLQESGPGLVKPSGTLSLTCAVSGGSISSSNWWSWVRQPPXKGLEWXGEIFHDGTTXYNP
SLKSRVTXSVDKSKNQFSLKLSSVTAADTAVYYCARGNWGSGALDIWGXGTMVTVSS
X in position 2 is L or V
X in position 43 is K or G
X in position 49 is V or I
X in position 59 is S or N
X in position 70 is M or I
X in position 111 is P or Q SEQ ID NO: 20
XIXMTQSPSXLSASVGDRVTITCRASQGIRNDLGWYQQKPGKAPKLLIYAASSLQSGVPSRF
SGSGSGTDFTLTISSLQPEDFATYYCLQDYNYPRTFGQGTKVEIK
X in position 1 is E or A
X in position 3 is V or Q
X in position 10 is P or S SEQ ID NO: 21
EVQLVESGGGLVQPGGSLRLSCAASGFTFSSFVMSWVRQAPGKGLEWXSXISGGGGSTYYAD
SVKGRFTISRDNSKNTLYLQMNSLRAEDTAVYYCAKDWDLYYFDYWGQGTLVTVSS
X in position 48 is L or V
X in position 50 is T or A SEQ ID NO: 22
DIQXTQSPSSVXASVGDRVTITCRASQGISNWLAWYQQKPGKAPKLLIYAASSLQSGVPSRF
SGSGSGTDFTLTISSLQPEDFATYYCQQANSFPLTFGGGTKVEIK
X in position 4 is L or M
X in position 12 is P or S SEQ ID NO: 23
XVQLXXSGGGLVQPGGSLRLSCAASGFTFSDYWMXWVRQAPGKGLEWVANIKEDGNEKYYVD
SVKGRFTISRDNAKNSLYLQMNSLRAEDTAVYYCARDTNWGSDYWGQGTLVTVSS
X in position 1 is Q or E
X in position 5 is Q or V
X in position 6 is Q or E
X in position 35 is N or S SEQ ID NO: 24
DIXMTQSPDSLAVSLGERATINCKSSQSVFYSSNNKNYLXWYQQKPGQPPKLLIXWASTRES
GVTDRFSGSGSGTDFTLTISSLQAEDVAVYYCQQYYSTPYTFGQGTKLEIK
X in position 3 is Q or V
X in position 40 is L or A
X in position 55 is F or Y

| List of Sequences |
|---|
| Constant antibody sequences |

SEQ ID NO: 25 (IgHC DNA sequence)
GCCTCCACCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCAAATCTTGTG
ACAAAACTCACACATGCCCACCGTGCCCAGCACCTGAAGCCGCGGGGGACCGTCAGTCTTC
CTCTTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTC
AGCGTCCTCACCGTCCTGCACCAGGACTGGCTGAATGGCAAGGAGTACAAGTGCAAGGTCTC
CAACAAAGCCCTCCCAGCCCCCATCGAGAAAACCATCTCCAAAGCCAAAGGGCAGCCCCGAG
AACCACAGGTGTACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCT
ATAGCAAGCTCACCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTCCCCGGGTAAA SEQ ID NO: 26 (IgHC protein sequence)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPEAAGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK SEQ ID NO: 27 (IgKC DNA sequence)
CGTACGGTGGCTGCACCATCTGTCTTCATCTTCCCGCCATCTGATGAGCAGTTGAAATCTGG
AACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTTCAACA
GGGGAGAGTGT SEQ ID NO: 28 (IgKC protein sequence)
RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

SEQ ID NO: 29 (18040/18113/18247 H-CDR1)
GFTFSDYY

SEQ ID NO: 30 (18040 H-CDR2)
ISSTGSTI

SEQ ID NO: 31 (18040 H-CDR3)
CARATNWGSDY

SEQ ID NO: 32 (18040/18366 L-CDR1)
QSVLYSSNNKNY

SEQ ID NO: 33 (18040/18247/18250/18366/18483 L-CDR2)
WAS

SEQ ID NO: 34 (18040/18250/18366/18483 L-CDR3)
CQQYYSTPYT

SEQ ID NO: 35 (18049 H-CDR1)
GFTFSNYG

SEQ ID NO: 36 (18049 H-CDR2)
IWYDGSDK

SEQ ID NO: 37 (18049 H-CDR3)
CAGGGNYYGDF

SEQ ID NO: 38 (18049/18201/18400 L-CDR1)
QGIRND

SEQ ID NO: 39 (18049 L-CDR2)
VAS

SEQ ID NO: 40 (18049 L-CDR3)
CLQYNSYPWT

```
                         List of Sequences
SEQ ID NO: 41 (18098 H-CDR1)
GFTFSSFA

SEQ ID NO: 42 (18098 H-CDR2)
ITGGGTTS

SEQ ID NO: 43 (18098/18325 H-CDR3)
CAKWGSWSAGAFDI

SEQ ID NO: 44 (18098/18325 L-CDR1)
QGISSW

SEQ ID NO: 45 (18098/18201/18325/18400/18413 L-CDR2)
AAS

SEQ ID NO: 46 (18098/18325 L-CDR3)
CQQANSFPWT

SEQ ID NO: 47 (18113 H-CDR2)
ISSSGSTI

SEQ ID NO: 48 (18113/18247 H-CDR3)
CARDTNWAFDY

SEQ ID NO: 49 (18113 L-CDR1)
QSVFYSANNKNY

SEQ ID NO: 50 (18113 L-CDR2)
WTS

SEQ ID NO: 51 (18113/18247 L-CDR3)
CQQFYSTPRT

SEQ ID NO: 52 (18201 H-CDR1)
GGSISSNNW

SEQ ID NO: 53 (18201 H-CDR2)
IYHDGTT

SEQ ID NO: 54 (18201 H-CDR3)
CARGDWGSGAFDI

SEQ ID NO: 55 (18201/18400 L-CDR3)
CLQDYNYPRT

SEQ ID NO: 56 (18247 H-CDR2)
ISSSSSTI

SEQ ID NO: 57 (18247/18250/18483 L-CDR1)
QSVFYSSNNKNY

SEQ ID NO: 58 (18250 H-CDR1)
GFTFRDYY

SEQ ID NO: 59 (18250 H-CDR2)
ISSSGSII

SEQ ID NO: 60 (18250 H-CDR3)
CARDTNWALDY

SEQ ID NO: 61 (18325 H-CDR1)
GFTFSSHV

SEQ ID NO: 62 (18325 H-CDR2)
ISGSGVDT

SEQ ID NO: 63 (18366 H-CDR1)
GFTFSSYW

SEQ ID NO: 64 (18366 H-CDR2)
IKQDGSEK

SEQ ID NO: 65 (18366 H-CDR3)
CARDTNWGFDN

SEQ ID NO: 66 (18400 H-CDR1)
GGSISSSNW
```

| List of Sequences |
|---|

SEQ ID NO: 67 (18400 H-CDR2)
IFHDGTT

SEQ ID NO: 68 (18400 H-CDR3)
CARGNWGSGALDI

SEQ ID NO: 69 (18413 H-CDR1)
GFTFSSFV

SEQ ID NO: 70 (18413 H-CDR2)
ISGGGGST

SEQ ID NO: 71 (18413 H-CDR3)
CAKDWDLYYFDY

SEQ ID NO: 72 (18413 L-CDR1)
QGISNW

SEQ ID NO: 73 (18413 L-CDR3)
CQQANSFPLT

SEQ ID NO: 74 (18483 H-CDR1)
GFTFSDYW

SEQ ID NO: 75 (18483 H-CDR2)
IKEDGNEK

SEQ ID NO: 76 (18483 H-CDR3)
CARDTNWGSDY

SEQ ID NO: 77
EVQLVESGGGLVQPGGSLRLSCAASGFTFSSFAMSWVRQAPGKGLVWVSTITGGGTTSYY
ADSVKGRFTISRDNSKSTLFLQMNSLRAEDTAVYYCAKWGSWSAGAFDIWGQGTTVTVSS

SEQ ID NO: 78
QVQLQESGPGLVKPSGTLSLTCAVSGGSISSNNWWSWVRQPPGKGLEWIGEIYHDGTTTY
NPSLKSRVTISVDKSRNQFSLKMSSVTAADTAVYYCARGDWGSGAFDIWGQGTMVTVSS

SEQ ID NO: 79
QVQLVESGGGLVKPGGSLRLSCAASGFTFRDYYMSWIRQAPGKGLEWVSHISSSGSIIDY
VDSVKGRFTISRDNAKNSLYLQMNSLRAEDTAVYYCARDTNWALDYWGQGTLVTVSS

SEQ ID NO: 80
EVQLVESGGGLVQPGGSLRLSCAASGFTFSSHVMNWVRQAPGKGLEWVATISGSGVDTYY
ADSVKGRFTISRGNSKNMLYLQMNSLRAEDTAVYYCAKWGSWSAGAFDIWGQGTMVTVSS

SEQ ID NO: 81
EVQLVESGGGLVQPGGSLRLSCAASGFTFSSYWMSWVRQAPGKGLEWVANIKQDGSEKYY
VDSVKGRFTISRDNAKNSLYLQMNSLRAEDTAVYYCARDTNWGFDNWGQGTLVTVSS

SEQ ID NO: 82
QVQLQESGPGLVKPSGTLSLTCAVSGGSISSSNWWSWVRQPPKKGLEWVGEIFHDGTTSY
NPSLKSRVTMSVDKSKNQFSLKLSSVTAADTAVYYCARGNWGSGALDIWGPGTMVTVSS

SEQ ID NO: 83
EVQLVESGGGLVQPGGSLRLSCAASGFTFSDYWMNWVRQAPGKGLEWVANIKEDGNEKYY
VDSVKGRFTISRDNAKNSLYLQMNSLRAEDTAVYYCARDTNWGSDYWGQGTLVTVSS

SEQ ID NO: 84
DIVMTQSPDSLAVSLGERATINCKSSQSVLYSSNNKNYLFWYQQKPGQPPKLLIFWASTR
ESGVPDRFSGSGSGTDFTLTISSLQAEDVAVYYCQQYYSTPYTFGQGTKVEIK

SEQ ID NO: 85
DIQMTQSPSSLSASVGDRVTITCRASQGIRNDLGWYQQKPGKAPKRLIYVASNLQSGVPS
RFSGSGSGTEFTLTISSLQPEDFATYYCLQYNSYPWTFGQGTKVEIK

SEQ ID NO: 86
DIQLTQSPSSVSASVGDRVTITCRASQGISSWLAWYQQKPGKAPKLLIYAASSLQSGVPS
RFSGSGSGTDFTLTISSLQPEDFATYYCQQANSFPWTFGQGTKVEIK

SEQ ID NO: 87
DIVMTQSPDSLAVSLGERATINCKSSQSVFYSANNKNYLAWYQQKPGQPPKLLIYWTSTR
ESGVPDRFRGSGSGTDFTLTISSLQAEDVAVYYCQQFYSTPRTFGQGTKVEIK

SEQ ID NO: 88
AIQMTQSPSSLSASVGDRVTITCRASQGIRNDLGWYQQKPGKAPKLLIYAASSLQSGVPS
RFSGSGSGTDFTLTISSLQPEDFATYYCLQDYNYPRTFGQGTKVEIK

List of Sequences

SEQ ID NO: 89
DIVMTQSPDSLAVSLGERATINCKSSQSVFYSSNNKNYLAWYQQKPGQPPKLLIFWASTR
ESGVPDRFSGSGSGTDFTLTISSLQAEDVAVYFCQQFYSTPRTFGQGTKVEIK

SEQ ID NO: 90
DIVMTQSPDSLAVSLGERATINCKSSQSVFYSSNNKNYLAWYQQKPGQPPKLLISWASTR
ESGVPDRFSGSGSGTDFTLTISSLQAEDVAVYYCQQYYSTPYTFGQGTKLEIK

SEQ ID NO: 91
DIQMTQSPSSVSASVGDRVTITCRASQGISSWLAWYQQKPGKAPKLLIYAASSLQSGVPS
RFSGSGSGTDFTLTISSLQPEDFATYYCQQANSFPWTFGQGTKVEIK

SEQ ID NO: 92
DIVMTQSPDSLAVSLGERATINCKSSQSVLYSSNNKNYLLWYQQKPGQPPKLLIFWASTR
ESGVPDRFSGSGSGTDFTLTISSLQAEDVAVYYCQQYYSTPYTFGQGTKLEIK

SEQ ID NO: 93
AIQMTQSPSPLSASVGDRVTITCRASQGIRNDLGWYQQKPGKAPKLLIYAASSLQSGVPS
RFSGSGSGTDFTLTISSLQPEDFATYYCLQDYNYPRTFGQGTKVEIK

SEQ ID NO: 94
DIQLTQSPSSVPASVGDRVTITCRASQGISNWLAWYQQKPGKAPKLLIYAASSLQSGVPS
RFSGSGSGTDFTLTISSLQPEDFATYYCQQANSFPLTFGGGTKVEIK

SEQ ID NO: 95
DIVMTQSPDSLAVSLGERATINCKSSQSVFYSSNNKNYLLWYQQKPGQPPKLLIFWASTR
ESGVPDRFSGSGSGTDFTLTISSLQAEDVAVYYCQQYYSTPYTFGQGTKLEIK

SEQ ID NO: 96
QVQLVESGGGLVKPGGSLRLSCAASGFTFSDYYMSWIRQAPGKGLEWVSYISSTGSTIYY
ADSVKGRFTISRDNAKNSLYLQMNSLRAEDTAVYYCARATNWGSDYWGQGTLVTVSS

SEQ ID NO: 97
EVQLVESGGGLVQPGGSLRLSCAASGFTFSSFAMSWVRQAPGKGLEWVSAITGGGTTSYY
ADSVKGRFTISRDNSKNTLYLQMNSLRAEDTAVYYCAKWGSWSAGAFDIWGQGTMVTVSS

SEQ ID NO: 98
QVQLVESGGGLVKPGGSLRLSCAASGFTFSDYYMSWIRQAPGKGLEWVSYISSSGSTIYY
ADSVKGRFTISRDNAKNSLYLQMNSLRAEDTAVYYCARDTNWAFDYWGQGTLVTVSS

SEQ ID NO: 99
QVQLQESGPGLVKPSGTLSLTCAVSGGSISSNNWWSWVRQPPGKGLEWIGEIYHDGTTNY
NPSLKSRVTISVDKSKNQFSLKLSSVTAADTAVYYCARGDWGSGAFDIWGQGTMVTVSS

SEQ ID NO: 100
QVQLVESGGGLVKPGGSLRLSCAASGFTFSDYYMSWIRQAPGKGLEWVSYISSSSSTIYY
ADSVKGRFTISRDNAKNSLYLQMNSLRAEDTAVYYCARDTNWAFDYWGQGTLVTVSS

SEQ ID NO: 101
QVQLVESGGGLVKPGGSLRLSCAASGFTFRDYYMSWIRQAPGKGLEWVSYISSSGSIIYY
ADSVKGRFTISRDNAKNSLYLQMNSLRAEDTAVYYCARDTNWALDYWGQGTLVTVSS

SEQ ID NO: 102
EVQLVESGGGLVQPGGSLRLSCAASGFTFSSHVMNWVRQAPGKGLEWVSAISGSGVDTYY
ADSVKGRFTISRDNSKNTLYLQMNSLRAEDTAVYYCAKWGSWSAGAFDIWGQGTMVTVSS

SEQ ID NO: 103
QVQLQESGPGLVKPSGTLSLTCAVSGGSISSSNWWSWVRQPPGKGLEWIGEIFHDGTTNY
NPSLKSRVTISVDKSKNQFSLKLSSVTAADTAVYYCARGNWGSGALDIWGQGTMVTVSS

SEQ ID NO: 104
EVQLVESGGGLVQPGGSLRLSCAASGFTFSSFVMSWVRQAPGKGLEWVSAISGGGSTYY
ADSVKGRFTISRDNSKNTLYLQMNSLRAEDTAVYYCAKDWDLYYFDYWGQGTLVTVSS

SEQ ID NO: 105
EVQLVESGGGLVQPGGSLRLSCAASGFTFSDYWMSWVRQAPGKGLEWVANIKEDGNEKYY
VDSVKGRFTISRDNAKNSLYLQMNSLRAEDTAVYYCARDTNWGSDYWGQGTLVTVSS

SEQ ID NO: 106
DIVMTQSPDSLAVSLGERATINCKSSQSVLYSSNNKNYLAWYQQKPGQPPKLLIYWASTR
ESGVPDRFSGSGSGTDFTLTISSLQAEDVAVYYCQQYYSTPYTFGQGTKVEIK

SEQ ID NO: 107
DIQMTQSPSSLSASVGDRVTITCRASQGIRNDLGWYQQKPGKAPKRLIYVASSLQSGVPS
RFSGSGSGTEFTLTISSLQPEDFATYYCLQYNSYPWTFGQGTKVEIK

-continued

List of Sequences

SEQ ID NO: 108
DIVMTQSPDSLAVSLGERATINCKSSQSVFYSANNKNYLAWYQQKPGQPPKLLIYWTSTR
ESGVPDRFSGSGSGTDFTLTISSLQAEDVAVYYCQQFYSTPRTFGQGTKVEIK

SEQ ID NO: 109
DIVMTQSPDSLAVSLGERATINCKSSQSVFYSSNNKNYLAWYQQKPGQPPKLLIYWASTR
ESGVPDRFSGSGSGTDFTLTISSLQAEDVAVYYCQQFYSTPRTFGQGTKVEIK

SEQ ID NO: 110
DIVMTQSPDSLAVSLGERATINCKSSQSVFYSSNNKNYLAWYQQKPGQPPKLLIYWASTR
ESGVPDRFSGSGSGTDFTLTISSLQAEDVAVYYCQQYYSTPYTFGQGTKLEIK

SEQ ID NO: 111
DIVMTQSPDSLAVSLGERATINCKSSQSVLYSSNNKNYLAWYQQKPGQPPKLLIYWASTR
ESGVPDRFSGSGSGTDFTLTISSLQAEDVAVYYCQQYYSTPYTFGQGTKLEIK

SEQ ID NO: 112
AIQMTQSPSSLSASVGDRVTITCRASQGIRNDLGWYQQKPGKAPKLLIYAASSLQSGVPS
RFSGSGSGTDFTLTISSLQPEDFATYYCLQDYNYPRTFGQGTKVEIK

SEQ ID NO: 113
DIQLTQSPSSVPASVGDRVTITCRASQGISNWLAWYQQKPGKAPKLLIYAASSLQSGVPS
RFSGSGSGTDFTLTISSLQPEDFATYYCQQANSFPLTFGGGTKVEIK

SEQ ID NO: 114
DIVMTQSPDSLAVSLGERATINCKSSQSVFYSSNNKNYLAWYQQKPGQPPKLLIYWASTR
ESGVPDRFSGSGSGTDFTLTISSLQAEDVAVYYCQQYYSTPYTFGQGTKLEIK

SEQ ID NO: 115
GGGGSGGGGSGGGGS

The invention claimed is:

1. An anti-PD-1 antibody or an antigen-binding portion thereof, wherein said antibody comprises the H-CDR1-3 and L-CDR1-3 amino acid sequences of:
   a) SEQ ID NOs: 29, 30, 31, 32, 33, and 34, respectively;
   b) SEQ ID NOs: 35, 36, 37, 38, 39, and 40, respectively;
   c) SEQ ID NOs: 41, 42, 43, 44, 45, and 46, respectively;
   d) SEQ ID NOs: 29, 47, 48, 49, 50, and 51, respectively;
   e) SEQ ID NOs: 52, 53, 54, 38, 45, and 55, respectively;
   f) SEQ ID NOs: 29, 56, 48, 57, 33, and 51, respectively;
   g) SEQ ID NOs: 58, 59, 60, 57, 33, and 34, respectively;
   h) SEQ ID NOs: 61, 62, 43, 44, 45, and 46, respectively;
   i) SEQ ID NOs: 63, 64, 65, 32, 33, and 34, respectively;
   j) SEQ ID NOs: 66, 67, 68, 38, 45, and 55, respectively;
   k) SEQ ID NOs: 69, 70, 71, 72, 45, and 73, respectively; or
   l) SEQ ID NOs: 74, 75, 76, 57, 33, and 34, respectively.

2. The anti-PD-1 antibody or antigen-binding portion of claim 1, wherein said antibody comprises a heavy chain variable domain and a light chain variable domain, wherein said heavy and light chain variable domains have the amino acid sequences of:
   a) SEQ ID NOs: 1 and 2, respectively;
   b) SEQ ID NOs: 3 and 4, respectively;
   c) SEQ ID NOs: 5 and 6, respectively;
   d) SEQ ID NOs: 7 and 8, respectively;
   e) SEQ ID NOs: 9 and 10, respectively;
   f) SEQ ID NOs: 11 and 12, respectively;
   g) SEQ ID NOs: 13 and 14, respectively;
   h) SEQ ID NOs: 15 and 16, respectively;
   i) SEQ ID NOs: 17 and 18, respectively;
   j) SEQ ID NOs: 19 and 20, respectively;
   k) SEQ ID NOs: 21 and 22, respectively; or
   l) SEQ ID NOs: 23 and 24, respectively.

3. The anti-PD-1 antibody of claim 1, wherein the antibody is of isotype IgG subclass IgG1.

4. The anti-PD-1 antibody of claim 3, wherein the antibody comprises at least one mutation in the Fc region.

5. The anti-PD-1 antibody of claim 4, wherein one or both of the amino acid residues at positions 234 and 235 are mutated to Ala.

6. The anti-PD-1 antibody or antigen-binding portion of claim 1, wherein the antibody or portion has at least one of the following properties:
   a) binds to cynomolgus PD-1 with a $K_D$ of $4\times10^{-8}$ M or less;
   b) binds to mouse PD-1 with a $K_D$ of $2\times10^{-8}$ M or less;
   c) binds to human PD-1 with a $K_D$ of $3\times10^{-9}$ M or less;
   d) inhibits the interaction of PD-1 with PD-L1 at a concentration of 10 µg/ml;
   e) stimulates IL-2 production in an SEB (Staphylococcal enterotoxin B) whole blood assay; and
   f) stimulates IFN-γ production in a one-way mixed lymphocyte reaction assay.

7. A pharmaceutical composition comprising an anti-PD-1 antibody or antigen-binding portion thereof according to claim 1 and a pharmaceutically acceptable excipient.

8. A bi-specific binding molecule having the binding specificities of any two distinct anti-PD-1 antibodies or antigen-binding portions thereof according to claim 1.

9. A method for enhancing immunity in a patient in need thereof, comprising administering to said patient the anti-PD-1 antibody or antigen-binding portion according to claim 1.

10. The method of claim 9, further comprising administering to the patient an immunostimulatory agent, a vaccine, a chemotherapeutic agent, an anti-neoplastic agent, an anti-angiogenic agent, a tyrosine kinase inhibitor, a PD-1 pathway inhibitor, or radiation therapy.

11. A method for treating cancer in a patient, comprising administering to said patient the antibody or antigen-binding portion according to claim 1.

12. The method of claim 11, wherein the cancer originates in a tissue selected from the group consisting of skin, lung, intestine, colon, ovary, brain, prostate, kidney, soft tissues, hematopoietic system, head and neck, liver, bladder, breast, stomach, uterus and pancreas.

13. The method of claim 11, wherein the cancer is selected from the group consisting of advanced or metastatic melanoma, non-small cell lung cancer, head and neck squamous cell cancer, bladder cancer, gastric cancer, renal cell carcinoma, hepatocellular carcinoma, colorectal cancer, and Hodgkin's lymphoma.

14. An anti-PD-1 antibody that comprises:
   a) a heavy chain (HC) with the amino acid sequences of SEQ ID NOs: 1 and 26 and a light chain (LC) with the amino acid sequences of SEQ ID NOs: 2 and 28;
   b) an HC with the amino acid sequences of SEQ ID NOs: 3 and 26 and an LC with the amino acid sequences of SEQ ID NOs: 4 and 28;
   c) an HC with the amino acid sequences of SEQ ID NOs: 5 and 26 and an LC with the amino acid sequences of SEQ ID NOs: 6 and 28;
   d) an HC with the amino acid sequences of SEQ ID NOs: 7 and 26 and an LC with the amino acid sequences of SEQ ID NOs: 8 and 28;
   e) an HC with the amino acid sequences of SEQ ID NOs: 9 and 26 and an LC with the amino acid sequences of SEQ ID NOs: 10 and 28;
   f) an HC with the amino acid sequences of SEQ ID NOs: 11 and 26 and an LC with the amino acid sequences of SEQ ID NOs: 12 and 28;
   g) an HC with the amino acid sequences of SEQ ID NOs: 13 and 26 and an LC with the amino acid sequences of SEQ ID NOs: 14 and 28;
   h) an HC with the amino acid sequences of SEQ ID NOs: 15 and 26 and an LC with the amino acid sequences of SEQ ID NOs: 16 and 28;
   i) an HC with the amino acid sequences of SEQ ID NOs: 17 and 26 and an LC with the amino acid sequences of SEQ ID NOs: 18 and 28;
   j) an HC with the amino acid sequences of SEQ ID NOs: 19 and 26 and an LC with the amino acid sequences of SEQ ID NOs: 20 and 28;
   k) an HC with the amino acid sequences of SEQ ID NOs: 21 and 26 and an LC with the amino acid sequences of SEQ ID NOs: 22 and 28; or
   l) an HC with the amino acid sequences of SEQ ID NOs: 23 and 26 and an LC with the amino acid sequences of SEQ ID NOs: 24 and 28.

15. An anti-PD-1 antibody that comprises a heavy chain (HC) with the amino acid sequences of SEQ ID NOs: 9 and 26 and a light chain (LC) with the amino acid sequences of SEQ ID NOs: 10 and 28.

16. A pharmaceutical composition comprising an anti-PD-1 antibody according to claim 15 and a pharmaceutically acceptable excipient.

17. A method for enhancing immunity in a patient in need thereof, comprising administering to said patient the anti-PD-1 antibody according to claim 15.

18. The method of claim 17, further comprising administering to the patient an immunostimulatory agent, a vaccine, a chemotherapeutic agent, an anti-neoplastic agent, an anti-angiogenic agent, a tyrosine kinase inhibitor, a PD-1 pathway inhibitor, or radiation therapy.

19. A method for treating cancer in a patient, comprising administering to said patient the antibody according to claim 15.

20. The method of claim 19, wherein the cancer
   a) originates in a tissue selected from the group consisting of skin, lung, intestine, colon, ovary, brain, prostate, kidney, soft tissues, hematopoietic system, head and neck, liver, bladder, breast, stomach, uterus and pancreas; or
   b) is selected from the group consisting of advanced or metastatic melanoma, non-small cell lung cancer, head and neck squamous cell cancer, bladder cancer, gastric cancer, renal cell carcinoma, hepatocellular carcinoma, colorectal cancer, and Hodgkin's lymphoma.

* * * * *